United States Patent [19]

Effland et al.

[11] Patent Number: 5,328,920
[45] Date of Patent: * Jul. 12, 1994

[54] SUBSTITUTED (PYRIDINYLAMINO)-INDOLES

[75] Inventors: Richard C. Effland; Joseph T. Klein, both of Bridgewater; Lawrence L. Martin, Lebanon; Gregory M. Shutske, Flemington; Kevin J. Kapples, Little York. all of N.J.; John D. Tomer, IV, Perkasie, Pa.

[73] Assignee: Hoechst-Roussel Pharmaceuticals Incorporated, Somerville, N.J.

[ * ] Notice: The portion of the term of this patent subsequent to Jan. 5, 2010 has been disclaimed.

[21] Appl. No.: 964,546

[22] Filed: Oct. 21, 1992

Related U.S. Application Data

[63] Continuation-in-part of Ser. No. 688,964, Apr. 17, 1991, Pat. No. 5,177,088.

[51] Int. Cl.$^5$ .................... C07D 401/12; A61K 31/44
[52] U.S. Cl. ..................... 514/339; 546/273; 546/270; 546/256; 514/338; 514/333
[58] Field of Search ........ 546/273, 270, 256; 514/339, 333, 338

[56] References Cited

U.S. PATENT DOCUMENTS

| | | | |
|---|---|---|---|
| 4,474,964 | 10/1984 | Ibuki et al. | 546/199 |
| 4,954,502 | 9/1990 | Smith et al. | 544/349 |
| 4,954,503 | 9/1990 | Strupczewski et al. | 544/230 |

FOREIGN PATENT DOCUMENTS

| | | |
|---|---|---|
| 0200322 | 11/1986 | European Pat. Off. . |
| 0224830 | 6/1987 | European Pat. Off. . |
| 0402644 | 12/1989 | European Pat. Off. . |
| 0429984A3 | 6/1991 | European Pat. Off. . |

OTHER PUBLICATIONS

Peroutka, Biological Psychiatry (1985) 20, 971–979.
Panda, Ind. J. Chem. (1987) 26B, 431–435.
Kwartler, J. Amer. Chem. Soc. (1943) 65 1804–1806.
Vivona, J. Heterocyclic Chem. (1979) 16, 783–784.
Houlihan, ed. "Indoles", Part II, 210–212 Wiley-Interscience (1972).

Primary Examiner—Jane T. Fan
Attorney, Agent, or Firm—Tatsuya Ikeda

[57] ABSTRACT

There are disclosed various compounds of the formula below,

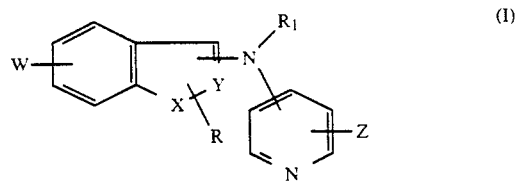

(I)

where R, $R_1$, W, X, Y and Z are as defined in the specification; which are useful for alleviating various memory dysfunctions such as Alzheimer's disease, as modulators of neurotransmitter functions such as serotonergic and adrenergic, and as such are useful as antidepressants, anxiolytics, atypical antipsychotics, antiemetics, and for the treatment of personality disorders such as obsessive compulsive disorder.

11 Claims, No Drawings

SUBSTITUTED (PYRIDINYLAMINO)-INDOLES

This is a continuation-in-part of a prior application, Ser. No. 688,964 filed Apr. 17, 1991 now U.S. Pat. No. 5,177,088.

The present invention relates to compounds of the formula,

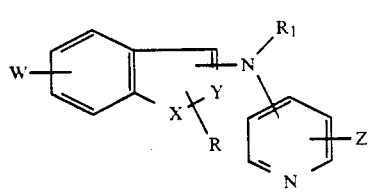
(I)

where

R is hydrogen, loweralkyl, carboxyl or loweralkoxycarbonyl;

$R_1$ is hydrogen, loweralkyl, loweralkenyl, loweralkynyl, arylloweralkyl, cycloalkylloweralkyl, loweralkoxyloweralkyl, hydroxyloweralkyl, aminoloweralkyl, mono- or di-loweralkylaminoloweralkyl, formyl, loweralkylcarbonyl, aminoloweralkylcarbonyl, loweralkoxycarbonyl, mono-or di-aryl-substituted loweralkyl, arylcarbonylloweralkyl, aryloxyloweralkyl, or

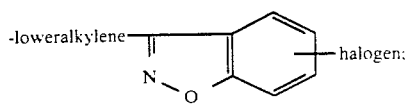

—X— is

—O— or —S—, $R_2$ being hydrogen, loweralkyl or loweralkylcarbonyl;

—Y= is —CH= or —N=, provided that the hydrogen atom of the group —CH= may be replaced by either the group R or the group

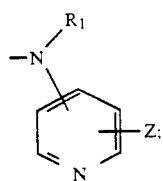

W is hydrogen, halogen, hydroxy, loweralkoxy, arylloweralkoxy, nitro, trifluoromethyl or

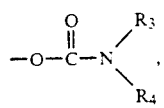

where $R_3$ is hydrogen, loweralkyl or arylloweralkyl; and $R_4$ is loweralkyl or arylloweralkyl; or alternatively the group

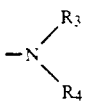

as a whole is

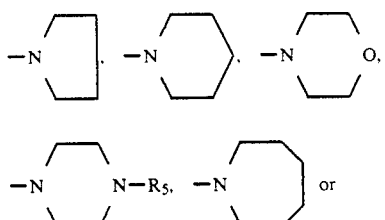

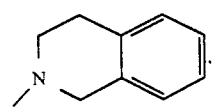

$R_5$ being hydrogen, loweralkyl, aryl or arylloweralkyl; and

Z is hydrogen, halogen, loweralkyl, nitro or amino; which are useful for alleviating various memory dysfunctions such as Alzheimer's disease, as modulators of neurotransmitter function such as serotonergic and adrenergic, inhibitors of monoamine oxidase, and reduce drinking behavior in polydipsic anmials, and as such are useful as antidepressants, anxiolytics, atypical antipsychotics, antiemetics, and for the treatment of personality disorders such as obsessive compulsive disorder.

The generic Formula I depicted above encompasses the subgeneric Formulas (Ia) through (Ii) depicted below where $R_6$ is hydrogen or loweralkyl, and $R_7$ is hydrogen or loweralkyl:

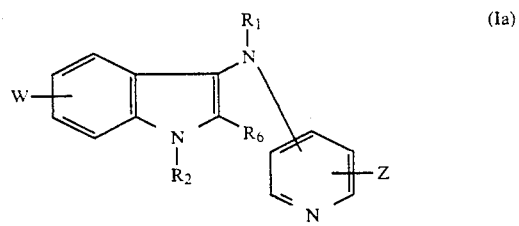
(Ia)

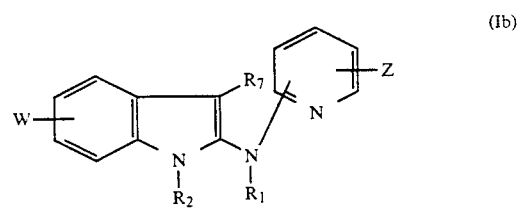
(Ib)

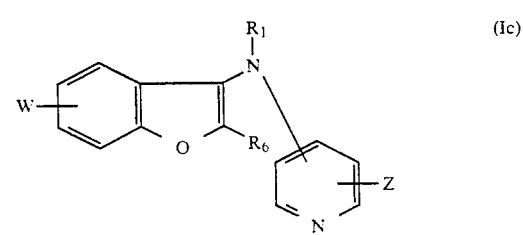
(Ic)

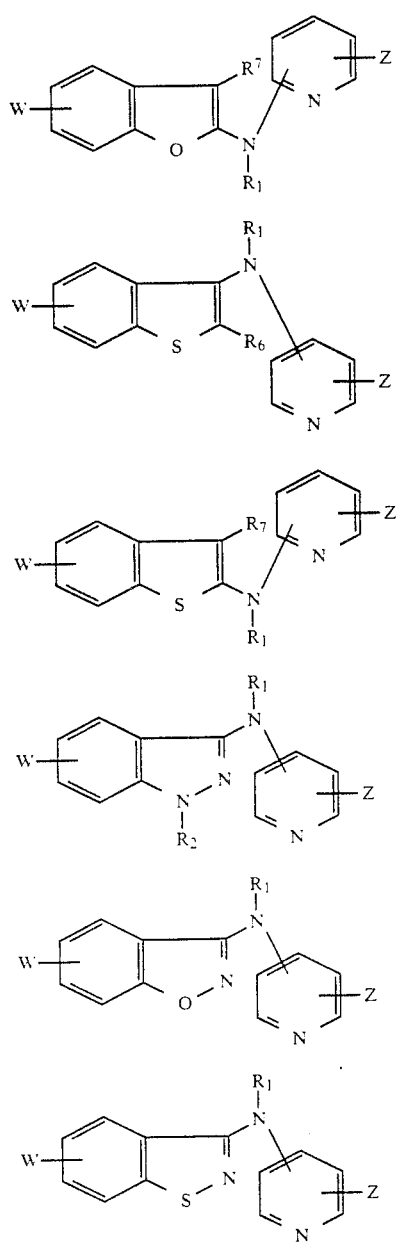

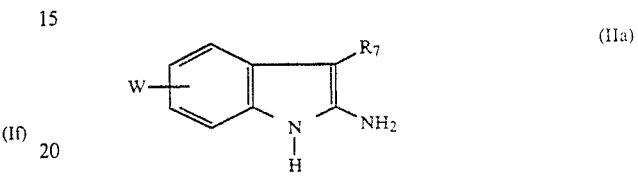

Unless otherwise stated or indicated, the following definitions shall apply throughout the specification and the appended claims.

The term loweralkyl shall mean a straight or branched alkyl group having from 1 to 6 carbon atoms. Examples of said loweralkyl include methyl, ethyl, n-propyl, iso-propyl, n-butyl, iso-butyl, sec-butyl, t-butyl and straight- and branched-chain pentyl and hexyl.

The term halogen shall mean fluorine, chlorine, bromine or iodine.

The term aryl shall mean a phenyl group substituted with 0, 1 or 2 substituents each of which being independently loweralkyl, loweralkoxy, loweralkylcarbonyl, halogen or trifluoromethyl.

The term cycloalkyl shall mean a cycloalkyl group of 3 to 8 carbon atoms.

Throughout the specification and the appended claims, a given chemical formula or name shall encompass all stereo, optical and tautomeric isomers where such isomers exist.

The compounds of this invention are prepared by utilizing one or more of the synthetic steps described below.

Throughout the description of the synthetic steps, the notations R, $R_1$ through $R_7$, W, X, Y and Z shall have the respective meanings given above unless otherwise stated or indicated and other notations shall have their respective meanings as defined in their first appearances.

The starting 2-aminoindoles of Formula IIa can be prepared by various methods known to the art.

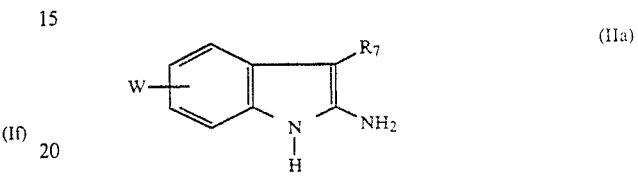

Thus, for instance, one can utilize the method described in Pschorr and Hoppe, Chem. Ber. 43, 2543 (1910) to effectuate the reaction schematically depicted below.

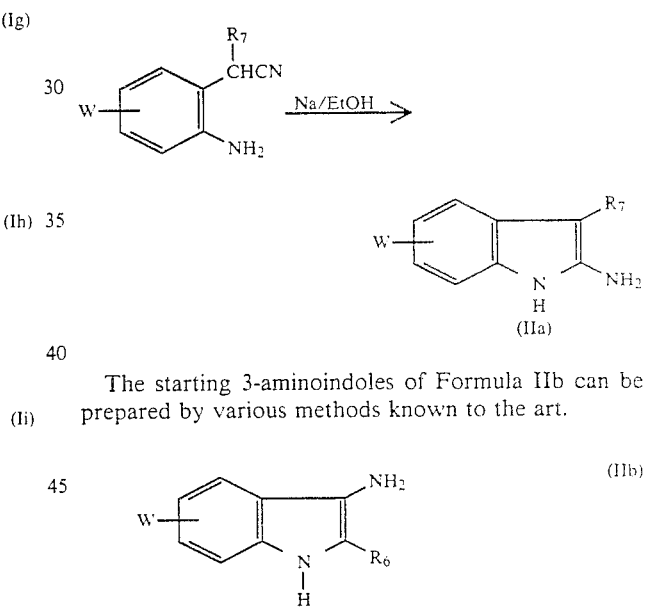

The starting 3-aminoindoles of Formula IIb can be prepared by various methods known to the art.

Thus, for instance, one can utilize the method described in Gilchrist et al, J. Chem. Soc. Perkin Trans. I, 551 (1973) to effectuate the reaction schematically depicted below.

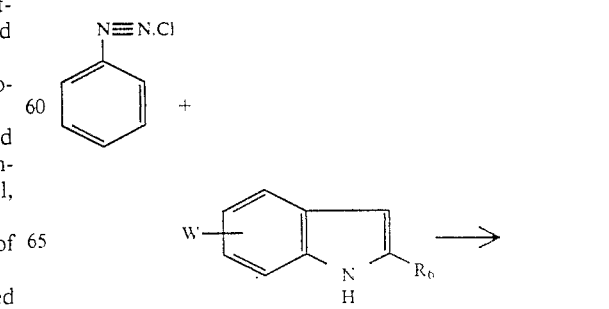

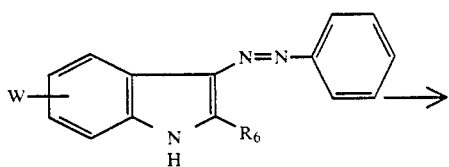

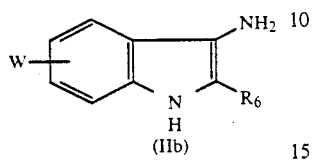
(IIb)

Alternatively to the above, compounds IIb can also be prepared by reducing the 3-nitrosoindoles of Formula (III) with a suitable reducing agent such as Na$_2$S$_2$O$_8$ or Pd/H$_2$. See in this regard, "Indoles", Part II, edited by W. J. Houlihan, Wiley-Interscience, New York, 1972 and European Patent Application 0,224,830 (1987).

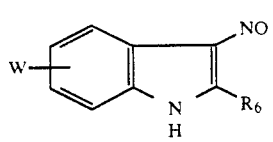
(III)

The starting 3-aminobenzo[b]thiophenes of Formula IVa can be prepared by various methods known to the art.

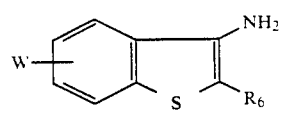
(IVa)

Thus, for instance, one can lithiate the starting benzo[b]thiophene to obtain the corresponding 2-lithio compound (see for instance Shirley and Cameron, J. Amer. Chem. Soc., 72, 2788 (1950)), alkylate the latter to obtain the 2-alkyl compound, nitrate the latter to obtain the 2-alkyl-3-nitro compound (see for instance, Shirley, Danzig and Canter, J. Amer. Chem. Soc., 75, 3278 (1953)) and reduce the latter to obtain compound IVa. The reaction sequence is depicted below schematically.

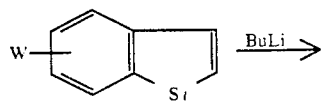

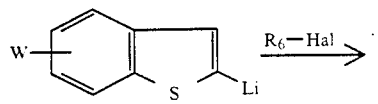

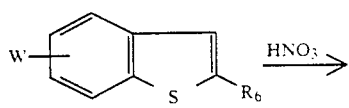

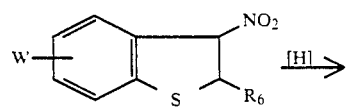

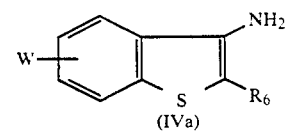
(IVa)

In the special case of compounds IVa where R$_6$ is hydrogen, it is convenient to use the reaction sequence depicted schematically below. See J. R. Beck, J. Org. Chem., 37, 3224 (1972).

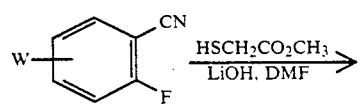

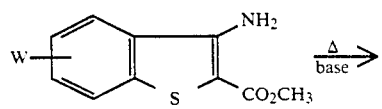

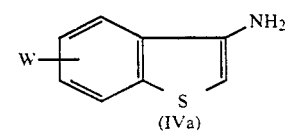
(IVa)

The starting 2-aminobenzo[b]thiophenes of Formula IVb can also be prepared by various methods known to the art.

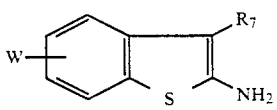
(IVb)

Thus, for instance, one can formulate the starting benzo[b]thiophene by virtue of a Vilsmeier reaction to obtain the corresponding 3-formyl compound, subject the latter to a Wittig reaction using an appropriate Wittig reagent to obtain a compound of Formula IVc where R'$_7$ is hydrogen or a loweralkyl group of 1–4 carbon atoms, reduce said compound IVc to obtain the corresponding 3-alkyl compound IVd, nitrate the latter to obtain the 3-alkyl-2-nitro compound IVe (see for instance, Shirley, Danzig and Canter, J. Amer. Chem. Soc., 75, 3278 (1953)) and reduce the latter to obtain compound IVb.

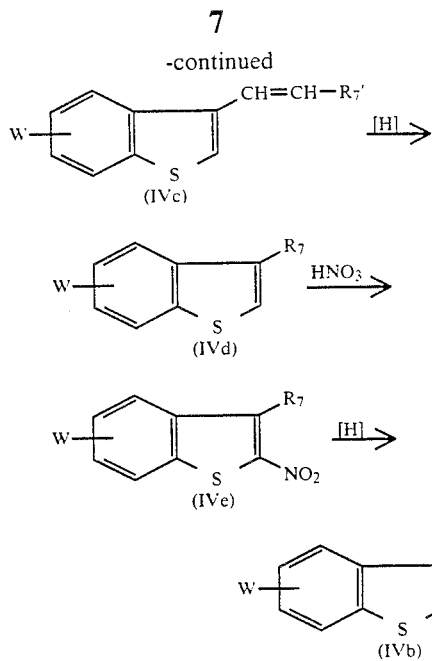

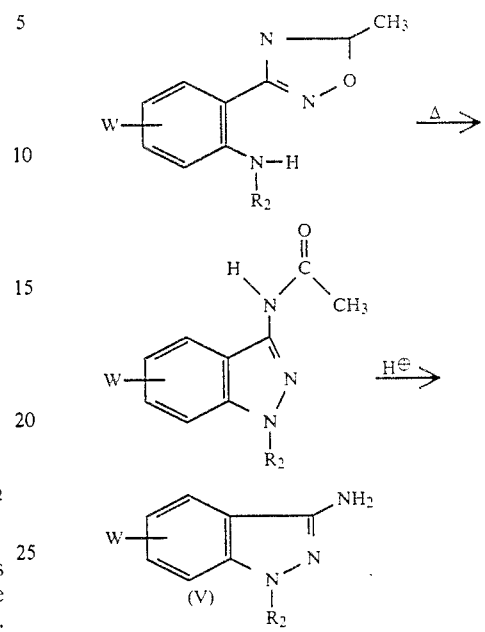

In the special case of compounds IVb where $R_7$ is hydrogen, it is convenient to use the reaction sequence depicted schematically below. See G. W. Stacy et al, J. Org. Chem., 30, 4074 (1965).

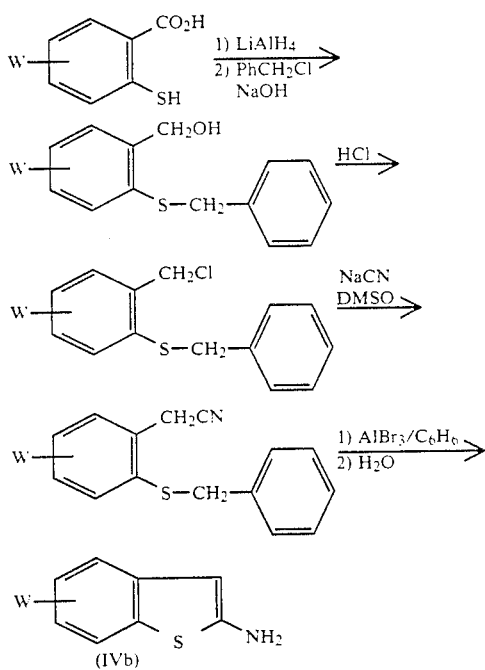

The starting 3-aminoindazoles of Formula V can be prepared by various methods known to the art.

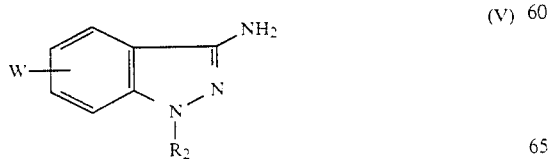

Thus, for instance, one can utilize the reaction scheme disclosed in Virona et al., J. Heterocyclic Chem., 16, 783 (1989) to effectuate the reaction sequence depicted below.

2-Amino-4-nitrobenzo[b]furans depicted as Formula VI below is a compound known to the art. See, for instance, N. Makosza et al, Liebigs Ann. Chem. 1988, 203–20. In preparing the target compounds of Formula Id, it is expedient in this invention to used said compound VI as a starting compound rather than compounds depicted as Formula VII below.

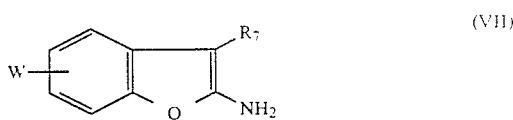

The starting 3-amino-1,2-benzisoxazoles of Formula VIII can be prepared by utilizing various methods known to the art. Thus, for instance, one can prepare compounds VIII by the procedure outlined below, described in Shutske and Kapples, J. Heterocyclic Chem., 26, 1293 (1989).

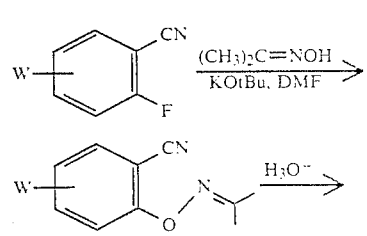

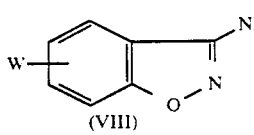
(VIII)

3-Amino-1,2-benzisothiazole of Formula IXa is known to the art. This compound can be synthesized by various methods known to the art. See, for instance, Böshagen U.S. Pat. No. 3,692,795; Fleig et al, U.S. Pat. No. 4,140,692; and British Patent 1,249,459. One can introduce various substituents W as defined earlier into the benzene ring moiety of 3-amino-1,2-benzisothiazole with the aid of various synthetic methods known to the art to obtain various compounds of Formula IXb which are used as starting compounds of this invention.

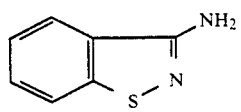
(IXa)

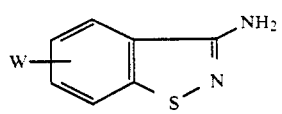
(IXb)

STEP A:

A compound of Formula X which is prepared with the aid of one of the synthetic routes described above is allowed to react with a chloropyridine hydrochloride to afford a compound of Formula XI.

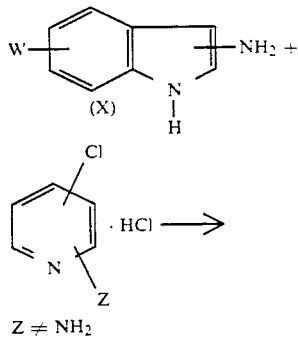

Said reaction is typically conducted in an ethereal solvent such as bis(2-methoxyethyl)ether, diethyl ether, dimethoxyethane, dioxane or tetrahydrofuran or polar aprotic solvent such as dimethylformamide, dimethylacetamide, N-methyl-2-pyrrolidone, hexamethylphosphoramide or dimethylsulfoxide or protic solvent such as ethanol or isopropanol at a temperature of between about 20° C. and 150° C.

STEP B:

Compound XI is allowed to react with a loweralkyl chloroformate of the formula Cl—CO—OR$_8$ where R$_8$ is loweralkyl to afford a compound of Formula XII.

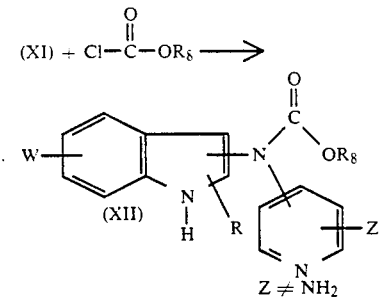

Said reaction is conducted typically in a suitable solvent such as dichloromethane in the presence of a suitable base such as sodium bicarbonate or triethylamine at a temperature of about 20°-60° C.

STEP C:

Compound XII is allowed to react with a loweralkyl halide of the formula R$_2$-Hal where R$_2$ is loweralkyl and Hal is chlorine or bromine, or with a diloweralkyl sulfate of the formula (R$_2$O)$_2$SO$_2$ in a routine manner known to the art to afford a compound of Formula XIII.

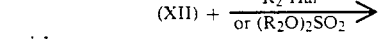

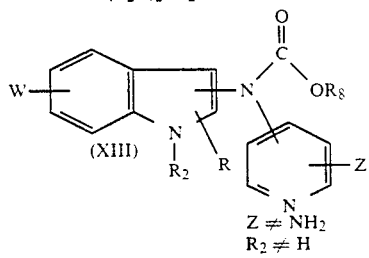

Said reaction is conducted typically in a suitable solvent such as dimethylformamide or tetrahydrofuran in the presence of a suitable base such as sodium or potassium hydride or potassium-t-butoxide at a temperature of about 0°-120° C.

STEP D:

Compound XIII is hydrolyzed to afford a compound of Formula XIV.

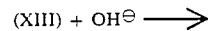

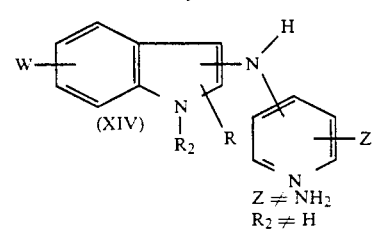

Said hydrolysis is conducted typically by stirring a mixture comprising compound XIII, an alkali hydroxide such as sodium hydroxide and a suitable medium such as ethanol or other loweralkanol plus water at a temperature of about 20°-100° C.

STEP E:

Compound XIV is allowed to react with a halide compound of the formula $R_9$-Hal, where $R_9$ is loweralkyl, loweralkenyl, loweralkynyl or arylloweralkyl, at a temperature of about $-10°$ C.$-80°$ C., preferably between $0°$ C.$-25°$ C. to afford a compound of Formula XV.

(XIV) + $R_9$-Hal $\longrightarrow$

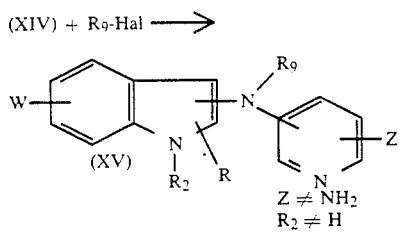

Said reaction is conducted typically in a suitable solvent such as dimethylformamide, dimethylsulfoxide, ethereal solvents or aromatic hydrocarbon in the presence of a suitable base such as sodium or potassium hydride or potassium-t-butoxide.

Compound XIV is allowed to react with a compound of the formula

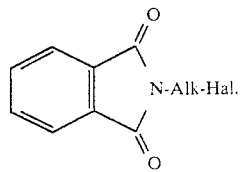

where "Alk" is a loweralkylene group and Hal is Cl or Br in a routine manner known to the art to afford a compound of Formula XVI. Thereafter, compound XVI is treated with hydrazine or methylamine in a routine manner known to the art to afford a compound of Formula XVII.

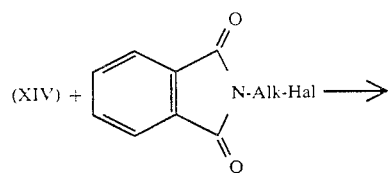

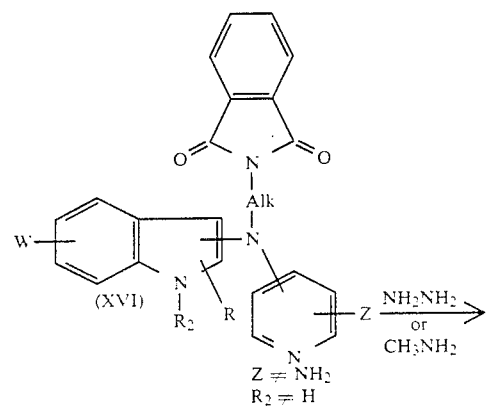

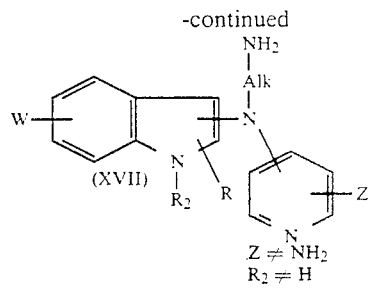

Compound XIV is allowed to react with a dihaloloweralkane of the formula Hal-Alk-Hal in a routine manner known to the art to afford a compound of Formula XVIII and thereafter the latter is allowed to react with a compound of the formula $R'NH_2$, where $R'$ is hydrogen or loweralkyl in a routine manner known to the art to afford a compound of the Formula XIX.

(XIV) $\xrightarrow{\text{Hal-Alk-Hal}}$

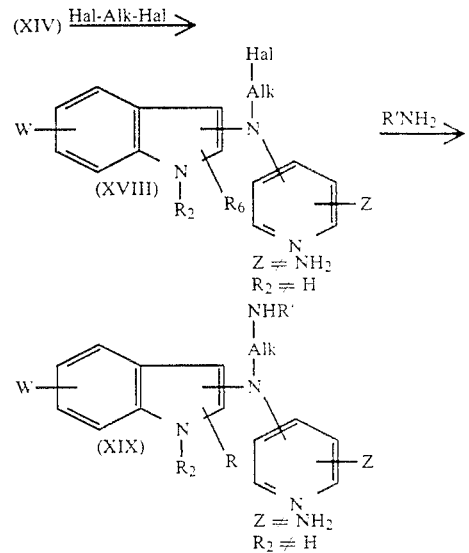

STEP F:

Compound XIV is allowed to react with an acid halide of the formula

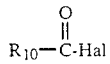

$R_{10}$—C-Hal where $R_{10}$ is loweralkyl, in a routine manner known to the art to afford a compound of Formula XX.

(XIV) + $R_{10}$—C-Hal $\longrightarrow$

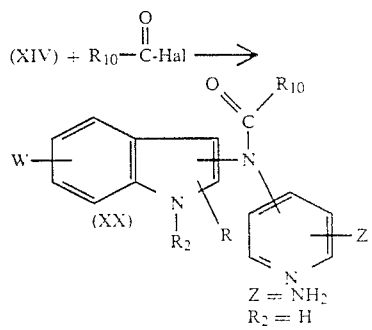

Alternatively to the above, where $R_2$ may be hydrogen or loweralkyl and where $R_{10}$ is hydrogen or loweralkyl, an acid anhydride of the formula, $R_{10}$—CO—O—CO—$R_{10}$ may be used in a routine manner known to the art to accomplish the same purpose.

Compound XIV is allowed to react with a compound of formula

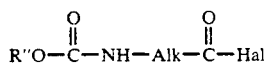

where R" is t-butyl or benzyl in a routine manner known to the art to afford a compound of Formula XXI and thereafter the latter is hydrolyzed or subjected to catalytic hydrogenolysis in a routine manner known to the art to afford a compound of the Formula XXII.

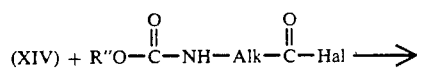

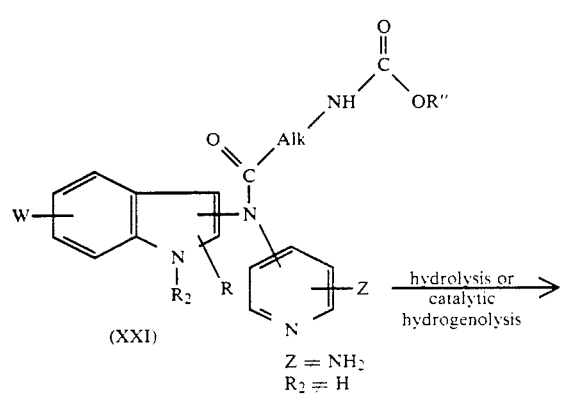

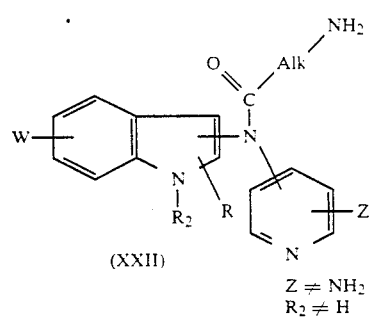

Alternatively to the above, compound XIV is allowed to react with a carboxylic acid of Formula XXIII in the presence of dicyclohexylcarbodiimide to afford compound XXI which is converted to compound XXII as described supra.

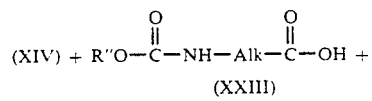

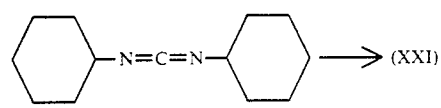

STEP G:
Compound XXa obtained from STEP F is reduced with LiAlH₄ or other suitable reducing reagents in a routine manner known to the art to afford a compound of Formula XXIV.

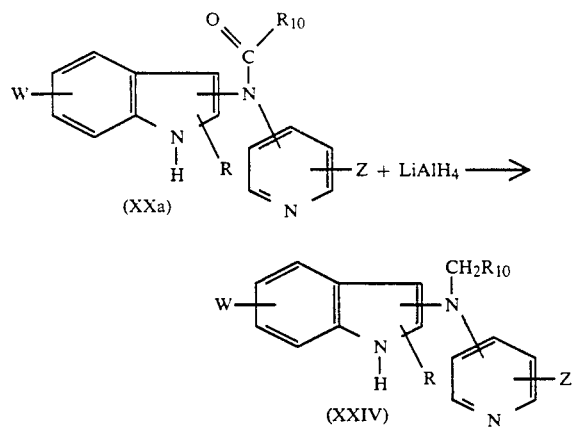

In the special case where the target compounds of Formula XXV are desired (namely where various derivatives of 3-aminoindoles in which the 2-position is unsubstituted are desired), it is convenient to utilize the reaction scheme described below as Steps H, I and J.

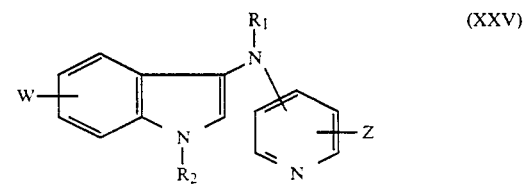

STEP H:
A 3-aminoindole of Formula XXVI where R''' is ethyl or t-butyl is prepared by the reaction sequence schematically depicted below.

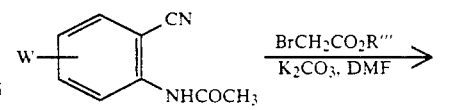

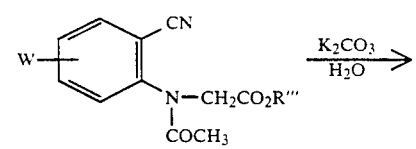

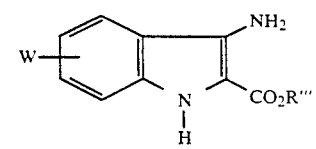

Alternatively to the above, one can also use the following reaction sequence.

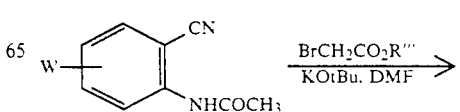

-continued

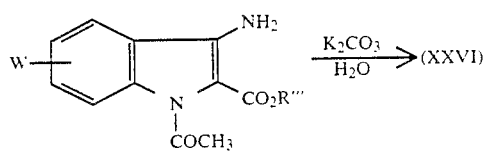

STEP I:
Compound XXVI is allowed to react with a chloropyridine hydrochloride in substantially the same manner as in STEP A to afford a compound for Formula XXVII.

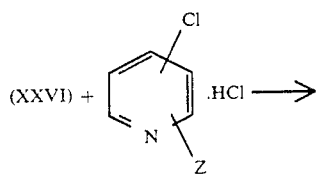

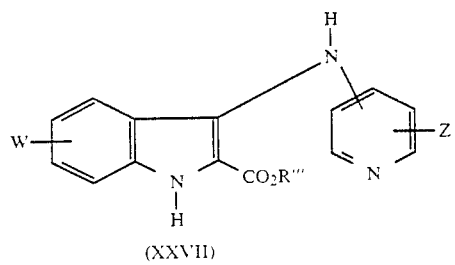

STEP j:
Compound XXVII where R''' is t-butyl in the presence of CF₃COOH is allowed to convert to a compound of Formula XXVIII.

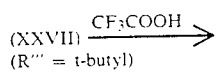

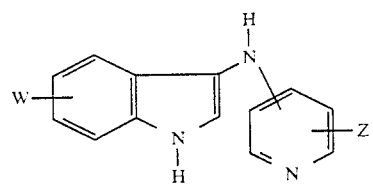

Once the compounds of Formula XXVIII are obtained, the various derivatives thereof having Formula XXV can be prepared by utilizing the various reaction steps described earlier as STEP B through G.

The starting compounds of Formula XXIX where X' is O or S which are described above are allowed to undergo various reactions in substantially the same manner as in STEPS A, B, E, F or G to afford various derivatives of Formula XXX.

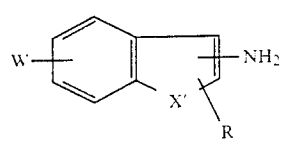

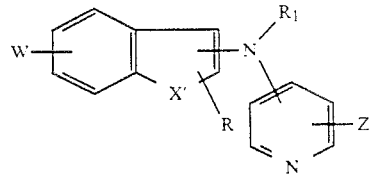

In the special case of the target compounds of Formula Id, it is expedient in this invention to use the starting compounds of Formula VI as mentioned earlier. Thus, compound VI is allowed to react with an optionally substituted chloropyridine hydrochloride in substantially the same manner as described in STEP A. The resultant product is allowed to undergo a chemical reaction as described in STEP B, E, F or G. The resultant products obtained above are allowed to undergo a suitable hydrogenation reaction whereby the nitro group is converted to an amino group. The amino group of the resultant compound is diazotized according to methods known to the art. The diazo compound is allowed to react with hypophosphorous acid to afford an unsubstituted compound. The above mentioned diazo compound is also allowed to undergo a Sandmeyer reaction to afford the corresponding chloro and bromo derivatives. In this way, various target compounds of Formula Id are obtained.

The starting compounds of Formula V described earlier are allowed to undergo various reactions in substantially the same manner as in STEPS A through G to afford various derivatives of Formula XXXI.

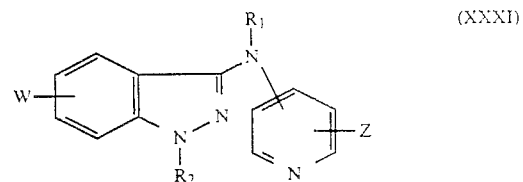

The starting compounds of Formula XXXII, where X' is O or S, (namely compounds of Formula VIII or IX described earlier) are allowed to undergo various reactions in substantially the same manner as in STEP A, B, E, F and/or G to afford various derivatives of Formula XXXIII.

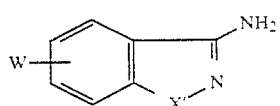

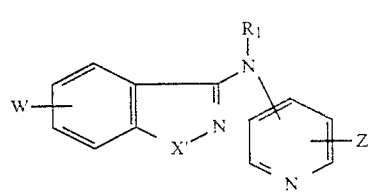

In the foregoing description of synthetic steps, where a compound in which the group —Z is —NH₂ is desired, it can be prepared by reducing the corresponding compound in which the group —Z is —NO₂ with a suitable reducing agent such as zinc and hydrochloric acid or catalytically with hydrogen and a suitable noble metal catalyst such as palladium or platinum in a routine manner known to the art.

The compounds of Formula I of the present invention are useful for the treatment of various memory dysfunctions such as Alzheimer's disease, as modulators of neurotransmitter function such as serotonergic and adrenergic, and as such are useful as antidepressants, anxiolytics, atypical antipsychotics, antiemetics, and for the treatment of personality disorders such as obsessive compulsive disorder.

Five test protocols described below, namely, (A) $5HT_{1A}$ receptor binding, (B) $5HT_3$ receptor binding, (C) Inhibition of serotonin uptake, (D) Inhibition of dopamine uptake, and (E) Inhibition of norepinephrine uptake, are used to ascertain the biological properties of the compounds of this invention.

(A)
[$^3$H]-8-Hydroxy-2-(di-n-propylamino)tetralin([$^3$H]-DPAT) Binding to Serotonin Receptors of $5HT_{1A}$ Type Purpose:

The purpose of this assay is to determine the affinity of test compounds for the $5HT_{1A}$ receptor in the brain. It is believed to be useful for predicting compounds with serotonergic properties with potential utility as novel anxiolytics (1-4), atypical antipsychotics or useful for the treatment of personality disorders such as obsessive compulsive disorder.

Introduction:

The existence of two populations of 5HT receptors in rat brain was shown by differential sensitivity to spiroperidol (5). The spiroperidol-sensitive receptors were designated as the $5HT_{1A}$ subtype and the insensitive receptors were referred to as the $5HT_{1B}$ subtype (6). Other 5HT binding sites ($5HT_{1C}$, $5HT_{1D}$ and $5HT_3$) have subsequently been identified in various species, based on differential sensitivity to 5HT antagonists (7). A significant advance in the classification of 5HT receptors came with the identification of a selective ligand for the 5 $HT_{1A}$ receptor, [$^3$H]DPAT (8). These authors reported that [$^3$H]DPAT labeled an autoreceptor. Lesion studies suggest that [$^3$H]DPAT labeled receptors are not terminal autoreceptors, but may be somatodendritic autoreceptors (9). Although DPAT decreases the firing rate in the Raphe nucleus and inhibits 5 HT release, the actual location and function is somewhat controversial (2). These studies and the sensitivity of [$^3$H]DPAT binding to guanine nucleotides and effects on adenylate cyclase suggest that DPAT acts as an agonist at the 5 $HT_{1A}$ receptor (10).

Procedure I

A. Reagents
1. Tris Buffers, pH 7.7

---

(a) 57.2 g Tris HCl
   16.2 g Tris base
   Bring volume to 1 liter with distilled water
   (0.5 M Tris buffer, pH 7.7, buffer 1 a).
(b) Make a 1:10 dilution in deionized H$_2$O (0.05 M Tris buffer, pH 7.7, buffer 1 b).
(c) 0.05 M Tris buffer, pH 7.7 containing 10 μM pargyline, 4 mM CaCl$_2$ and 0.1% ascorbic acid (buffer 1 c).
   0.49 mg pargyline.HCl
   111 mg CaCl$_2$
   250 mg ascorbic acid
   Bring to 250 ml with 0.05 M Tris buffer, pH 7.7 (reagent 1 b)

---

2. 8-Hydroxy[$^3$H]-DPAT (2-(N,N-Di[2,3(n)-$^3$H]propylamino)-8-hydroxy-1,2,3,4-tetrahydronaphthalene) (160-206 Ci/mmol) was obtained from Amersham.

For IC$_{50}$ determinations: a 10 nM stock solution is made up and 50 μl added to each tube (final concentration=0.5 nM).

3. Serotonin creatinine sulfate. 0.5 mM stock solution is made up in 0.01N HCl and 20 μl added to 3 tubes for determination of nonspecific binding (final concentration=10 μM).

4. Test Compounds. For most assays, a 1 mM stock solution is made up in a suitable solvent and serially diluted, such that the final concentration in the assay ranges from $2 \times 10^{-5}$ to $2 \times 10^{-8}$M. Seven concentrations are used for each assay. Higher or lower concentrations may be used based on the potency of the drug.

B. Tissue Preparation

Male Wistar rats are sacrificed by decapitation. Hippocampi are removed, weighed and homogenized in 20 volumes of 0.05M Tris buffer, pH 7.7. The homogenate is centrifuged at 48,000 g for 10 minutes and the supernatant is discarded. The pellet is resuspended in an equal volume of 0.05M Tris buffer, incubated at 37° C. for 10 minutes and recentrifuged at 48,000 g for 10 minutes. The final membrane pellet is resuspended in 0.05M Tris buffer containing 4 mM CaCl$_2$, 0.1% ascorbic acid and 10 μM pargyline.

C. Assay
800 μl Tissue
130 μl 0.05M Tris+CaCl$_2$+pargyline+ascorbic acid
20 μl vehicle/5 HT/drug
50 μl [$^3$H]DPAT Tubes are incubated for 15 minutes at 25° C. The assay is stopped by vacuum filtration through Whatman GF/B filters which are then washed 2 times with 5 ml of ice-cold 0.05M Tris buffer. The filters are then placed into scintillation vials with 10 ml of Liquiscint scintillation cocktail and counted.

Calculation

Specific binding is defined as the difference between total binding and binding in the presence of 10 μM 5 HT. IC$_{50}$ values are calculated from the percent specific binding at each drug concentration.

Procedure II

A. Reagents
1. Tris Buffers, pH 7.7

---

(a) 57.2 g Tris HCl
   16.2 g Tris base
   Bring to 1 liter with distilled water
   (0.5 M Tris buffer, pH 7.7, buffer 1 a).
(b) Make a 1:10 dilution in distilled H$_2$O (0.05 M Tris buffer, pH 7.7 at 25° C., buffer 1 b).
(c) 0.05 M Tris buffer, pH 7.7 containing 10 μM pargyline, 4 mM CaCl$_2$ and 0.1% ascorbic acid (buffer 1 c).
   0.49 mg pargyline.HCl
   110.99 mg CaCl$_2$
   250 mg ascorbic acid
   Bring to 250 ml with 0.05 M Tris buffer, pH 7.7 (buffer 1 b).

---

2. 8-Hydroxy[$^3$H]-DPAT (2-(N,N-Di[2,3(n)-$^3$H]propylamino)-8-hydroxy-1,2,3,4-tetrahydronaphthalene)](160-206 Ci/mmol) was obtained from Amersham.

For IC$_{50}$ determinations: [$^3$H]-DPAT is made up to a concentration of 3.3 nM in the Tris Buffer (1c) such that when 150 μl is added to each tube a final concentration of 0.5 nM is attained in the 1 ml assay.

3. Serotonin creatinine sulfate is obtained from the Sigma Chemical Company. Serotonin creatinine is made up to a concentration of 100 μM in Tris buffer (1c). One hundred μl is added to each of 3 tubes for the determination of nonspecific binding (this yields a final concentration of 10 μM in the 1 ml assay).

4. Test Compounds. For most assays, a 100 μM stock solution is made up in a suitable solvent and serially diluted with Tris buffer (1c) such that when 100 μl of drug is combined with the total 1 ml assay, a final concentration ranging from $10^{-5}$ to $10^{-8}$M is attained. Characteristically seven concentrations are studied for each assay; however, higher or lower concentrations may be used, depending on the potency of the drug.

B. Tissue Preparation

Male Wistar rats are decapitated, the hippocampi are removed and homogenized in 20 volumes of ice cold 0.05M Tris buffer, pH 7.7 (1b). The homogenate is centrifuged at 48,000 g for 10 minutes at 4° C. The resulting pellet is rehomogenized in fresh Tris buffer (1b), incubated at 37° C. for 10 minutes and recentrifuged at 48,000 g for 10 minutes. The final membrane pellet is resuspended in 0.05M Tris buffer (1c) containing 4 mM $CaCl_2$, 0.1% ascorbic acid and 10 μM pargyline. Specific binding is approximately 90% of total bound ligand.

C. Assay

| 750 μl | Tissue |
| 150 μl | [$^3$H]DPAT |
| 100 μl | vehicle (for total binding) or 100 μM serotonin creatinine sulfate (for nonspecific binding) or appropriate drug concentration |

Tubes are incubated for 15 minutes at 25° C. The assay is stopped by vacuum filtration through Whatman GF/B filters which are then washed 2 times with 5 ml of ice-cold 0.05M Tris buffer (1b). The filters are then placed into scintillation vials with 10 ml of Liquiscint scintillation cocktail and counted. Specific binding is defined as the difference between total binding in the absence or presence of 10 μM serotonin creatinine sulfate. $IC_{50}$ values are calculated from the percent specific binding at each drug concentration.

The $K_D$ value for [$^3$H]DPAT binding was found to be 1.3 nM by Scatchard analysis of a receptor saturation experiment. The $K_i$ value may then be calculated by the Cheng-Prusoff equation:

$$K_i = IC_{50}/1 + L/K_D$$

References

1. Dourish C. T., Hutson, P. H. and Curzon, G.: Putative anxiolytics 8-OH-DPAT, buspirone and TVX Q 7821 are agonists at 5 $HT_{1A}$ autoreceptors in the raphe nucleus. TIPS 7: 212–214 (1986).
2. Verge, D., Daval, G., Marcinkiewicz, M., Patey, A., El Mestikawy, H. Gozlan and Hamon, M.: Quantitative autoradiography of multiple 5-$HT_1$ receptor subtypes in the brain of control or 5,7-dihydroxytryptamine-treated rats. J. Neurosci. 6: 3474–3482 (1986).
3. Iversen, S. D.: 5 HT and anxiety. Neuropharmacol. 23: 1553–1560 (1984).
4. Traber J. and Glaser, T.: 5 $HT_{1A}$ receptor-related anxiolytics. TIPS 8: 432–437 (1987).
5. Pedigo, N. W., Yammamura, H. I. and Nelson, D. L.: Discrimination of multiple [$^3$H]5-hydroxytryptamine binding sites by the neuroleptic spiperone in rat brain. J. Neurochem. 36: 220–226 (1981).
6. Middlemiss, D. N. and Fozard, J. R.: 8-Hydroxy-2-(di-n-propylamino)tetralin discriminates between subtypes of the 5 $HT_1$ recognition site. Eur. J. Pharmacol., 90: 151–152 (1983).
7. Peroutka, S. J.: Pharmacological differentiation and characterization of 5-$HT_{1A}$, 5-$HT_{1B}$ and 5-$HT_{1C}$ binding sites in rat frontal cortex. J. Neurochem. 47: 529–540 (1986).
8. Peroutka, S. J.: 5-Hydroxytryptamine receptor subtypes: molecular, biochemical and physiological characterization. TINS 11: 496–500 (1988).
9. Gozlan, H., El Mestikawy, S., Pichat, L. Glowinsky, J. and Hamon, M.: Identification of presynaptic serotonin autoreceptors using a new ligand: [$^3$H]-DPAT. Nature 305: 140–142 (1983).
10. Schlegel, R. and Peroutka, S. J.: Nucleotide interactions with 5-$HT_{1A}$ binding sites directly labeled by [$^3$H]-8-hydroxy-2-(di-n-propylamino)tetralin ([$^3$H]-8-OH-DPAT). Biochem. Pharmacol. 35 1943–1949 (1986).
11. Peroutka, S. J.: Selective interaction of novel anxiolytics with 5-hydroxytryptamine$_{1A}$ receptors. Biol. Psychiatry. 20: 971–979 (1985).

(B) $^3$H-GR 65630 Binding to Serotonin Receptors of 5 $HT_3$ Type

Purpose:

The purpose of this assay is to determine the affinity of test compounds for the 5 $HT_3$ binding site in the brain. This is believed to be useful for predicting the potential of compounds to exhibit antiemetic, anxiolytic or atypical antipsychotic profiles.

Introduction:

Presently, it is generally accepted that there are three different receptor subtypes for the neurotransmitter serotonin (5 HT); 5 $HT_1$, 5 $HT_2$ and 5 $HT_3$. The 5 $HT_1$ and 5 $HT_2$ binding sites have been well characterized and further subdivided based on data from binding and functional activity studies (1,2). The 5 $HT_3$ binding site, on the other hand, has only recently begun to be characterized. Originally it was believed that 5 $HT_3$ binding sites existed only in the periphery (3). However, with the recent introduction of potent and selective 5 $HT_3$ antagonist drugs such as GR65630, zacopride, ICS 205 930 and MDL 72222, data from binding studies have indicated that 5 $HT_3$ binding sites are also located in select areas of the brain (4,5,6). The highest levels of 5 $HT_3$ binding sites have been detected in limbic and dopamine containing brain areas (entorhinal cortex, amygdala, nucleus accumbens and tuberculum olfactorium) (4). Besides possessing selective binding in dopamine rich areas, 5 $HT_3$ antagonists have been reported to block behavioral effects associated with certain drugs of abuse (nicotine and morphine) and to be active in behavioral tests predictive of anxiolytic activity. Based on these selective regional binding results and behavioral studies, it has been speculated that 5 $HT_3$ antagonists may have a therapeutic benefit in disease states believed to be associated with excessive dopaminergic activity; e.g., schizophrenia and drug abuse.

Procedure

A. Reagents 1. 0.05 M Krebs-Hepes buffer, pH 7.4
   11.92 g Hepes
   10.52 g NaCl
   0.373 g KCl
   0.277 g $CaCl_2$
   0.244 g $MgCl_2 \cdot 6H_2O$
   Bring to 1 liter with distilled $H_2O$.
   Bring pH up to 7.4 (at 4° C.) with 5N NaOH.

2. [$^3$H]-GR65630 (87.0 Ci/mmol) is obtained from New England Nuclear. For $IC_{50}$ determinations: [$^3$H]-GR65630 is made up to a concentration of 1.0 nM in Krebs-Hepes buffer such that when 100 μl is added to each tube a final concentration of 0.4 nM is attained in the 250 μl assay.

3. Zacopride maleate is obtained from Research Biochemicals Inc. Zacopride maleate is made up to a concentration of 500 μM in Krebs-Hepes buffer. 50 μl is added to each of 3 tubes for the determination of nonspecific binding (yields a final concentration of 100 μM in the 250 μl assay).

4. Test Compounds: For most assays, a 50 μM stock solution is made up in a suitable solvent and serially diluted with Krebs-Hepes buffer such that when 50 μl of drug is combined with the total 250 μl assay, a final concentration from $10^{-5}$ to $10^{-8}$ is attained. Characteristically seven concentrations are studied for each assay; however, higher or lower concentrations may be used, depending on the potency of the drug.

B. Tissue Preparation

Male Wistar rats (150-200 g) are decapitated, the entorhinal cortex removed, weighed and homogenized in 10 volumes of ice-cold 0.05M Krebs-Hepes buffer, pH 7.4. The homogenate is centrifuged at 48,000 g for 15 minutes at 4° C. The resulting pellet is rehomogenized in fresh Krebs-Hepes buffer and recentrifuged at 48,000 g for 15 minutes at 4° C. The final pellet is resuspended in the original volume of ice-cold Krebs-Hepes buffer. This yields a final tissue concentration of 1.2-1.6 mg/ml with the addition of 100 μl to the assay. Specific binding is approximately 55-65% of total bound ligand.

C. Assay

| | |
|---|---|
| 100 μl | Tissue suspension |
| 100 μl | [$^3$H]-Gr65630 |
| 50 μl | Vehicle (for total binding) or 500 μM Zacopride maleate (for nonspecific binding) or appropriate drug concentration |

Sample tubes are kept on ice for additions, then vortexed and incubated with continuous shaking for 30 minutes at 37° C. At the end of the incubation period, the incubate is diluted with 5 ml of ice-cold Krebs-Hepes buffer and immediately vacuum filtered through Whatman GF/B filters, followed by two 5-ml washes with ice-cold Krebs-Hepes buffer. The filters are dried and counted in 10 ml of liquid scintillation cocktail. Specific GR65630 binding is defined as the difference between the total binding and that bound in the presence of 100 μM Zacopride. $IC_{50}$ calculations are performed using computer-derived log-probit analysis.

References

1. Peroutka, S. J. 5-Hydroxytryptamine receptor subtypes: Molecular biochemical and physiological characterization. Trends In Neuroscience 11: 496-500 (1988).
2. Walting, K. J. 5 $HT_3$ receptor agonists and antagonists. Neurotransmission 3: 1-4 (1989).
3. Costell, B., Naylor, R. J. and Tyers, M. B. Recent advances in the neuropharmacology of 5 $HT_3$ agonists and antagonists. Rev. Neuroscience 2: 41-65 (1988).
4. Kilpatrick, G. J., Jones, B. P. and Tyers, M. B. Identification and distribution of 5 $HT_3$ receptors in rat brain using radioligand binding. Nature 330: 746-748 (1987).
5. Barnes, N. M., Costell, B. and Naylor, R. J. [$^3$H] Zacopride: Ligand for the identification of 5 $HT_3$ recognition sites. J. Pharm. Pharmacol. 40: 548-551 (1988).
6. Watling, K. J., Aspley, S., Swain, C. J. and Saunders, J. [$^3$H] Quaternised ICS 205-930 labels 5 $HT_3$ receptor binding sites in rat brain. Eur. J. Pharmacol. 149: 397-398 (1988).

(C) Inhibition of [$^3$H]-Serotonin Uptake in Rat Whole Brain Synaptosomes

Purpose:

This assay is used as a biochemical screen for compounds which block serotonin (5 HT) uptake, which may be useful as antidepressants and for the treatment of personality disorders such as obsessive compulsive disorder.

Introduction:

Asberg and coworkers have suggested that subjects with serotonergic hypofunction comprise a biochemical subgroup of depressed patients (1), while others (2) claim that altered serotonergic function determines the mood changes associated with affective disorders. Although the role of 5 HT in the etiology of depression is not clear; it is true that a number of antidepressant drugs block the 5 HT reuptake mechanism. In vitro receptor binding assays have shown that [$^3$H]-imipramine labels 5 HT uptakes sites (10). Trazodone and zimelidine are clinically effective antidepressants (3) with fairly selective effects on 5 HT uptake (4,5). More recently, fluoxetine has been shown to be both a selective and potent 5 HT uptake inhibitor.

[$^3$H]-5 HT transport has been characterized in CNS tissue (6,7) and found to be saturable, sodium- and temperature-dependent, inhibited by ouabain, metabolic inhibitors, tryptamine analogs (8) and tricyclic antidepressants (tertiary amines >>secondary amines) (9). The latter findings differentiate 5 HT uptake from catecholamine uptake. [$^3$H]-5 HT uptake can also be used as a marker for serotonin nerve terminals.

Procedure

A. Animals: Male CR Wistar rats (100-125 g).

B. Reagents-

1. Krebs-Henseleit Bicarbonate Buffer, pH 7.4 (KHBB): Make a 1 liter batch, containing the following salts.

| | g/L | mM |
|---|---|---|
| NaCl | 6.92 | 118.4 |
| KCl | 0.35 | 4.7 |
| $MgSO_4 \cdot 7H_2O$ | 0.29 | 1.2 |
| $KH_2PO_4$ | 0.16 | 2.2 |
| $NaHCO_3$ | 2.10 | 24.9 |
| $CaCl_2$ | 0.14 | 1.3 |

-continued

|  | g/L | mM |
|---|---|---|
| Prior to use add: | | |
| Dextrose | 2 mg/ml | 11.1 |
| Iproniazid phosphate | 0.30 mg/ml | 0.1 |

Aerate for 60 min. with 95% $O_2$/5% $CO_2$, check pH (7.4±0.1)

2. 0.32M Sucrose: 21.9 g of sucrose, bring to 200 ml.

3. Serotonin creatinine $SO_4$ is obtained from Sigma Chemical Co. A 0.1 mM stock solution is made up in 0.01N HCl. This is used to dilute the specific activity of radiolabeled 5 HT.

4. 5-[1,2-$^3$H(N)]-Hydroxytryptamine creatinine sulfate (Serotonin), specific activity 20-30 Ci/mmol is obtained from New England Nuclear.

The final desired concentration of $^3$H-5 HT in the assay is 50 nM. The dilution factor is 0.8. Therefore, the KHBB is made up to contain 62.5 nM [$^3$H]-5 HT.

Add to 100 ml of KHBB.

| A) 56.1 μl of 0.1 mM 5HT = | 56.1 nM |
|---|---|
| *B) 0.64 nmole of $^3$H-5Ht = | 6.4 nM |
| | 62.5 nM |

*Calculate volume added from specific activity of $^3$H-5HT.

5. For most assays, a 1 mM solution of the test compound is made up in suitable solvent and serially diluted such that the final concentration in the assay ranges from $2 \times 10^{-8}$ to $2 \times 10^{-5}$M. Seven concentrations are used for each assay. Higher or lower concentrations may be used depending on the potency of the compound.

C. Tissue Preparation

Male Wistar rats are decapitated and the brain rapidly removed. Whole brain minus cerebella is weighed and homogenized in 9 volumes of ice-cold 0.32M sucrose using a Potter-Elvejhem homogenizer. Homogenization should be done with 4-5 up and down strokes at medium speeds to minimize synaptosome lysis. The homogenate is centrifuged at 1000 g for 10 min. at 0°-4° C. The supernatant ($S_1$) is decanted and is used for uptake experiments.

D. Assay-

800 μl KHBB+[$^3$H]-5 HT

20 μl Vehicle or appropriate drug concentration

200 μl Tissue suspension

Tubes are incubated at 37° C. under a 95% $O_2$/5% $CO_2$ atmosphere for 5 minutes. For each assay, 3 tubes are incubated with 20 μl of vehicle at 0° C. in an ice bath. After incubation all tubes are immediately centrifuged at 4000 g for 10 minutes. The supernatant fluid is aspirated and the pellets dissolved by adding 1 ml of solubilizer (Triton X-100+50% EtOH, 1:4 v/v). The tubes are vigorously vortexed, decanted into scintillation vials, and counted in 10 ml of Liquiscint scintillation counting cocktail. Active uptake is the difference between cpm at 37° C. and 0° C. The percent inhibition at each drug concentration is the mean of three determinations. $IC_{50}$ values are derived from log-probit analysis.

References

1. Asberg, M., Thoren, P., Traskman, L., Bertilsson, L., and Ringberger, V. Serotonin depression: A biochemical subgroup within the affective disorders. Science 191: 478-480 (1975).

2. DeMontigy, C. Enhancement of 5 HT neurotransmission by antidepressant treatments. J. Physiol. (Paris) 77: 455-461 (1980).

3. Feighner, J. P. Clinical efficacy of the newer antidepressants. J. Clin. Psychopharmacol. 1: 235-265 (1981).

4. Ogren, S. O., Ross, S. B., Hall, H., Holm, A. C. and Renyi, A. L. The pharmacology of zimelidine: A 5 HT selective reuptake inhibitor. Acta Psychiat. Scand. 290: 127-151 (1981).

5. Clements-Jewry, S., Robson, P. A. and Chidley, L. J. Biochemical investigations into the mode of action of trazodone. Neuropharmacol. 19: 1165-1173 (1980).

6. Ross, S. B. Neuronal transport of 5-hydroxytryptamine. Pharmacol. 21: 123-131 (1980).

7. Shaskan, E. G. and Snyder, S. H. Kinetics of serotonin accumulation into slices from rat brain: Relationship to catecholamine uptake. J. Pharmacol. Exp. Ther. 175: 404-418 (1970).

8. Horn, S. A. Structure-activity relations for the inhibition of 5 HT uptake into rat hypothalamic homogenates by serotonin and tryptamine analogues. J. Neurochem. 21: 883-888 (1973).

9. Horn, A. S. and Trace, R. C. A. M. Structure-activity relations for the inhibition of 5-hydroxytryptamine uptake by tricyclic antidepressant into synaptosomes from serotonergic neurones in rat brain homogenates. Brit. J. Pharmacol. 51: 399-403 (1974).

10. Langer, S. Z., Moret, C., Raisman, R., Dubocovich, M. L. and Briley M. High affinity [$^3$H]imipramine binding in rat hypothalamus: Association with uptake of serotonin but not norepinephrine. Science 210: 1133-1135 (1980).

(D) Inhibition of $^3$H-Dopamine Uptake in Rat Striatal Synaptosomes

Purpose

This assay is used to show differential drug effects on dopamine uptake versus norepinephrine uptake and to identify therapeutic agents for diseases where the potentiation of dopaminergic activity may be helpful (e.g. Parkinson's Disease).

Introduction

High-affinity, saturable, temperature and sodium-dependent transport of $^3$H-DA has been observed in tissue preparations from various brain regions (1,2). $^3$H-DA uptake is potently inhibited by cocaine, phenethylamines and ouabain, but, unlike NE, it is not potently inhibited by the tricyclic antidepressants (3). The only antidepressants which inhibit DA uptake are nomifensine (4) and bupropion (5). The relationship of DA uptake to the efficacy of these compounds is unknown. Coyle and Snyder (6) reported no stereoselectivity for the inhibition of DA uptake by d- or l-amphetamine but conformational selectivity (gauche>anti) has been shown by other investigators (7).

Several authors have shown that at least part of the effect of $^3$H-amine accumulation by some compounds is due to direct releasing activity (4,8,9). However, there are some discrepancies in these reports. In order to differentiate the effects on uptake from the effects on release, the direct releasing effects must be determined in separate experiments. The most reliable method for determining neurotransmitter release is by a superfusion technique described by Raiteri et al. (10). This is a theoretical concern for studying the uptake of any substance in vitro, but is emphasized for dopamine uptake.

$^3$H-DA uptake may also be used as a biochemical marker for dopaminergic nerve terminals, especially in conjunction with lesioning experiments.

Procedure

A. Animals: Male CR Wistar rats (100–125 g).
B. Reagents-
1. Krebs-Henseleit Bicarbonate Buffer, pH 7.4 (KHBB): Make a 1 liter batch containing the following salts.

|  | g/L | mM |
|---|---|---|
| NaCl | 6.92 | 118.4 |
| KCl | 0.35 | 4.7 |
| MgSO$_4$.7H$_2$O | 0.29 | 1.2 |
| KH$_2$PO$_4$ | 0.16 | 2.2 |
| NaHCO$_3$ | 2.10 | 24.9 |
| CaCl$_2$ | 0.14 | 1.3 |
| Prior to use add: |  |  |
| Dextrose | 2 mg/ml | 11.1 mM |
| Iproniazid phosphate | 0.30 mg/ml | 0.1 mM |

Aerate for 60 min. with 95% O$_2$/5% CO$_2$, check pH (7.4±0.1)

2. 0.32M Sucrose: 21.9 g of sucrose, bring to 200 ml.
3. Dopamine HCl is obtained from Sigma Chemical Company. A 0.1 mM stock solution is made up in 0.01N HCl. This is used to dilute the specific activity of the radiolabeled DA.
4. 3,4-[8-$^3$H(N)]-Dihydroxyphenylethylamine (Dopamine), specific activity 4–34 Ci/mmol is obtained from New England Nuclear.

The final desired concentration of $^3$H-DA in the assay is 50 nM. The dilution factor is 0.9. Therefore, the KHBB is made up to contain 55.5 nM [$^3$H]-5 DA.
Add to 100 ml of KHBB.

| A) 50 μl of 0.1 mM DA = | 50 nM |
|---|---|
| *B) 0.55 nmoles of $^3$HDA = | 5.5 nM |
|  | 55.5 nM |

Calculate volume added from specific activity of $^3$H-DA.

5. For most assays, a 1 mM stock solution of the test compound is made up in a suitable solvent and serially diluted such that the final concentration in the assay ranges from 2×10$^{-8}$ to 2×10$^{-5}$M. Seven concentrations are used for each assay. Higher or lower concentrations may be used depending on the potency of the compound.

C. Tissue Preparation

Male Wistar rats are decapitated and the brain rapidly removed. Corpora striata are rapidly removed, weighed and homogenized in 9 volumes of ice-cold 0.32M sucrose using a Potter-Elvejhem homogenizer. Homogenization should be done with 4–5 up and down strokes at medium speeds to minimize synaptosome lysis. The homogenate is centrifuged at 1000 g for 10 min. at 0°–4° C. The supernatant (S$_1$) is decanted and is used for uptake experiments.

D. Assay
900 μl KHBB [$^3$H]-DA
20 μl Vehicle or appropriate drug concentration
100 μl Tissue suspension Tubes are incubated at 37° C. under a 95% O$_2$/5% CO$_2$ atmosphere for 5 minutes. For each assay, 3 tubes are incubated with 20 μl of vehicle at 0° C. in an ice bath. After incubation all tubes are immediately centrifuged at 4000 g for 10 minutes. The supernatant fluid is aspirated and the pellets dissolved by adding 1 ml of solubilizer (Triton X-100+50% EtOH, 1:4 v/v). The tubes are vigorously vortexed, decanted into scintillation vials, and counted in 10 ml of Liquiscint scintillation counting cocktail. Active uptake is the difference between cpm at 37° C. and 0° C. The percent inhibition at each drug concentration is the mean of three determinations. IC$_{50}$ values are derived from log-probit analysis.

References

1. Snyder, S. H. and Coyle, J. T., "Regional differences in [$^3$H]-norepinephrine and [$^3$H]-dopamine uptake into rat brain homogenates." J. Pharmacol. Exp. Ther. 165: 78–86 (1969).
2. Holz, R. W. and Coyle, J. T., "The effects of various salts, temperature and the alkaloids veratridine and batrachotoxin on the uptake of [$^3$H]-dopamine into synaptosomes from rat brain." Mol. Pharmacol. 10: 746–758 (1974).
3. Horn, A. S., Coyle, J. T. and Snyder, S. H., "Catecholamine uptake by synaptosomes from rat brain: Structure-activity relationships of drugs with differential effects on dopamine and norepinephrine neurons." Mol. Pharmacol. 7: 66–80 (1970).
4. Hunt, R., Raynaud, J. P., Leven, M. and Schacht, U., "Dopamine uptake inhibitors and releasing agents differentiated by the use of synaptosomes and field stimulated brain slices." Biochem. Pharmacol. 28: 2011–2016 (1979).
5. Cooper, B. R., Hester, T. J. and Maxwell, R. A., "Behavioral and biochemical effects of the antidepressant bupropion (Wellbutrin): Evidence for selective blockade of dopamine uptake in vivo." J. Pharmacol. Exp. Ther. 215: 127–134 (1980).
6. Coyle, J. T. and Snyder, S. H., "Catecholamine uptake by synaptosomes in homogenates of rat brain: Stereospecificity in different areas." J. Pharmacol. Exp. Ther. 170: 221–231 (1969).
7. Tuomisto, L., Tuomisto, J. and Smissman, E. E., "Dopamine uptake in striatal and hypothalamic synaptosomes: Conformational selectivity of the inhibition." Eur. J. Pharmacol. 25: 351–361 (1974).
8. Heikkila, R. E., Orlansky, H. and Cohen, G., "Studies on the distinction between uptake inhibition and release of [$^3$H]-dopamine in rat brain tissue slices." Biochem. Pharmacol. 24: 847–852 (1975).
9. Baumann, P. A. and Maitre, L., "Is drug inhibition of dopamine uptake a misinterpretation of in vitro experiments!" Nature 264: 789–790 (1976).
10. Raiteri, M., Angelini, F. and Levi, G., "A simple apparatus for studying the release of neurotransmitters from synaptosomes." Eur J. Pharmacol. 25: 411–414 (1974).

(E) Inhibition of [$^3$H]-Norepinephrine Uptake in Rat Whole Brain or Hypothalamic Synaptosomes Purpose:
This assay is used as a biochemical screen for potential antidepressants which block norepinephrine uptake.
Introduction:
The neuronal re-uptake mechanism for norepinephrine (NE) is the most important physiological means for inactivating NE by removing the transmitter from the synaptic cleft (1). NE uptake is accomplished by a saturable, stereospecific, high-affinity ($K_m = 10^{-7} - 10^{-6}M$), sodium dependent, active transport system, which has been shown to exist in both peripheral and central nervous system tissue, using slice, homogenate and purified synaptosome preparations (2). NE uptake is potently inhibited by cocaine, phenethylamines and tricyclic antidepressants (3). It is also inhibited by ouabain, metabolic inhibitors and phenoxybenzamine. The inhibition of NE uptake by clinically effective tricyclic antidepressants is an important link in the catecholamine hypothesis of affective disorders (4). In this series of compounds, the secondary amines (e.g. desipramine) are more active than the tertiary amines (e.g. imipramine). Extensive structure activity relationships for NE uptake have been studied in the past (5,6).

There are large regional variations in NE uptake (7-9) which correlate with the endogenous levels of NE. The hypothalamus shows the highest level of NE and the greatest uptake. This region is used for further testing of compounds showing activity in whole brain preparations.

Synaptosomal [$^3H$]-NE uptake is a useful marker for the integrity of noreadrenergic neurons after lesioning experiments, as well as an assay for compounds which potentiate the action of NE by blocking the reuptake mechanism.

Procedure

A. Animals: Male CR Wistar rats (100–125 g).
B. Reagents-
1. Krebs-Henseleit Bicarbonate Buffer, pH 7.4 (KHBB): Make a 1 liter batch, containing the following salts.

|  | g/L | mM |
|---|---|---|
| NaCl | 6.92 | 118.4 |
| KCl | 0.35 | 4.7 |
| $MgSO_4.7H_2O$ | 0.29 | 2.2 |
| $NHCO_3$ | 2.10 | 24.9 |
| $CaCl_2$ | 0.14 | 1.3 |
| Prior to use add: |  |  |
| Dextrose | 2 mg/ml | 11.1 mM |
| Iproniazid phosphate | 0.30 mg/ml | 0.1 mM |

Aerate for 60 min. with 95% $O_2$/5% $CO_2$, check pH (7.4±0.1)
2. 0.32M Sucrose: 21.9 g of sucrose, bring to 200 ml.
3. L(—)-Norepinephrine bitartrate is obtained from Sigma Chemical Co. A 0.1 mM stock solution is made up in 0.01N HCl. This is used to dilute the specific activity of the radiolabeled NE.
4. Levo-[Ring-2,5,6-$^3H$]-Norepinephrine (40–50 Ci/mmol) is obtained from New England Nuclear.

The final desired concentration of [$^3H$]-NE in the assay is 50 nM. The dilution factor is 0.8. Therefore, the KHBB is made up to contain 62.5 nM [$^3H$]-NE.
Add to 100 ml of KHBB.

| A) 59.4 µl of 0.1 mM NE = | 59.4 nM |
| *B) 0.31 nmoles of [$^3H$]-NE = | 3.1 nM |
|  | 55.5 nM |

*Calculate volume added from specific activity of [$^3H$]-NE.

5. For most assays, a 1 mM stock solution of the test compound is made up in a suitable solvent and serially diluted such that the final concentration in the assay ranges from $2 \times 10^{-8}$ to $2 \times 10^{-5}M$. Seven concentrations are used for each assay. Higher or lower concentrations may be used depending on the potency of the compound.

C. Tissue Preparation

Male Wistar rats are decapitated and the brain rapidly removed. Either whole brain minus cerebella or hypothalamus is weighed and homogenized in 9 volumes of ice-cold 0.32M sucrose using a Potter-Elvejhem homogenizer. Homogenization should be done with 4–5 up and down strokes at medium speeds to minimize synaptosome lysis. The homogenate is centrifuged at 1000 g for 10 min. at 0°–4° C. The supernatant ($S_1$) is decanted and is used for uptake experiments.

D. Assay-
800 µl KHBB [$^3H$]-NE
20 µl Vehicle or appropriate drug concentration
200 µl Tissue suspension Tubes are incubated at 37° C. under a 95% $O_2$/5% $CO_2$ atmosphere for 5 minutes. For each assay, 3 tubes are incubated with 20 µl of vehicle at 0° C. in an ice bath. After incubation all tubes are immediately centrifuged at 4000 g for 10 minutes. The supernatant fluid is aspirated and the pellets dissolved by adding 1 ml of solubilizer (Triton X-100+50% EtOH, 1:4 v/v). The tubes are vigorously vortexed, decanted into scintillation vials, and counted in 10 ml of Liquiscint scintillation counting cocktail. Active uptake is the difference between cpm at 37° C. and 0° C. The percent inhibition at each drug concentration is the mean of three determinations. $IC_{50}$ values are derived from log-probit analysis.

References

1. Hertting, G. and Axelrod, J., "Fate of tritiated noradrenaline at the sympathetic nerve-endings." Nature 192: 172-173 (1961).
2. Paton, D. M., "Neuronal transport of norepinephrine and dopamines." Pharmacol. 21: 85-92 (1980).
3. Iversen, L. L., "Uptake mechanisms for neurotransmitter amines." Biochem. Pharmacol. 23: 1927-1934 (1974).
4. Schildkraut, J. J. "The catecholamine hypothesis of affective disorders, a review of the supporting evidence." Am. J. Psychiat. 122: 509-522 (1965).
5. Horn, A. S., Coyle, J. T. and Snyder, S. H., "Catecholamine uptake by synaptosomes from rat brain: Structure-activity relationships for drugs with differential effects in dopamine and norepinephrine neurons." Mol. Pharmacol. 7: 66-80 (1971).
6. Maxwell, R. A., Ferris, R. M., Burcsu, J., Woodward, E. C., Tang D. and Willard, K., "The phenyl rings of tricyclic antidepressants and related compounds as determinants of the potency of inhibition of the amine pumps in adrenergic neurons of the rabbit aorta and in rat cortical synaptosomes." J. Pharmacol. Exp. Ther. 191: 418-430 (1974).
7. Glowinski, J. and Iversen, L. L., "Regional studies of catecholamines in rat brain." J. Neurochem. 13: 655-669 (1966).
8. Snyder, S. H. and Coyle, J. T., "Regional differences in [$^3H$]-norepinephrine and [$^3H$]-dopamine uptake into rat brain homogenates." J. Pharmacol. Exp. Ther. 165: 78-86 (1969).
9. Snyder, S. H., Green, A. I. and Hendley, E. D., "Kinetics of [$^3H$]-norepinephrine accumulations into slices from different regions of rat brain." J. Pharmacol. Exp. Ther. 164: 90-102 (1968).

Results of the five test procedures described above (Protocols A through E) are presented in Table 1 for some of the compounds of this invention.

TABLE 1

| Compound | A | B | C | D | E |
|---|---|---|---|---|---|
| 3-(4-pyridinylamino)-1H-indole | 6.4 | 5.5 | 14.5 | | 1.0 |
| 6-Chloro-3-(propyl-4-pyridinylamino)benzo[b]thiophene hydrochloride | | 2.6 | 0.06 | 0.56 | 0.21 |
| 2-(methyl-4-pyridinyl-aminobenzo[b]thiophene hydrochloride | | | 1.15 | 0.51 | 0.078 |
| 6-Chloro-3[(cyclopropylmethyl)(4-pyridyl)amino]benzo[b]thiophene hydrochloride | | | 0.12 | | 0.012 |
| 2-(propyl-4-pyridinyl-aminobenzo[b]thiophene hydrochloride | | | 0.24 | 0.091 | 0.055 |
| 6-Chloro-3-[2-propenyl)(4-pyridyl)amino]benzo[b]thiophene hydrochloride | | | 0.12 | | 0.007 |
| Buspirone | 0.62 | | >20 | >20 | >20 |
| MDL 72222 | | 0.53 | | | |
| Clozapine | 0.58 | 1.02 | >20 | >20 | >20 |
| Chloripramine | | | 0.15 | >20 | 18.6 |
| Amitriptyline | | | 0.83 | >20 | 7.7 |

A: 5HT$_{1A}$ receptor binding. IC$_{50}$($\mu$M)
B: 5HT$_3$ receptor binding. IC$_{50}$($\mu$M)
C: Inhibition of serotonin uptake. IC$_{50}$($\mu$M)
D: Inhibition of dopamine uptake. IC$_{50}$($\mu$M)
E: Inhibition of norepinephrine uptake. IC$_{50}$($\mu$M)

This utility is further demonstrated by the ability of these compounds to restore cholinergically deficient memory in the Dark Avoidance Assay described below.

Dark Avoidance Assay

In this assay mice are tested for their ability to remember an unpleasant stimulus for a period of 24 hours. A mouse is placed in a chamber that contains a dark compartment; a strong incandescent light drives it to the dark compartment, where an electric shock is administered through metal plates on the floor. The animal is removed from the testing apparatus and tested again, 24 hours later, for the ability to remember the electric shock.

If scopolamine, an anticholinergic agent that is known to cause memory impairment, is administered before an animal's initial exposure to the test chamber, the animal re-enters the dark compartment shortly after being placed in the test chamber 24 hours later. This effect of scopolamine is blocked by an active test compound, resulting in a greater interval before re-entry into the dark compartment.

The results for an active compound are expressed as the percent of a group of animals in which the effect of scopolamine is blocked, as manifested by an increased interval between being placed in the test chamber and re-entering the dark compartment.

Results of this assay for some of the compounds of this invention and those for tacrine (reference compound) are presented in Table 2.

TABLE 2

| Compound | Dose (mg/kg of body weight, s.c.) | % of Animals with Scopolamine Induced Memory Deficit Reversal |
|---|---|---|
| 3-(4-pyridinylamino)-1H-indole maleate | 10 | 70 |
| 1-methyl-3-(4-pyridinyl-amino)-1H-indole fumarate | 10 | 27 |
| | 3 | 29 |
| | 1 | 33 |
| 6-Chloro-3-(4-pyridinyl-amino)-1H-indole | 10 | 27 |
| | 3 | 20 |
| | 1 | 27 |
| Tacrine | 0.63 | 13 |
| Pilocarpine | 5.0 | 13 |

The utility is further demonstrated by the ability of these compounds to inhibit the activity of monoamine oxidase (an enzyme) and thereby to increase the brain levels of biogenic amine(s). This ability demonstrates utility as an antidepressant.

Inhibition of Type A and Type B Monoamine Oxidase Activity in Rat Brain Synaptosomes Purpose To determine the selective inhibition of the two forms of monoamine oxidase (MAO).

Introduction

The metabolic deamination of amines has been known for over a hundred years, but more recently Johnston (1) described two forms of monoamine oxidase, which are called "type A" and "type B". The existence of the two forms is based on different substrate and inhibitor specificities. Serotonin (5 HT) and norepinephrine (NE) are substrates for type A MAO, $\beta$-phenethylamine (PEA) and benzylamine are substrates for type B MAO, while dopamine (DA) and tyramine are substrates for both types. Clorgyline is a selective inhibitor of the type A enzyme, deprenyl and pargyline are selective inhibitors of the type B enzyme and tranylcypromine and iproniazid are nonselective inhibitors (2). It is recognized that MAO inhibitors have antidepressant properties.

Although various methods for measuring MAO activity are available, the described method involves the extraction of the radiolabeled deaminated metabolites of [$^3$H]-5 HT or [$^{14}$C]-$\beta$-phenethylamine. This procedure allows MAO-A and MAO-B activities to be measured either simultaneously or individually (3).

Procedure

A. Reagents
1. Phosphate buffer (0.5M), pH 7.4:
   134.4 g $NaH_2PO_4.7H_2O$, bring to 1 liter in distilled $H_2O$ (A)
   17.3 g $Na_2HPO_4$, bring to 250 ml in distilled $H_2O$ (B)
   Adjust pH of A to 7.4 by slowly adding B (volumes as needed)
   Dilute 1:10 in distilled $H_2O$ (0.05M $PO_4$ buffer, pH 7.4)
2. 0.25M Sucrose ($PO_4$ buffered):
   21.4 g sucrose, bring to 250 ml with 0.05M $PO_4$ buffer
3. Substrate for MAOA:
   a. Serotonin creatinine $SO_4$ (5 HT) is obtained from Sigma Chemical Company. A 5 mM stock solution is made up in 0.01N HCl. This is used to dilute the specific activity of the [$^3$H]-5 HT.
   b. [$^3$H]-5-Hydroxytryptamine creatinine $SO_4$ (20–30 Ci/mmol) is obtained from New England Nuclear.
   c. Add 12 μl of [$^3$H]-5 HT to 2 ml of the 5 mM 5 HT solution. (Final amine concentration in the assay is 200 μM: see below.)
4. Substrate for MAO-B
   a. β-phenethylamine (PEA) is obtained from Sigma Chemical Company. A 5 mM stock solution is made up in 0.01N HCl. This is used to dilute the specific activity of the [$^{14}$C]-PEA.
   b. β-[ethyl-1-$^{14}$C]-phenethylamine hydrochloride (40–50 mCi/mmol) is obtained from New England Nuclear.
   c. Add 12 μl of [$^{14}$C]-PEA to 2 ml of the 5 mM PEA solution. (Final amine concentration in the assay is 200 μM: see below.)
5. Equal amounts of MAO-A (5 HT) and MAO-B (PEA) substrates are combined for simultaneously testing both MAO types, i.e. mixed stock solution of 2.5 mM 5 HT and 2.5 mM PEA, 40 μl of this mixed solution gives a 200 μM final concentration of each amine in the assay. When testing only one MAO type, the individual 5 mM stock solutions must be diluted 1:1 with distilled water prior to adding 40 μl to the incubation mixture; i.e., same 200 ρM final amine concentration.

B. Tissue Preparation

Male Wistar rats weighing 150–250 grams were sacrificed and the brains rapidly removed. Whole brain minus cerebellum was homogenized in 30 volumes of ice-cold, phosphate-buffered 0.25M sucrose, using a Potter-Elvejhem homogenizer. The homogenate was centrifuged at 1000 g for 10 minutes and the supernatant ($S_1$) decanted and recentrifuged at 18,000 g for 20 minutes. The resulting pellet ($P_2$) was resuspended in fresh 0.25M sucrose and served as the tissue source for mitochondrial MAO.

C. Assay

10 μl 0.5M $PO_4$ buffer, pH 7.4
50 μl $H_2O$ or appropriate drug concentration
400 μl Tissue suspension Tubes are preincubated for 15 minutes at 37° C. and the assay is started by adding 40 μl of combined substrate ([$^3$H]-5 HT and [$^{14}$C]-PEA) at 15 second intervals. The tubes are incubated for 30 minutes at 37° C. and the reaction stopped by the addition of 0.3 ml 2N HCl. Tissue blank values are determined by adding the acid before the radioactive substrate. The oxidative products of the reaction are extracted with ethyl acetate/toluene (1:1). 5 ml of this mixture is added to the tubes. The resultant mixture is vortexed for 15 seconds to extract the deaminated metabolites into the organic phase and the latter is allowed to separate from the aqueous phase. The tubes are placed in acetone/dry ice bath to freeze the aqueous layer. When this layer is frozen, the top organic layer is poured into a scintillation vial. 10 ml of Liquiscint is added and the samples are counted using window settings for $^{14}$C in one channel and $^3$H in the second channel. $IC_{50}$ values are determined by log-probit analysis.

References

1. Johnston, J. P.: Some observations upon a new inhibitor of monoamine oxidase in brain tissue. Biochem. Pharmacol. 17: 1285–1297 (1968).
2. Fowler, C. J. and Ross, S. B.: Selective inhibitors of monoamine oxidase A and B: biochemical, pharmacological and clinical properties. Med. Res. Rev. 4: 323–328 (1984).
3. Kindt, M. V., Youngster, S. K., Sonsalla, P. K., Duvoisin, R. C. and Heikkila, R. E.: Role of monoamine oxidase-A (MAO-A) in the bioactivation and nigrostriatal dopaminergic neurotoxicity of the MPTP analog, 2'Me-MPTP. Eur. J. Pharmacol. 46: 313–318 (1988).

Results of the monoamine oxidase inhibition assay for representative compounds of this invention are presented in Table 3.

TABLE 3

| Compound | Inhibitory Concentration - $IC_{50}(\mu M)$ | |
|---|---|---|
| | MAO-A | MAO-B |
| 3-(4-pyridinylamino)-benzo[b]thiophene hydrochloride | 5.3 | 18 |
| 6-methoxy-3-)4-pyridinylamino)benzo[b]thiophene hydrochloride | 3.2 | 17 |
| 6-methoxy-3-(propyl-4-pyridinylamino)benzo[b]thiophene hydrochloride | 182 | 205 |
| 3-(4-pyridinylamino)-6-trifluoromethylbenzo[b]-thiophene hydrochloride | 60 | 165 |
| 6-chloro-3-(4-pyridinylamino)benzo[b]thiophene hydrochloride | 10.5 | 51 |
| 3-[(4-pyridinyl)amino]-1,2-benzisoxazole | 0.64 | 3.9 |
| 6-chloro-3-[(4-pyridinyl)amino]-1,2-benzisoxazole maleate | 2.8 | 51 |
| (Reference Compounds) | | |
| Deprenyl | 0.14 | 0.016 |
| Tranylcypromine | 0.19 | 0.12 |

SCHEDULE-INDUCED POLYDIPSIA IN RATS

Purpose:

Food deprived rates exposed to a fixed-interval feeding schedule and allowed free access to water develop an excessive drinking behavior known as polydipsia. This schedule-induced polydipsia (SIP) cannot be explained in terms of a physiological deficit due to water deprivation. Furthermore, it offers no benefit or reward to the rat (1). Just as SIP involves the exaggeration of the normal drinking behavior, the compulsive symptoms of obsessive-compulsive disorder (OCD) can be considered an exaggeration of normal human behaviors. Compounds that effectively reduce the symptoms of OCD in humans (2) also significantly attenuate polydipsia.

Methods:

Male Wistar rats (Charles River) weighing 180-220 grams were individually housed and maintained in accordance with the "NIH Guide to Care and Use of Laboratory Animals" (National Institute of Health Care Publications, No. 85-23, revised 1985) with a 12 hour light; 12 hour dark cycle and allowed free access to water. The rats were placed on a restricted diet which maintained 80% of their free feeding body weight. To induce polydipsia, rats were placed in operant chambers housed in sound attenuated boxes where a pellet dispenser automatically dispensed two 45 mg (Noyes) pellets on a fixed-interval 60 second (FI-60 sec.) schedule over a 150 minute test session. Water was available at all times in the operant chambers. After four weeks (Monday through Friday) of exposure to the FI-60 sec. feeding schedule, approximately 80% of the rats met a pre-determined criterion for water consumption (greater than 60 mls of water per session) and were considered polydipsic. Rats (N=8) were administered, intraperitoneally (IP), vehicle or the appropriate compound daily. Once dosing commenced, the rats were tested in the operant chambers once a week to assess SIP.

Drugs:

Compounds were either dissolved or suspended in distilled water plus a drop of Tween 80 and injected IP in a dosage volume of 1 ml/kg. The final volume was prepared to account for salt content and the dosage was expressed as 100% base. Results of the inhibition of SIP for representative compounds of this invention are presented in Table 4.

TABLE 4

| Compound | Dose (mg/kg/day) |
| --- | --- |
| 6-Chloro-3-(propyl-4-pyridinylamino)benzo[b]thiophene hydrochloride | Active at 30 and 15 |
| 6-chloro-3-[2-methylpropyl)(4-pyridinyl)amino]benzo[b]thiophene hydrochloride | Active at 15 |
| 3-[(2-methylpropyl)4-pyridinylamino)]-6-trifluoromethylbenzo[b]thiophene hydrochloride | Active at 15 |
| (Reference Compounds) | |
| Clomipramine | Active at 5 |
| Fluoxetine | Active at 5 |

Reference

1. Falk, J., (1971): The Nature and Determinants of Adjunctive Behavior, *Physiology and Behavior*. 6, 577-588.
2. Rapoport, J. L., (1991): Recent Advances in Obsessive-Compulsive Disorder, *Neuropsychopharmacology*. 5, 1-10.

Effective quantities of the compounds of the invention may be administered to a patient by any of the various methods, for example, orally as in capsule or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compounds, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0-300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present inventions are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in disposable syringes or multiple dose vials made of glass or plastic.

Examples of the compounds of this invention include:
3-(4-pyridinylamino)-1H-indole;
N-(1H-indol-3-yl)-(4-pyridinyl)propanamide;
3-(3-fluoro-4-pyridinylamino)-1H-indole;
ethyl 3-(4-pyridinylamino)indole-2-carboxylate;
6-chloro-3-(4-pyridinylamino)indole;
3-(4-pyridinylamino)indole-2-carboxylic acid;
6-fluoro-3-(4-pyridinylamino)indole;
6-trifluoromethyl-3-(4-pyridinylamino)indole;
1-methyl-3-(4-pyridinylamino)indole;
ethyl 1-methyl-3-(4-pyridinylamino)indole-2-carboxylate;
1-acetyl-3-(4-pyridinylamino(indole;
3-[(4-pyridinyl)amino]-1,2-benzisoxazole;
3-[(1-propyl)(4-pyridinyl)amino]-1,2-benzisoxazole;
6-chloro-3-[(4-pyridinyl)amino]-1,2-benzisoxazole;
6-chloro-3-[(4-pyridinyl)(propyl)amino]-1,2-benzisoxazole;
2-(4-pyridinylamino)benzo[b]thiophene;
2-(methyl-4-pyridinylamino)benzo[b]thiophene;
2-(propyl-4-pyridinylamino)benzo[b]thiophene;
N-(benzo[b]thien-2-yl)-N-butyl-4-pyridinamine;
N-(benzo[b]thien-2-yl)-N-(2-methylpropyl)-4-pyridinamine;
2-amino-N-(benzo[b]thien-2-yl)-N-(4-pyridinyl)acetamide;
3-(4-pyridinylamino)benzo[b]thiophene;
3-(methyl-4-pyridinylamino)benzo[b]thiophene;
3-(ethyl-4-pyridinylamino)benzo[b]thiophene;
3-(propyl-4-pyridinylamino)benzo[b]thiophene;
N-(benzo[b]thien-3-yl)-N-(2-methylpropyl)-4-pyridinamine;
N-(benzo[b]thien-3-yl)-N-butyl-4-pyridinamine;
6-fluoro-3-(4-pyridinylamino)benzo[b]thiophene;
6-fluoro-3-(methyl-4-pyridinylamino)benzo[b]thiophene;
3-(ethyl-4-pyridinylamino)-6-fluorobenzo[b]thiophene;
6-fluoro-3-(propyl-4-pyridinylamino)benzo[b]thiophene;
3-(butyl-4-pyridinylamino)-6-fluorobenzo[b]thiophene;
3-[(3-dimethylaminopropyl)-4-pyridinylamino]-6-fluorobenzo[b]thiophene;
6-fluoro-3-(3-fluoro-4-pyridinylamino)benzo[b]thiophene;
6-fluoro-3-[(3-fluoro-4-pyridinyl)propylamino]benzo[b]thiophene;
4-chloro-3-[(4-pyridinyl)amino]benzo[b]thiophene;
4-chloro-3-[(propyl)(4-pyridinyl)amino]benzo[b]thiophene;
4-chloro-3-[(2-methylpropyl)(4-pyridinyl)amino]benzo[b]thiophene;
4-chloro-3-[(3-{6-fluoro-3-benzisoxazolyl}propyl)(4-pyridinyl)amino]benzo[b]thiophene;
6-chloro-3-(4-pyridinylamino)benzo[b]thiophene;
6-chloro-3-(methyl-4-pyridinylamino[b]thiophene;
6-chloro-3-(ethyl-4-pyridinylamino)benzo[b]thiophene;
6-chloro-3-(propyl-4-pyridinylamino)benzo[b]thiophene;
6-chloro-3-[(1-methylethyl)(4-pyridinyl)amino]benzo[b]thiophene;
6-chloro-3-[(2-propenyl)(4-pyridinyl)amino]benzo[b]thiophene;
6-chloro-3-[(2-methoxyethyl)(4-pyridinyl)amino]benzo[b]thiophene;
3-(butyl-4-pyridinylamino)-6-chlorobenzo[b]thiophene;
6-chloro-3-[(2-methylpropyl)(4-pyridinyl)amino]benzo[b]thiophene;
6-chloro-3-[(cyclopropylmethyl)(4-pyridinyl)amino]benzo[b]thiophene;
6-chloro-3-[(2,2-dimethylpropyl)(4-pyridinyl)amino]benzo[b]thiophene;
6-chloro-3-[(3,3-dimethyl-propenyl)(4-pyridinyl)amino]benzo[b]thiophene;
6-chloro-3-[(cyclohexylmethyl)(4-pyridinyl)amino]benzo[b]thiophene;
6-chloro-3-[(benzyl)(4-pyridinyl)amino]benzo[b]thiophene;
6-chloro-3-[(2-fluorobenzyl)(4-pyridinyl)amino]benzo[b]thiophene;
1-[4-[3-(6-chlorobenzo[b]thien-3-yl-4-pyridinylamino)propoxy]-3-methoxyphenyl]ethanone;
6-chloro-3-[(4,4-{bis-[4-fluorophenyl]}butyl)(4-pyridinyl)amino]benzo[b]thiophene;
6-chloro-3-[(4-fluorobenzoylpropyl)(4-pyridinyl)amino]benzo[b]thiophene;
6-chloro-3-[(3-{6-fluoro-3-benzisoxazolyl}propyl)(4-pyridinyl)amino]benzo[b]thiophene;
7-chloro-3-(4-pyridinyl)aminobenzo[b]thiophene;
7-chloro-3-[(propyl)(4-pyridinyl)amino]benzo[b]thiophene;
7-chloro-3-[(2-methylpropyl)(4-pyridinyl)amino]benzo[b]thiophene;
3-(4-pyridinylamino)-6-trifluoromethylbenzo[b]thiophene;
3-(methyl-4-pyridinylamino)-6-trifluoromethylbenzo[b]thiophene;
3-(ethyl-4-pyridinylamino)-6-trifluoromethylbenzo[b]thiophene;
3-(propyl-4-pyridinylamino)-6-trifluoromethylbenzo[b]thiophene;
3-[(2-propenyl)(4-pyridinylamino)]-6-trifluoromethylbenzo[b]thiophene;
3-(butyl-4-pyridinylamino)-6-trifluoromethylbenzo[b]thiophene;
3-[(2-methylpropyl)(4-pyridinylamino)]-6-trifluoromethylbenzo[b]thiophene;
6-methoxy-3-(4-pyridinylamino)benzo[b]thiophene;
7-chloro-3-[(4-pyridinyl)(2,2-dimethylpropyl)amino]benzo[b]thiophene;
7-chloro-3-[(3-(4-fluorobenzoyl)propyl)(4-pyridinyl)amino]benzo[b]thiophene;
7-chloro-3-[(4,4-{bis-[4-fluorophenyl]}butyl)(4-pyridinyl)amino]benzo[b]thiophene;
7-chloro-3-[(3-(4-acetyl-2-methoxyphenoxy)propyl)(4-pyridinyl)amino]benzo[b]thiophene;
7-chloro-3-{(3-{6-fluoro-3-benzisoxazolyl}propyl)(4-pyridinyl)amino]benzo[b]thiophene;
N-(5-trifluoromethylbenzo[b]thien-3-yl)-4-pyridinamine;
N-methyl-N-(5-trifluoromethylbenzo[b]thien-3-yl)-4-pyridinamine;
N-propyl-N-(5-trifluoromethylbenzo[b]thien-3-yl)-4-pyridinamine;
N-(2-methylpropyl)-N-(5-trifluoromethylbenzo[b]thien-3-yl)-4-pyridinamine;
6-methoxy-3-(propyl-4-pyridinylamino)benzo[b]thiophene; and
6-hydroxy-3-(propyl-4-pyridinylamino)benzo[b]thiophene;

The following examples are presented in order to illustrate the present invention.

EXAMPLE 1

3-(4-Pyridinylamino)-1H-indole maleate

A solution of 3-aminoindole (8g) and 4-chloropyridine hydrochloride (12 g) in 150 mL 1-methyl-2-pyrrolidinone (NMP hereinafter) was stirred at 70°–75° C. for one hour, after which additional 4-chloropyridine hydrochloride (4 g) was added. After stirring a total of two hours, the mixture was cooled, stirred with water, basified with sodium carbonate and extracted with ethyl acetate. The organic extract was washed successively with water and a saturated sodium chloride solution and thereafter dried (anhydrous magnesium sulfate), filtered and concentrated to 20 g of a dark oil. This was eluted through silica with 20% methanol in dichloromethane (DCM hereinafter) via HPLC (high performance liquid chromatography) to yield 7 g of a dark oil. This oil was crystallized from acetonitrile to yield 3 g of light brown crystals, m.p. 192°–193°. A 2.8 g portion was converted to the maleate salt in 50% methanol/ether to yield 3.5 g of light tan crystals, m.p. 149°–151° C. Recrystallization from 50% methanol/ether yielded 3.4 g of light tan crystals, m.p. 149°–151° C.

ANALYSIS: Calculated for $C_{17}H_{15}N_3O_4$: 62.76% C; 4.65% H; 12.92% N; Found: 62.85% C; 4.70% H; 12.92% N.

EXAMPLE 2

N-(1H-Indol-3-yl)-N-(4-pyridinyl)propanamide 3-(4-Pyridinylamino)-1H-indole (3 g) was added to a solution prepared from propionic anhydride (3 g), 10 mL dichloromethane and 10 mL toluene. The resultant solution was stirred one hour at ambient temperature and thereafter stirred with water and basified with sodium carbonate. The product was extracted into dichloromethane. The dried (anhydrous magnesium sulfate) organic layer was filtered and concentrated. The residue was eluted through silica with 50% ethyl acetate in dichloromethane via flash column chromatography to yield 3.5 g of a light tan solid, m.p. 166°–168°. A 1.5 g portion was recrystallized from acetonitrile to yield 1.3 g of light tan crystals, m.p. 168°–170°.

ANALYSIS: Calculated for $C_{16}H_{15}N_3O$: 72.43% C; 5.70% H; 15.84% N; Found: 72.06% C; 5.69% H; 15.94% N.

EXAMPLE 3

3-(3-Fluoro-4-pyridinylamino)-1H-indole hydrochloride

A solution of 3-aminoindole (7 g) and 4-chloro-3-fluoropyridine hydrochloride (13 g) in 200 mL of 1-methyl-2-pyrrolidinone was stirred at 75°–80° C. for two hours, after which additional 4-chloro-3-fluoropyridine hydrochloride (5 g) was added. After stirring a total of three hours the mixture was cooled, stirred with water, basified with sodium carbonate and extracted with ethyl acetate. The dried (anhydrous magnesium sulfate) organic layer was filtered and concentrated to 20 g of a dark oil. Elution through silica gel first with dichloromethane and then with 50% ethyl acetate in dichloromethane via flash column chromatography yielded 17 g of a dark oil. This oil was eluted through silica with ether via flash column chromatography to yield 10.6 g of a dark oil. This oil was eluted through silica with 20% ethyl acetate in dichloromethane via HPLC to yield 8 g of a dark oil. A six gram portion was converted to the hydrochloride salt in methanol/ether to yield 3.5 g of a solid, m.p. >250° C. Recrystallization from 30% methanol in ether yielded 2.7 g of crystals, m.p. 256°–258° C. (dec.).

ANALYSIS: Calculated for $C_{13}H_{11}ClFN_3$: 59.21% C; 4.20% H; 15.93% N; Found: 59.06% C; 4.14% H; 15.49% N.

EXAMPLE 4

Ethyl 3-(4-Pyridinylamino)indole-2-carboxylate

A solution ethyl 3-aminoindole-2-carboxylate (4.94 g, 24.2 mmole) and 4-chloropyridine hydrochloride (3.63 g, 24.2 mmole) in 70 mL of 1-methyl-2-pyrrolidinone was heated at 165° C. for 6 hours. The reaction mixture was then quenched into water and the aqueous phase was washed with ethyl acetate. After basification with a potassium carbonate solution, a solid was filtered, rinsed with water and ether and dried to give 4.13 g of a brown solid. A 2.2 g portion was recrystallized from methanol (charcoal treatment) to give 1.40 g of an off-white solid, mp: 248°–250° C. (dec.)

ANALYSIS: Calculated for $C_{16}H_{15}N_3O_2$: 68.31% C; 5.37% H; 14.94% N; Found: 68.29% C; 5.34% H; 14.92% N.

EXAMPLE 5

6-Chloro-3(4-pyridinylamino)indole

Part A:

A solution of 2-acetylamino-4-chlorobenzonitrile (8.01 g, 41.2 mmole) in 70 mL of dimethylformamide (DMF hereinafter) was treated with $K_2CO_3$ (6.8 g, 49.4 mmole) followed by treatment with (t-butyl) bromoacetate (8.84 g, 45.3 mmole). After stirring at ambient temperature for 3 hours, the mixture was added to water, and the resulting solid was filtered, rinsed with water and dried to give 12.3 g of a white powder, m.p. 132°–135° C.

Part B:

A solution of tert-butyl 2-[(5-chloro-2-cyanophenyl)-(acetyl)amino] acetate (12.2 g, 39.5 mmole) in 300 mL methanol was treated with 100 mL of a saturated $K_2CO_3$ solution and 50 mL $H_2O$. After heating on a steam bath for 1 hour, the mixture was added to water. The resulting solid was filtered, rinsed with water and dried to give 9.39 g of an off-white solid.

Part C:

A solution of tert-butyl 3-amino-6-chloroindole-2-carboxylate (4.91 g, 18.4 mmole) and 4-chloropyridine hydrochloride (2.76 g, 18.4 mmole) in 40 mL of N-methyl-2-pyrrolidinone was heated at 80° C. for 4 hours. The reaction mixture was then poured into water, the aqueous phase was washed with ethyl acetate and then basified with solid $NaHCO_3$. The resulting solid was filtered, rinsed with water and dried to give 3.84 g of a tan solid.

Part D:

A solution of t-butyl 6-chloro-3-(4-pyridinylamino)indole-2-carboxylate (3.56 g, 10.3 mmole) and pyridine hydrochloride (1.32 g, 11.4 mmole) in 25 mL of N-methyl-2-pyrrolinone was heated at 160° C. for 4 hours. The reaction mixture was then quenched into a chilled dilute potassium carbonate solution and the aqueous phase was extracted with ethyl acetate (3×). The combined organics were washed with water, dried and concentrated to give 1.92 g of a brown solid, mp 208°–213° C. This was twice recrystallized from methanol/water to give 1.17 g of a tan powder, mp: 205°–208° C.

ANALYSIS: Calculated for $C_{13}H_{10}ClN_3$: 64.07% C; 4.14% H; 17.24% N; Found: 63.72% C; 4.15% H; 17.09% N.

EXAMPLE 6

3-(4-Pyridinylamino)indole-2-carboxylic acid maleate

Part A:

A solution of 2-acetylaminobenzonitrile (7.78 g, 48.6 mmole) in 50 mL of DMF was treated with potassium butoxide (6.54 g, 58.3 mmole), followed by treatment with t-butyl bromoacetate (10.4 g, 53.4 mmole). After stirring for 1.5 hours at ambient temperature, the mixture was added to water, and the resulting solid was filtered, rinsed with water and dried to give 9.08 g of a white powder.

Part B:

A solution of t-butyl 1-acetyl-3-aminoindole-2-carboxylate (51.2 g, 187 mmole) in 250 mL methanol was treated with 100 mL of a saturated $K_2CO_3$ solution and 100 mL water. After heating at 70° C. for 4 hours, the mixture was then added to water and the resulting solid was filtered, rinsed with water and dried to give 39.0 g of a tan solid.

Part C:

A mixture of t-butyl 3-aminoindole-2-carboxylate (21.0 g, 90.4 mmole) and 4-chloropyridine hydrochloride in 125 mL NMP was heated at 80° C. for 4.5 hours. The reaction mixture was added to water, washed with ethyl acetate and the aqueous phase was basified with solid $K_2CO_3$. Extraction of the aqueous phase with ethyl acetate and trituration of the resulting solid with ethyl ether gave 6.85 g of a dark solid.

Part D:

A solution of t-butyl 3-aminoindole-2-carboxylate (8.73 g, 31.8 mmole) and 4-chloropyridine hydrochloride (4.53 g, 30.2 mmole) in 50 mL of 1-methyl-2-pyrrolidinone was heated at 150° C. for 3 hours. The reaction mixture was then quenched into water and washed with ethyl acetate. After basification with a potassium carbonate solution, the aqueous phase was washed with ethyl acetate and allowed to stand overnight during which time a solid precipitated out of the solution. This was filtered, rinsed with water and ether and dried to afford 3.2 g of a greenish solid. This was suspended in methanol, treated with excess maleic acid and filtered and the filtrate was concentrated to a solid. The resulting solid was recrystallized from methanol/ethyl ether (charcoal treatment) to give 1.81 g of a yellow powder, mp: 188°–190° C.

ANALYSIS: Calculated for $C_{14}H_{11}N_3O_2.C_4H_4O_4$: 58.54% C; 4.08% H; 11.38% N; Found: 58.47% C; 4.09% H; 11.29% N.

EXAMPLE 7

6-Fluoro-3-(4-pyridinylamino)indole maleate

Part A:

A solution of 2-acetylamino-4-fluorobenzonitrile (19.7 g, 111 mmole) in 135 mL of DMF was treated with $K_2CO_3$ (18.3 g, 133 mmole) followed by treatment with t-butyl bromoacetate (23.7 g, 122 mmole). After stirring at ambient temperature for 1.5 hours, the mixture was added to water, and the resulting solid was filtered, rinsed with water and dried to give 29.2 g of a white powder.

Part B:

A solution of t-butyl 2-[(5-fluoro-2-cyanophenyl)-(acetyl)amino]acetate (29.2 g, 99.9 mmole) in 600 mL of methanol was treated with 200 mL of a saturated $K_2CO_3$ solution and 50 mL water. After heating at 70° C. for ½ hour, the mixture was added to water, and the resulting solid was filtered, rinsed with water and dried to give 19.9 g of white plates.

Part C:

A solution of t-butyl 3-amino-6-fluoroindole-2-carboxylate (9.36 g, 37.4 mmole) and 4-chloropyridine hydrochloride (6.2 g, 41.1 mmole) in 75 mL of N-methylpyrrolidinone was heated at 75° C. for a total of 7 hours. During this time, additional 4-chloropyridine hydrochloride (0.905 g and 0.54 g) was added. The reaction mixture was then added to water and the aqueous phase was washed with ethyl acetate. The aqueous phase was then basified with solid $NaHCO_3$ and the resulting solid was filtered, rinsed with water and dried to give 8.26 g of a tan solid, m.p. 228°–230° C. (dec.)

Part D:

t-Butyl 6-fluoro-3-(4-pyridinylamino)indole-2-carboxylate (2.10 g, 6.41 mmole) was added to chilled trifluoroacetic acid (20 mL). The mixture was stirred for 1 hour at ambient temperature and then heated at 100° C. for 3.5 hours. The reaction mixture was then quenched into a chilled dilute potassium carbonate solution and the resulting solid was filtered, washed with water and dried. Purification via flash chromatography (1%→3% $Et_3N$/EtOAc) gave 0.68 g of a tan solid. This was combined with a product obtained from another run, dissolved in methanol and treated with 1.1 equivalents of maleic acid. The salt was crystallized out with ethyl ether to give 1.28 g of a yellowish powder, mp: 158°–160° C.

ANALYSIS: Calculated for $C_{13}H_{10}FN_3.C_4H_4O_4$: 59.48% C; 4.11% H; 12.24% N; Found: 59.55% C; 4.27% H; 12.14% N.

EXAMPLE 8

6-Trifluoromethyl-3-(4-pyridinylamino)indole

Part A:

A solution of 2-acetylamino-4-trifluoromethyl benzonitrile (17.2 g, 75.7 mmole) in 80 mL of DMF was treated with $K_2CO_3$ (12.6 g, 90.9 mmole) followed by treatment with t-butyl bromoacetate (14.8 g, 75.7 mmole). After stirring at ambient temperature for 1 hour, the mixture was then added to water, extracted with ethyl acetate and the organics were washed with water, dried, filtered and concentrated to give 27.2 g of an oil.

Part B:

A solution of t-butyl 2-[(5-trifluoromethyl-2-cyanophenyl)(acetyl)amino] acetate (27.2 g, 75.7 mmole) in 210 mL of methanol was treated with 80 mL of a saturated $K_2CO_3$ solution and 80 mL water. After heating at 70° C. for 45 minutes, the reaction mixture was added to water, and the resulting solid was filtered, rinsed with water and dried to give 17.9 g of a tan powder.

Part C:

A mixture of t-butyl 3-amino-6-trifluoromethylindole-2-carboxylate (17.6 g, 58.7 mmole) and 4-chloropyridine hydrochloride (9.7 g, 64.5 mmole) in 100 mL of NMP was heated at 70° C. for 3 hours. An additional 4.1 g of 4-chloropyridine hydrochloride was added and heating was continued for 3 hours. The reaction mixture was added to water and the aqueous phase was washed with ethyl acetate, basified with solid $K_2CO_3$ and then extracted with ethyl acetate. The organics were washed with water, dried, filtered and concentrated to give a solid which was recrystallized from methanol/water to give 11.13 g of a yellow powder.

Part D:

A solution of t-butyl 6-trifluoromethyl-3-(4-pyridinylamino)indole-2-carboxylate (11.0 g, 29.2 mmole) and pyridine hydrochloride (3.71 g, 32.1 mmole) in 75 mL of N-methyl-2-pyrrolidinone was heated at 170° C. for 5 hours. The reaction mixture was then quenched into a chilled dilute potassium carbonate solution and the aqueous phase was extracted with ethyl acetate (3×). The combined organics were washed with water, dried and concentrated to give 3.89 g of a brown solid. This was recrystallized from methanol/water to give 2.76 g of a tan powder, mp: 178°–180° C.

ANALYSIS: Calculated for $C_{14}H_{10}F_3N_3$: 60.65% C; 3.64% H; 15.16% N; Found: 60.53% C; 3.70% H; 15.10% N.

EXAMPLE 9

1-Methyl-3-(4-pyridinylamino)indole fumarate

A solution of 3-(4-pyridinylamino)-1H-indole (1.7 g, 8.12 mmole) in 50 mL of tetrahydrofuran was treated with potassium t-butoxide (1.0 g, 8.93 mmole). This was followed by the addition of dimethyl sulfate (1.08 g, 8.53 mmole). After stirring for 20 minutes, the mixture was treated with 6 mL of aqueous ammonia and the solvent was concentrated off. The residue was then partitioned between water and ethyl acetate and the aqueous phase was extracted with ethyl acetate (2×). The combined organics were washed with water, dried (saturated NaCl, MgSO₄), filtered and concentrated. Purification via flash chromatography (5% MeOH/DCM) gave 0.83 g of a tan fibrous solid. This was dissolved in methanol and treated with 1.1 equivalents of fumaric acid. The salt was crystallized out with ethyl ether to give 0.62 g of a tan powder. This was combined with a product obtained from another run and recrystallized from methanol/ethyl ether to give 1.03 g of a yellowish powder, mp: 161°–164° C.

ANALYSIS: Calculated for $C_{14}H_{13}N_3.C_4H_4O_4$: 63.71% C; 5.05% H; 12.38% N; Found: 63.81% C; 5.13% H; 12.32% N.

EXAMPLE 10

Ethyl 1-methyl-3-(4-Pyridinylamino)indole-2-carboxylate maleate

Ethyl 3-(pyridinylamino)indole-2-carboxylate (2.40 g, 8.53 mmole) in 80 mL tetrahydrofuran (ice-cooled) was treated with potassium t-butoxide (1.01 g, 8.95 mmole) followed by dimethyl sulfate (1.08 g, 8.53 mmole). After stirring for 15 minutes, the reaction mixture was quenched into NH₄OH solution and the aqueous phase was extracted with ethyl acetate (3×). The combined organics were washed with water, dried (MgSO₄), filtered and concentrated. Purification of the residue via flash chromatography (4% MeOH/DCM) gave 1.7 g (67%) of a pale violet solid. This was dissolved in methanol, treated with 1.1 equivalents of maleic acid followed by a charcoal treatment and the salt was crystallized out with ether to give 2.05 g (58%) of an off-white solid, mp: 169°–170° C. (dec.)

ANALYSIS: Calculated for $C_{17}H_{17}N_3O_2.C_4H_4O_4$: 61.31% C; 5.14% H; 10.21% N; Found: 61.30% C; 5.13% H; 10.09% N.

EXAMPLE 11

1-Acetyl-3-(4-pyridinylamino)indole maleate

A solution of t-butyl 1-acetyl-3-aminoindole-2-carboxylate (8.73 g, 31.8 mmole) and 4-chloropyridine hydrochloride (4.53 g, 30.2 mmole) in 50 mL of 1-methyl-2-pyrrolidinone was heated at 150° C. for 2.5 hours. The reaction mixture was then quenched into water and the aqueous phase was washed with ethyl acetate. After basification with potassium carbonate solution, the aqueous mixture was extracted with ethyl acetate, the organics were washed with water and dried (MgSO₄). This was concentrated to a solid which was triturated with ether to give 2.53 g (32%) of a brown solid, mp: 200°–206° C. A 1.91 g portion was dissolved in methanol and treated with 1.1 eq. of maleic acid. The salt was crystallized out with ether to give 2.25 g of a tan solid, mp: 168°–170° C. (dec.). This was twice recrystallized from methanol/ether to give 1.64 g (19%) of a tan solid, mp: 174°–175° C.

ANALYSIS: Calculated for $C_{15}H_{13}N_3O.C_4H_4O_4$: 62.12% C; 4.66% H; 11.44% N;

EXAMPLE 12

3-[(4-pyridinyl)amino]-1,2-benzisoxazole

A mixture of 3-amino-1,2-benzisoxazole (9.94 g, 74.18 mmole, prepared according to a method described in G. M. Shutske and K. J. Kapples, J. Heterocyclic Chem., 26, 1293 (1989)), 4-chloropyridine hydrochloride (22.27 g, 197 mmole) and 1-methyl-2-pyrolidinone was stirred vigorously at 130° C. for three hours. The reaction mixture was cooled, diluted with NaHCO₃, and extracted with EtOAc, after which the organics were washed with water, dried (MgSO₄), and concentrated. The residue was purified by flash chromatography (florisil, EtOAc), and then triturated with diethyl ether to yield 4.04 g (26%) of a fine brown solid. A 2.0 g portion was dissolved in boiling methanol and treated with charcoal (Darco) after which the product crystallized to yield 1.38 g of pale yellow crystals, mp 203° C. (dec.).

ANALYSIS: Calculated for $C_{12}H_9N_3O$: 68.24% C; 4.29% H; 19.89% N; Found: 68.14% C; 4.12% H; 20.06% N.

EXAMPLE 13

3-[(1-propyl)(4-pyridinyl)amino]-1,2-benzisoxazole maleate

To a suspension of pentane washed sodium hydride (0.48 g, 11.99 mmole) in DMF (10 ML) at 0° C. was added dropwise a solution of 3-[(4-pyridinyl)amino]-1,2-benzisoxazole (2.41 g, 11.42 mmole) in DMF (20 mL). The reaction mixture was stirred at 0° C. for 15 minutes and 1-bromopropane (1.09 mL, 11.99 mmole) was added. The reaction mixture was stirred at room temperature for one hour and additional sodium hydride (50 mg) and 1-bromopropane (0.1 mL) were added, after which the reaction mixture was heated at 60° C. for a half hour. After cooling, the mixture was distributed between water and diethyl ether, and the organic phase was washed with water and dried (MgSO₄). The resulting solution was treated with charcoal (Darco) to remove yellow color and filtered over a column of florisil with EtOAc to remove polar impurities. Concentration of fractions yielded 750 mg of product. The maleate salt was formed in methanol/ diethyl ether to yield 912 mg of product from two crops, mp 145°-146.5° C.

ANALYSIS: Calculated for $C_{15}H_{15}N_3O \cdot C_4H_4O_4$: 61.78% C; 5.18% H; 11.38% N; Found: 61.68% C; 5.07% H; 11.36% N.

EXAMPLE 14

Part A:

3-Amino-6-chloro-1,2-benzisoxazole

4-Chloro-2-[((isopropylidene)amino)oxy]benzonitrile (30 g) was refluxed for one hour in a 1:1 mixture of ethanol and 5% HCl (1 L). The reaction mixture was cooled, basified with saturated $NaHCO_3$, extracted several times with ethyl acetate, dried ($MgSO_4$), and concentrated to obtain a semisolid. This was triturated with pentane and dried under vacuum at 50° C. for three hours to yield 17.9 g of product. An analytical sample was obtained by recrystallization from ethyl acetate/heptane, mp 130°-130.5° C.

ANALYSIS: Calculated for $C_7H_5ClN_2O$: 49.87% C; 2.99% H; 16.62% N; Found: 49.70% C; 2.93% H; 16.66% N.

Part B:

6-Chloro-3-[(4-pyridinyl)amino]-1,2-benzisoxazole maleate

To a solution of 3-amino-6-chloro-1,2-benzisoxazole (5.0 g, 29.67 mmole) in NMP (60 mL) was added 4-chloropyridine hydrochloride (9.1 g). This mixture was stirred vigorously while hearing at 130° C. for 1.5 hours. The reaction mixture was cooled and neutralized with saturated $NaHCO_3$, and water was added to obtain a thick brown precipitate (total volume 600 mL) which was filtered, washed with water and air dried. This was flash chromatographed (7×15 cm column, silica gel) eluting first with ethyl acetate and then with 10% methanol/ethyl acetate to yield 1.93 g of product contaminated with NMP. The maleate salt was formed in methanol and recrystallized from ethanol to yield 1.17 g of product, mp 203° C. (dec.), after drying under high vacuum over refluxing xylenes.

ANALYSIS: Calculated for $C_{16}H_{12}ClN_3O_5$: 53.13% C; 3.34% H; 11.62% N; Found: 53.02% C; 3.14% H; 11.44% N.

EXAMPLE 15

6-Chloro-3-[(4-pyridinyl)(propyl)amino]-1,2-benzisoxazole maleate

To a suspension of pentane washed sodium hydride (380 mg, 9.49 mmole) in DMF (5 mL), was added 1-bromopropane (0.862 mL), and thereafter 6-chloro-3-(4-pyridinyl)amino-1,2-benzisoxazole (2.33 g, 9.49 mmole) in DMF (10 mL) was added dropwise. After stirring for 1.5 hours, an additional 0.3 mL of 1-bromopropane was added and the reaction mixture was heated to 60° C. for a half hour. The reaction mixture was cooled and distributed between diethyl ether and water, and the resultant mixture was filtered to recover 6-chloro-3-[1-propyl-N-4(1H)pyridinyl]-1,2-benzisoxazole, which is the major product of the reaction. The organic phase was separated and the aqueous phase was extracted with ethyl acetate. The organic were combined, washed with water, dried ($MgSO_4$), concentrated, and flash chromatographed (silica gel) with ethyl acetate to yield 354 mg of clean product as an oil. The maleate salt was formed in methanol, concentrated, recrystallized from methanol/diethyl ether and dried under high vacuum, $P_2O_5$, and refluxing ethanol to yield 274 mg of product as a white fluffy solid, mp 141°-146.5° C.

ANALYSIS: Calculated for $C_{15}H_{14}N_3OCl \cdot C_4H_4O_4$: 56.51% C; 4.49% H; 10.41% N; Found: 56.60% C; 4.42% H; 10.57% N.

EXAMPLE 16

2-(4-Pyridinylamino)benzo[b]thiophene

A solution of 2-aminobenzo[b]thiophene[1] (10 g) and 4-chloropyridine hydrochloride (12 g) in 100 mL of 1-methyl-2-pyrrolidinone was stirred at 75°-80° C. for 1.5 hours. After cooling, the reaction mixture was stirred with water and washed with ether, and the layers were separated from each other. The aqueous layer was basified with 30% aqueous ammonium hydroxide. The precipitate was collected, washed with water and collected again. Trituration with acetonitrile afforded 6 g of a light tan solid, mp 254°-258° C. (dec.). Recrystallization of 3 g from acetonitrile afforded 1.1 g of flocculent tan crystals, mp 258°-260° C. (dec.). [1]G. W. Stacy, et al., J. Org. Chem., 30, 4074 (1965).

ANALYSIS; Calculated for $C_{13}H_{10}N_2S$: 69.00% C; 4.45% H; 12.38% N; Found: 68.72% C; 4.27% H; 12.42% N.

EXAMPLE 17

2-(Methyl-4-pyridinylamino)benzo[b]thiophene hydrochloride 2-(4-Pyridinylamino)benzo[b]thiophene (4 g) was added slowly portionwise to an ice-cooled suspension of sodium hydride (60% oil dispersion, 0.8 g, washed with heptane) in 40 mL of dimethylformamide. After anion formation was completed, dimethyl sulfate (2.5 g) was added. The reaction mixture was stirred for one hour and thereafter poured into ice-water and extracted with ether. The organic extract was washed with water and saturated sodium chloride solution, and thereafter dried (anhydrous magnesium sulfate), filtered and concentrated to 5 g of a dark oil. Elution through silica with ethyl acetate via flash column chromatography afforded 1.7 g of an amber oil. Conversion to the hydrochloride salt in 10% methanol in ether afforded 1.7 g of yellow crystals, mp 285°-287° C. (dec.).

ANALYSIS: Calculated for $C_{14}H_{13}ClN_2S$: 60.75% C; 4.73% H; 10.12% N; Found: 60.54% C; 4.78% H; 10.07% N.

EXAMPLE 18

2-(Propyl-4-pyridinylamino)benzo[b]thiophene hydrochloride 2-(4-Pyridinylamino)benzo[b]thiophene (3.5 g) was added slowly portionwise to an ice-cooled suspension of sodium hydride (60% oil dispersion, 0.7 g, washed with heptane) in 50 mL of dimethylformamide. After anion formation was completed, 1-bromopropane (2 g) was added. The reaction mixture was stirred for one hour and thereafter poured into ice-water and extracted with ethyl acetate. The organic extract was washed with water and saturated sodium chloride solution, and thereafter dried (anhydrous magnesium sulfate), filtered and concentrated to 6 g of a dark oil. Elution through silica with ethyl acetate via flash column chromatography afforded 3.5 g of an amber oil. Conversion to the hydrochloride salt in 20% methanol in ether afforded 3.4 g of yellowish crystals, mp 258°-260° C.

ANALYSIS: Calculated for $C_{16}H_{17}ClN_2S$: 63.04% C; 5.62% H; 9.19% N; Found: 62.79% C; 5.64% H; 9.03% N.

EXAMPLE 19

N-(Benzo[b]thien-2-yl)-N-butyl-4-pyridinamine hydrochloride

N-(Benzo[b]thien-2-yl)-4-pyridinamine (5 g, 22 mmol) was added slowly portionwise to an ice-cooled suspension of sodium hydride (60% oil dispersion, 1.0 g, 25 mmol, washed with heptane) in 50 mL of dimethylformamide. After the anion formation was completed, 1-bromobutane (3.4 g, 25 mmol) was added. After stirring one hour, the reaction mixture was poured into ice-water and extracted with ethyl acetate. The organic extract was washed with water and a saturated sodium chloride solution, and then was dried (anhydrous magnesium sulfate), filtered and concentrated to 7 g of a dark oil. Elution through silica with ethyl acetate via flash column chromatography afforded 3.7 g of an oil. Elution through alumina with ether via column chromatography afforded 3.4 g of an amber oil. Conversion to the hydrochloride salt in 10% methanol in ether afforded 3.1 g of yellow crystals, mp 247°–249° C. (dec.)

ANALYSIS: Calculated for $C_{17}H_{19}ClN_2S$: 64.03% C; 6.01% H; 8.79% N; Found: 63.90% C; 6.19% H; 8.93% N.

EXAMPLE 20

N-(Benzo[b]thien-2-yl)-N-(2-methylpropyl)-4-pyridinamine hydrochloride

N-(Benzo[b]thien-2-yl)-4-pyridinamine (6 g, 26.5 mmol) was added slowly portionwise as a powder to an ice-cooled suspension of sodium hydride (60% oil dispersion, 1.3 g, 32 mmol, washed with heptane) in 50 mL of dimethylformamide. After the anion formation was completed, 1-bromo-2-methylpropane (4.4 g, 32 mmol) was added. The mixture was stirred for two hours and more 1-bromo-2-methylpropane (1.7 g, 12 mmol) was added to ensure complete alkylation. After stirring one additional hour, the reaction mixture was cooled, poured into ice-water and extracted with ethyl acetate. The organic extract was washed with water, and then was dried (anhydrous magnesium sulfate), filtered and concentrated to 10 g of a dark oil. Elution through silica with ethyl acetate via flash column chromatography afforded 4.2 g of a yellow oil. Conversion to the hydrochloride salt in 10% methanol in ether afforded 3.2 g of yellow crystals, mp 260°–262° C. (dec.).

ANALYSIS: Calculated for $C_{17}H_{19}ClN_2S$: 64.03% C; 6.01% H; 8.79% N; Found: 63.98% C; 6.07% C; 8.68% N.

EXAMPLE 21

2-Amino-N-(benzo[b]thien-2-yl)-N-(4-pyridinyl)acetamide 1,3-Dicyclohexylcarbodiimide (1.9 g, 9.9 mmol) was added with stirring to a solution of 2-(4-pyridinylamino)benzo[b]thiophene (2 g, 8.8 mmol) and N-(tert-butoxycarbonyl)glycine (1.6 g, 9.1 mmol) in 200 mL of dichloromethane. After two hours the reaction mixture was filtered to remove precipitated 1,3-dicyclohexylurea (yield 1.9 g), and thereafter the filtrate was concentrated. Gradient elution of the residue through silica with dichloromethane followed by 10% ethyl acetate in dichloromethane via flash column chromatography afforded 2 g of 1,1-dimethylethyl[2-[N-(benzo[b]thien-2-yl)-N-(4-pyridinyl)]amino-2-oxoethyl] carbamate.

A solution of the carbamate (2 g, 5.2 mmol) in 50 mL of methanol and 10 mL of saturated ethereal hydrogen chloride was allowed to stand at ambient temperature for twenty hours, and thereafter concentrated. The residue was dissolved in water, basified with sodium carbonate and extracted with ethyl acetate. The organic extract was washed with water and saturated sodium chloride solution and dried (anhydrous magnesium sulfate), filtered and concentrated. Elution of the residue through silica with 10% methanol in dichloromethane via flash column chromatography afforded 0.3 g of a solid, mp 280°–284° C. Recrystallization from acetonitrile afforded 0.17 g of flocculent crystals, mp 266°–268° C. (dec.).

ANALYSIS: Calculated for $C_{15}H_{13}N_3OS$: 63.58% C; 4.62% H; 14.83% N; Found: 63.49% C; 4.73% H; 15.08% N.

EXAMPLE 22

3-(4-Pyridinylamino)benzo[b]thiophene hydrochloride

A solution of 3-aminobenzo[b]thiophene (3g, 20 mmol) and 4-chloropyridine hydrochloride (3.5 g, 23 mmol) in 50 mL of 1-methyl-2-pyrrolidinone was stirred at 80° for three hours, and thereafter cooled, stirred with water, basified with sodium carbonate and extracted with ethyl acetate. The organic extract was washed with water and saturated sodium chloride solution and dried (anhydrous magnesium sulfate), filtered and concentrated to 8 g dark oil. Elution through silica with ethyl acetate via flash column chromatography yielded 5 g of an amber oil. Conversion to the hydrochloride salt in methanol-ether yielded 3 g of a hygroscopic solid. Recrystallization from 50% methanol in ether yielded 1.8 g of rust colored crystals, mp 268°–270° (dec.).

ANALYSIS: Calculated for $C_{13}H_{11}ClN_2S$: 59.42% C; 4.22% H; 10.66% N; Found: 59.35% C; 4.23% H; 10.52% N.

EXAMPLE 23

3-(Methyl-4-pyridinylamino)benzo[b]thiophene hydrochloride

A solution of 3-(4-pyridinylamino)benzo[b]thiophene (3.3 g, 15 mmol) in 20 mL of dimethylformamide was added to a suspension of sodium hydride (60% oil dispersion, 0.7 g, 18 mmol, washed with heptane) in 10 mL of dimethylformamide. After anion formation was completed a solution of dimethyl sulfate (2.2 g, 17 mmol) in 5 mL of dimethylformamide was added. After one hour the reaction mixture was stirred with ice-water and extracted with ether. The organic extract was washed with water and saturated sodium chloride solution and dried (anhydrous magnesium sulfate), filtered and concentrated to afford an oil (3.5 g). Elution through silica with ethyl acetate via flash column chromatography yielded 2.7 g of a pale yellow oil. Conversion to the hydrochloride salt in 25% methanol in ether yielded 2.4 g of pale yellow crystals, mp 245°–246°.

ANALYSIS: Calculated for $C_{14}H_{13}ClN_2S$: 60.75% C; 4.73% H; 10.12% N; Found: 60.88% C; 4.77% H; 10.16% N.

EXAMPLE 24

3-(Ethyl-4-pyridinylamino)benzo[b]thiophene hydrochloride

A solution of 3-(4-pyridinylamino)benzo[b]thiophene (3.5 g, 15 mmol) in 20 mL of dimethylformamide was added to a suspension of sodium hydride (60% oil dispersion, 0.7 g, 18 mmol, washed with heptane) in 10 mL of dimethylformamide. After the anion formation was completed, a solution of diethyl sulfate (2.7 g, 18 mmol) in 5 mL of dimethylformamide was added. After one hour the reaction mixture was stirred with ice-water and extracted with ether. The organic extract was washed with water and saturated sodium chloride solution, and dried (anhydrous magnesium sulfate), filtered and concentrated to a yellow oil (3.5 g). Elution through silica with ethyl acetate via flash column chromatography yielded 2.5 g of a pale yellow oil. Conversion to the hydrochloride salt in 10% methanol in ether yielded 2.6 g of pale yellow crystals, mp 242°–244°.

ANALYSIS: Calculated for $C_{15}H_{15}ClN_2S$: 61.95% C; 5.20% H; 9.64% N; Found: 62.08% C; 5.19% H; 9.57% N.

EXAMPLE 25

3-(Propyl-4-pyridinylamino)benzo[b]thiophene hydrochloride

A solution of 3-(4-pyridinylamino)benzo[b]thiophene (3 g, 13 mmol) in 20 mL of dimethylformamide was added to a suspension of sodium hydride (60% oil dispersion, 0.6 g, 15 mmol, washed with heptane) in 10 mL of dimethylformamide. After the anion formation was completed, a solution of 1-bromopropane (2.1 g, 17 mmol) in 5 mL of dimethylformamide was added. After one hour the reaction mixture was stirred with ice-water and extracted with ether. The organic extract was washed with water and saturated sodium chloride solution, and dried (anhydrous magnesium sulfate), filtered and concentrated to 3.4 g of a yellow oil. Elution through silica with ethyl acetate via flash column chromatography yielded 2.8 g of a pale yellow oil. Conversion to the hydrochloride salt in 25% methanol in ether yielded 3.0 g of pale yellow crystals, mp 274°–276°.

ANALYSIS: Calculated for $C_{16}H_{17}ClN_2S$: 63.04% C; 5.62% H; 9.19% N; Found: 62.95% C; 5.73% H; 9.05% N.

EXAMPLE 26

N-(Benzo[b]thien-3-yl)-N-(2-methylpropyl)-4-pyridinamine hydrochloride

A solution of N-(benzo[b]thien-3-yl)-4-pyridinamine (4.0 g, 17.7 mmol) in 25 mL of dimethylformamide was added dropwise to an ice-cooled suspension of sodium hydride (60% oil dispersion, 0.8 g, 19.4 mmol, washed with heptane), in 10 mL of dimethylformamide. After the anion formation was completed, a solution of 1-bromo-2-methylpropane (2.8 g, 20.4 mmol) was added. The mixture was stirred for two hours at 45° C. At this time, sodium hydride (0.4 g, 9.7 mmol) and 1-bromo-2-methylpropane (1.5 g, 10.2 mmol) were added. After one more hour, additional amounts of sodium hydride (0.4 g, 9.7 mmol) and 1-bromo-2-methylpropane (1.5 g, 10.2 mmol) were added to ensure complete alkylation. After stirring one additional hour, the reaction mixture was cooled, poured into ice water and extracted with ethyl acetate. The organic extract was washed with water, dried (anhydrous magnesium sulfate), filtered and concentrated to 5.6 g of an amber oil. Elution through silica with ethyl acetate via flash column chromatography afforded 4.5 g of an amber oil. Conversion to the hydrochloride salt in 10% methanol in ether afforded 3.9 g of pale yellow crystals, mp 235°–237° C.

ANALYSIS: Calculated for $C_{17}H_{19}ClN_2S$: 64.03% C; 6.01% H; 8.79% N; Found: 63.88% C; 6.21% H; 8.84% N.

EXAMPLE 27

N-(Benzo[b]thien-3-yl)-N-butyl-4-pyridinamine hydrochloride

A solution of N-(benzo[b]thien-3-yl-4-pyridinamine (3.5 g) in 25 mL of dimethylformamide was added to an ice-cooled suspension of sodium hydride (60% oil dispersion, 0.8 g, 20 mmol, washed with heptane) in 10 mL of dimethylformamide. After the anion formation was completed, a solution of 1-bromobutane (2.2 g, 16 mmol) in 5 mL of dimethylformamide was added. After one hour, the reaction mixture was stirred with ice-water and extracted with ethyl acetate. The organic extract was washed with water and then was dried (anhydrous magnesium sulfate), filtered and concentrated to 4.2 g of a yellow oil. Elution through silica with ethyl acetate via flash column chromatography afforded 3.6 g of a pale yellow oil. Conversion to the hydrochloride salt in 10% methanol in ether afforded 3.6 g of pale yellow crystals, mp 217°–219° C.

ANALYSIS: Calculated for $C_{17}H_{19}ClN_2S$: 64.03% C; 6.01% H; 8.79% N; Found: 64.04% C; 5.97% H; 8.81% N.

EXAMPLE 28

6-Fluoro-3-(4-pyridinylamino)benzo[b]thiophene maleate

A solution of 3-amino-6-fluorobenzo[b]thiophene (7 g) and 4-chloropyridine hydrochloride (7 g) in 200 mL 1-methyl-2-pyrrolidinone was stirred one hour at 80°–85° C. and thereafter cooled, stirred with water, basified with sodium carbonate and extracted with ethyl acetate. The organic extract was washed successively with water and a saturated sodium chloride solution and thereafter dried (anhydrous magnesium sulfate), filtered and concentrated to 10 g of a dark oil. This oil was eluted through silica with 10% methanol in dichloromethane via HPLC to yield 4.7 g of a brown solid, m.p. 102°–106° C. The solid was converted to the maleate salt in 20% methanol in ether and immediately thereafter recrystallized from 20% methanol in ether to yield 2.9 g of white crystals, m.p. 172°–174° (dec.).

ANALYSIS: Calculated for $C_{17}H_{13}FN_2O_4S$: 56.66% C; 3.64% H; 7.78% N; Found: 56.41% C; 3.44% H; 7.68% N.

EXAMPLE 29

6-Fluoro-3-(methyl-4-pyridinylamino)benzo[b]thiophene hydrochloride

6-Fluoro-3-(4-pyridinylamino)benzo[b]thiophene (2 g, 8.2 mmol) was added portionwise as a powder to a suspension of sodium hydride (60% oil dispersion, 0.39 g, 9.8 mmol, washed with hexanes) in 50 mL of dimethylformamide. After the anion formation was completed, a solution of dimethyl sulfate (1.2 g, 10 mmol) in 5 mL of dimethylformamide was added. After one hour the reaction mixture was poured into ice-water and extracted with ethyl acetate. The organic extract was washed with water and saturated sodium chloride solution and dried (anhydrous magnesium sulfate), filtered and concentrated. Elution of the residue through silica with ethyl acetate via flash column chromatography yielded 1.8 g of a yellow oil. Conversion to the hydrochloride salt in 20% methanol in ether yielded 1.5 g of pale yellow crystals, mp 292°–294° (dec.).

ANALYSIS: Calculated for $C_{14}H_{12}ClFN_2S$: 57.04% C; 4.10% H; 9.51% N; Found: 56.84% C; 4.11% H; 9.13% N.

EXAMPLE 30

3-(Ethyl-4-pyridinylamino)-6-fluorobenzo[b]thiophene hydrochloride

6-Fluoro-3-(4-pyridinylamino)benzo[b]thiophene (2.5 g, 10.2 mmol) was added portionwise as a powder to a suspension of sodium hydride (60% oil dispersion, 0.7 g, 17.5 mmol, washed with hexanes) in 50 mL dimethylformamide. After the anion formation was completed, a solution of diethyl sulfate (1.9 g, 12.3 mmol) in 10 mL dimethylformamide was added. After one hour the reaction mixture was poured into ice-water and extracted with ethyl acetate. The organic extract was washed with water and saturated sodium chloride solution and dried (anhydrous magnesium sulfate), filtered and concentrated to 4 g of a brown oil. Elution through silica with ethyl acetate via flash column chromatography yielded 2.3 g of an amber oil. Conversion to the hydrochloride salt in 10% methanol in ether yielded 1.8 g of yellow crystals, mp 265°–266° (dec.).

ANALYSIS: Calculated for $C_{15}H_{14}ClFN_2S$: 58.34% C; 4.57% H; 9.07% N; Found: 58.26% C; 4.59% H; 9.01% N.

EXAMPLE 31

6-Fluoro-3-(propyl-4-pyridinylamino)benzo[b]thiophene hydrochloride

A solution of 6-fluoro-3-(4-pyridinylamino)benzo[b]thiophene (4.2 g) in 20 mL of dimethylformamide was slowly added to a suspension of sodium hydride (0.42 g) in 5 mL of dimethylformamide. Following the anion formation, a solution of 1-bromopropane (2.3 g) in 10 mL of dimethylformamide was added. After one hour the reaction mixture was stirred with water and extracted with ethyl acetate. The organic extract was washed successively with water and a saturated sodium chloride solution, and thereafter dried (anhydrous magnesium sulfate), filtered and concentrated to 5 g of a dark oil. This oil was eluted through silica gel with ethyl acetate via flash column chromatography to yield 3.3 g of a yellow oil. This oil was converted to the hydrochloride salt in 20% methanol in ether to yield 3.3 g of yellow crystal, m.p. 290°–292° C. (dec.).

ANALYSIS: Calculated for $C_{16}H_{16}ClFN_2S$: 59.53% C; 5.00% H; 8.68% N; Found: 59.16% C; 5.00% H; 8.26% N.

EXAMPLE 32

3-(Butyl-4-pyridinylamino)-6-fluorobenzo[b]thiophene hydrochloride

6-Fluoro-3-(4-pyridinylamino)benzo[b]thiophene (3 g, 12 mmol) was added portionwise as a powder to a suspension of sodium hydride (60% oil dispersion, 0.8 g, 20 mmol, washed with heptane) in 25 mL of dimethylformamide. After the anion formation was completed, a solution of 1-bromobutane (2 g, 14 mmol) in 5 mL of dimethylformamide was added. After one hour the reaction mixture was poured into ice-water and extracted with ether. The organic extract was washed with water and saturated sodium chloride solution and dried (anhydrous magnesium sulfate), filtered and concentrated to 5 g of a brown oil. Elution through silica with ethyl acetate via flash column chromatography yielded 3 g of an amber oil. Conversion to the hydrochloride salt in 10% methanol in ether yielded 2.5 g of yellow crystals, mp 219°–220°.

ANALYSIS: Calculated for $C_{17}H_{18}ClFN_2S$: 60.61% C; 5.39% H; 8.32% N; Found: 60.56% C; 5.43% H; 8.19% N.

EXAMPLE 33

3-[(3-Dimethylaminopropyl)-4-pyridinylamino]-6-fluorobenzo[b]thiophene

6-Fluoro-3-(4-pyridinylamino)benzo[b]thiophene (3.30 g, 13.5 mmol) was added portionwise as a powder to a suspension of sodium hydride (60% oil dispersion, 1.35 g, 33.8 mmol, washed with hexanes) in 50 mL dimethylformamide. After the anion formation was completed, 3-dimethylaminopropyl chloride hydrochloride (2.56 g, 16.2 mmol) was added as a powder and the resultant mixture was stirred at 70°–75° C. for two hours. After cooling, the reaction mixture was poured into ice-water and extracted with ethyl acetate. The organic extract was washed with water and saturated sodium chloride solution and dried (anhydrous magnesium sulfate), filtered and concentrated to 4.6 g of a brown oil. Elution through silica with 10% methanol in dichloromethane via flash column chromatography yielded 3.3 g of a yellow oil. Kugelrohr distillation (210°–220°/0.1 mm Hg) yielded 2.8 g of a clear colorless oil which eventually solidified to a white solid, mp 82°–84°.

ANALYSIS: Calculated for $C_{18}H_{20}FN_3S$: 65.62% C; 6.12% H; 12.75% N; Found: 65.42% C; 6.16% H; 12.58% N.

EXAMPLE 34

6-Fluoro-3-(3-fluoro-4-pyridinylamino)benzo[b]thiophene

A solution of 3-amino-6-fluorobenzo[b]thiophene (10 g, 60 mmol) and 4-chloro-3-fluoropyridine hydrochloride (12 g, 71 mmol) in 150 mL of 1-methyl-2-pyrrolidinone was stirred at 90°–95° for 2.5 h, and thereafter cooled, stirred with water and extracted with ether. The aqueous layer was basified with 30% aqueous ammonium hydroxide and extracted with ether. The organic extract was washed with water and saturated sodium chloride solution, and dried (anhydrous magnesium sulfate), filtered and concentrated to give 13 g of a solid. Elution through silica with 10% ethyl acetate in dichloromethane via flash column chromatography yielded 7 g (44.6%) of a white solid, mp 155°–157° C. Recrystallization of 2 g from acetonitrile afforded 1.3 g (29%) of white needles, mp 158°–159° C.

ANALYSIS: Calculated for $C_{13}H_8F_2N_2S$: 59.53% C; 3.07% H; 10.68% N; Found: 59.46% C; 3.36% H; 10.68% N; Found: 59.46% C; 3.36% H; 10.68% N.

EXAMPLE 35

6-Fluoro-3-[(3-fluoro-4-pyridinyl)propylamino]benzo[b]thiophene hydrochloride 6-Fluoro-3-(3-fluoro-4-pyridinylamino)benzo[b]thiophene (3 g, 11 mmol) was added portionwise as a powder to an ice-cooled suspension of sodium hydride (60% oil dispersion, 0.6 g, 15 mmol, washed with heptane) in 25 mL of dimethylformamide. After the anion formation was completed, 1-bromopropane (1.5 g, 12 mmol) was added. After warming and stirring one hour at ambient temperature the reaction mixture was poured into ice-water and extracted with ether. The organic extract was washed with water and saturated sodium chloride solution, and dried (anhydrous magnesium sulfate), filtered and concentrated to 4 g of a brown oil. Elution through silica with 10% ethyl acetate in dichloromethane via flash column chromatography afforded 2.2 g (63.2%) of a brown oil. Conversion to the hydrochloride salt in 10% methanol in ether afforded 2.5 g (64.1%) of a light tan powder, mp 239°-240° C.

ANALYSIS: Calculated for $C_{16}H_{15}ClF_2N_2S$: 56.38% C; 4.44% H; 8.22% N; Found: 56.15% C; 4.50% H; 8.15% N.

EXAMPLE 36

4-Chloro-3-[(4-pyridinyl)amino]benzo[b]thiophene hydrochloride

A solution of 4-chloro-3-aminobenzo[b]thiophene (20.31 g, 0.111 mole) and 4-chloropyridine (17.5 g, 0.116 mole) in 125 mL 1-methyl-2-pyrrolidinone was heated at 130° C. for 5 hours. The reaction was then quenched into a dilute $K_2CO_3$ solution and the aqueous phase was extracted with ethyl acetate (3×). The combined organics were washed with water (3×), dried (MgSO$_4$), filtered and concentrated. Purification via flash chromatography (EtOAc→1% MeOH/EtOAc) gave 16.2 g of a brown solid. A 2.12 g portion of this solid was dissolved in methanol, treated with ethereal HCl and the salt was crystallized out by the addition of ether to give 2.05 g of an orange solid. This was twice recrystallized from methanol/ether to give 1.61 g of an orange powder, mp: 302°-304° C. (dec.).

ANALYSIS: Calculated for $C_{13}H_9ClN_2S \cdot HCl$: 52.54% C; 3.39% H; 9.43% N; Found: 52.52% C; 3.26% H; 9.28% N.

EXAMPLE 37

4-Chloro-3-[(propyl)(4-pyridinyl)amino]benzo[b]thiophene hydrochloride hemi-hydrate A solution of 4-chloro-3-[(4-pyridinyl)amino]benzo[b]thiophene (2.50 g, 9.59 mmole) in 25 mL of dimethylformamide was added to a suspension of NaH (0.46 g of 60% in oil, 11.5 mmole) in DMF. To this was added 1-bromopropane (1.24 g, 10.1 mmole) and the reaction mixture was heated to 70° C. for 1 hour. The reaction mixture was then quenched into water and extracted with ethyl acetate (3×). The combined organics were washed with water (3×), dried (MgSO$_4$), filtered and concentrated. The isolated oil was passed through a column of alumina (EtOAc) leaving 2.38 g of an amber oil. After attempted purification via the maleic acid addition salt, all filtrates and isolated solids were converted to free base using potassium carbonate and purified via flash chromatography (EtOAc) to give 1.74 g of an oil. This was dissolved in acetonitrile, treated with ethereal HCl and the salt was crystallized out by the addition of ether. Collection of the resulting solid gave 1.21 g of an off-white powder, mp: 266°-268° C. (dec.).

ANALYSIS: Calculated for $C_{16}H_{15}ClN_2S \cdot HCl \cdot 0.5H_2O$: 55.17% C; 4.92% H; 8.04% N; Found: 55.49% C; 4.89% H; 8.12% N.

EXAMPLE 38

4-Chloro-3-[(2-methylpropyl)(4-pyridinyl)amino]benzo[b]thiophene fumarate

A solution of 4-chloro-3-[(4-pyridinyl)amino]benzo[b]thiophene (2.24 g, 8.59 mmole) in 25 mL of dimethylformamide was added to a suspension of NaH (0.412 g of 60% in oil, 10.3 mmole) in DMF. To this was added 1-bromo-2-methylpropane (1.24 g, 9.02 mmole) and the reaction mixture was heated to 70° C. During the next 5 hours, an additional 200 mg of NaH and 0.75 g of the bromo compound were added. The reaction mixture was then quenched into water and extracted with ethyl acetate (3×). The combined organics were washed with water (3×), dried (MgSO$_4$), filtered and concentrated. Purification of the residue via flash chromatography (EtOAc) gave 1.9 g of an oil. This was dissolved in methanol, treated with 1.1 eq. of fumaric acid and the salt was crystallized out by the addition of water to give 1.25 g of an off-white powder, mp: 181°-183° C.

ANALYSIS: Calculated for $C_{17}H_{17}ClN_2S \cdot C_4H_4O_4$: 58.26% C; 4.89% H; 6.47% N; Found: 58.09% C; 4.93% H; 6.44% N.

EXAMPLE 39

4-Chloro-3-[(3-{6-fluoro-3-benzisoxazolyl}propyl)(4-pyridinyl)amino]benzo[b]thiophene A solution of 4-chloro-3-[(4-pyridinyl)amino]benzo[b]thiophene (2.26 g, 8.67 mmole) in 25 mL DMF was added to a suspension of NaH (0.416 g of 60% in oil, 10.4 mmole, washed with heptane). To this mixture was added 3-(3-chloropropyl)-6-fluorobenzisoxazole (2.04 g, 9.53 mmole) and the reaction mixture was heated at 70° C. for 3 hours. The reaction mixture was quenched into water and extracted with ethyl acetate (3×). The organics were washed with water and dried (MgSO$_4$). The compound was purified via flash chromatography (EtOAc) to give 2.8 g of a partially solidified oil. This was recrystallized from methanol/water to give 1.38 g of a white powder, mp: 135°-136° C.

ANALYSIS: Calculated for $C_{23}H_{17}ClFN_3OS$: 63.08% C; 3.91% H; 9.60% N; Found: 62.78% C; 3.73% H; 9.55% N.

EXAMPLE 40

6-Chloro-3-(4-pyridinylamino)benzo[b]thiophene hydrochloride

A solution of 3-amino-6-chlorobenzo[b]thiophene (5 g, 27 mmol) and 4-chloropyridine hydrochloride (6 g, 40 mmol) in 75 mL of 1-methyl-2-pyrrolidinone was stirred at 80° for 1.5 h, and then was cooled, stirred with water and extracted with ether. The aqueous layer was basified with sodium carbonate and extracted with ethyl acetate. The organic extract was washed with water and saturated sodium chloride solution and then was dried (anhydrous magnesium sulfate), filtered and concentrated to a dark oil. Elution through silica with ethyl acetate via flash column chromatography yielded 7 g of an amber oil. Conversion to the hydrochloride salt in 20% methanol in ether yielded 4.2 g of yellow crystals, mp 264°-266° (dec.).

ANALYSIS: Calculated for $C_{13}H_{10}Cl_2N_2S$: 52.53% C; 3.39% H; 9.43% N; Found: 52.24% C; 3.38% H; 9.17% N.

EXAMPLE 41

6-Chloro-3-(methyl-4-pyridinylamino)benzo[b]thiophene hydrochloride

6-Chloro-3-(4-pyridinylamino)benzo[b]thiophene (3 g, 11.5 mmol) was added portionwise as a powder to an ice-cooled suspension of sodium hydride (60% oil dispersion, 0.7 g, 17.5 mmol, washed with heptane) in 25 mL of dimethylformamide. After anion formation was completed dimethyl sulfate (1.6 g, 12.7 mmol) was added. After one hour the reaction mixture was poured into ice-water and extracted with ether. The organic extract was washed with water and saturated sodium chloride solution, and dried (anhydrous magnesium sulfate), filtered and concentrated to give 3 g of a brown oil. Elution through silica with 10% methanol in ethyl acetate via flash column chromatography yielded 1.7 g of an amber oil. Conversion to the hydrochloride salt in 10% methanol in ether afforded 1.4 g of yellow crystals, mp 280°-281° C.

ANALYSIS: Calculated for $C_{14}H_{12}Cl_2N_2S$: 54.03% C; 3.89% H; 9.00% N; Found: 53.95% C; 3.87% H; 8.82% N.

EXAMPLE 42

6-Chloro-3-(ethyl-4-pyridinylamino)benzo[b]thiophene hydrochloride

6-Chloro-3-(4-pyridinylamino)benzo[b]thiophene (3 g, 11.5 mmol) was added portionwise as a powder to an ice-cooled suspension of sodium hydride (60% oil dispersion, 0.7 g, 17.5 mmol, washed with heptane) in 25 mL of dimethylformamide. After the anion formation was completed, diethyl sulfate (1.8 g, 11.7 mmol) was added. After one hour the reaction mixture was poured into ice-water and extracted with ether. The organic extract was washed with water and saturated sodium chloride solution, and dried (anhydrous magnesium sulfate), filtered and concentrated to give 5 g of a brown oil. Elution through silica with 10% methanol in ethyl acetate via flash column chromatography yielded 2.3 g of an amber oil. Conversion to the hydrochloride salt in 10% methanol in ether afforded 1.8 g of yellow crystals, mp 288°-290°.

ANALYSIS: Calculated for $C_{15}H_{14}Cl_2S$: 55.39% C; 4.34% H; 8.61% N; Found: 55.15% C; 4.35% H; 8.41% N.

EXAMPLE 43

6-Chloro-3-(propyl-4-pyridinylamino)benzo[b]thiophene hydrochloride

6-Chloro-3-(4-pyridinylamino)benzo[b]thiophene (4.2 g, 16.1 mmol) was added portionwise as a powder to an ice-cooled suspension of sodium hydride (60% oil dispersion, 0.8 g, 20 mmol, washed with heptane) in 25 mL of dimethylformamide. After the anion formation was completed, 1-bromopropane (2 g, 16.3 mmol) was added. After one hour the reaction mixture was poured into ice-water and extracted with ether. The organic extract was washed with water and saturated sodium chloride solution, and dried (anhydrous magnesium sulfate), filtered and concentrated to a brown oil. Elution through silica with 10% methanol in ethyl acetate via flash column chromatography yielded 3.5 g of an amber oil. Conversion to the hydrochloride salt in 10% methanol in ether afforded 3.7 g of a pale yellow powder, mp 276°-277° C.

ANALYSIS: Calculated for $C_{16}H_{16}Cl_2N_2S$: 56.64% C; 4.75% H; 8.26% N; Found: 56.37% C; 4.98% H; 8.02% N.

EXAMPLE 44

6-Chloro-3-[(1-methylethyl)(4-pyridyl)amino]benzo[b]thiophene hydrochloride

A solution of 6-chloro-3-(4-pyridinylamino)benzo[b]thiophene (2.43 g, 9.3 mmole) in 20 mL of dimethylformamide was added to a suspension of NaH (0.48 g of 60% in oil, 12.1 mmole) in DMF. To this was added 2-bromopropane (1.26 g, 10.2 mmole) and the reaction mixture was heated to 50° C. During the next 5 hours, an additional 200 mg of NaH and 1 g of the bromo compound were added three separate times. The reaction mixture was then quenched into water and extracted with ethyl acetate (3×). The combined organics were washed with water (3×), dried (MgSO₄), filtered and concentrated. Purification of the residue via flash chromatography ($C_6H_5CH_3 \rightarrow 5\% Et_3N/C_6H_5CH_3$) gave 1.57 of an oil. This was dissolved in acetonitrile, treated with ethereal HCl and the salt was crystallized out with additional ether to give 1.20 g of a yellowish powder, mp: 244°-246° C.

ANALYSIS: Calculated for $C_{16}H_{15}ClN_2S \cdot HCl$: 56.64% C; 4.75% H; 8.26% N; Found: 56.56% C; 4.47% H; 8.14% N.

EXAMPLE 45

6-Chloro-3-[(2-propenyl)(4-pyridinyl)amino]benzo[b]thiophene hydrochloride

A solution of 6-chloro-3-(4-pyridinylamino)benzo[b]thiophene (2.99 g, 11.5 mmole) in 25 mL of dimethylformamide was added to a suspension of NaH (0.59 g of 60% in oil, 14.9 mmole) in DMF. To this was added 3-bromopropene (1.67 g, 13.8 mmole) and the reaction mixture was heated to 70° C. After 1.5 hours, the reaction mixture was quenched into water and extracted with ethyl acetate (3×). The combined organics were washed with water (2×), dried (MgSO₄), filtered and concentrated. Purification of the residue via flash chromatography (DCM→2% MeOH/DCM) gave 1.83 g of an oil. This was dissolved in acetonitrile, treated with ethereal HCl and the salt was crystallized out with additional ether to give 1.40 g of a tan powder, mp: 260°-262° C. (dec.).

ANALYSIS: Calculated for $C_{16}H_{13}ClN_2S \cdot HCl$: 56.98% C; 4.18% H; 8.31% H; Found: 57.29% C; 4.16% H; 8.39% H.

EXAMPLE 46

6-Chloro-3-[(2-methoxyethyl)(4-pyridinyl)amino[benzo[b]thiophene hydrochloride

A solution of 6-chloro-3-(4-pyridinylamino)benzo[b]thiophene (2.3 g, 8.82 mmole) in 20 mL of dimethylformamide was added to a suspension of NaH (0.44 g of 60% in oil, 11.0 mmole) in DMF. To this was added chloroethyl methyl ether (0.92 g, 9.70 mmole) and the reaction mixture was heated to 80° C. After 3 hours, an additional 75 mg of NaH and 150 mg of the chloro compound were added and heating was continued for 2 hours. The reaction mixture was then quenched into water and extracted with ethyl acetate (3×). The combined organics were washed with water (3×), dried (MgSO₄), filtered and concentrated. Purification of the residue via flash chromatography (C₆H₅CH₃→10% Et₃N/C₆H₅CH₃) gave 1.7 g of an oil. This was dissolved in methanol, treated with ethereal HCl and the salt was crystallized out with additional ether to give 1.04 g of an off-white solid, mp: 224°–226° C.

ANALYSIS: Calculated for C₁₆H₁₅ClN₂OS.HCl: 54.09% C; 4.54% H; 7.88% N; Found: 54.40% C; 4.42% H; 7.66% N.

EXAMPLE 47

3-(Butyl-4-pyridinylamino)-6-chlorobenzo[b]thiophene hydrochloride

6-Chloro-3-(4-pyridinylamino)benzo[b]thiophene (5 g, 19 mmol) was added portionwise as a powder to a suspension of sodium hydride (60% oil dispersion, 0.8 g, 20 mmol, washed with heptane) in 50 mL of dimethylformamide. After the anion formation was completed, 1-bromobutane (2.8 g, 20 mmol) was added. After stirring one hour, the reaction mixture was poured into ice-water and extracted with ethyl acetate. The organic extract was washed with water and saturated sodium chloride solution, and dried (anhydrous magnesium sulfate), filtered and concentrated. Elution of the residue through silica with 5% methanol in ethyl acetate via flash column chromatography afforded 3.7 g of an oil. Elution through alumina with ether via column chromatography afforded 3.3 g of an oil. Conversion to the hydrochloride salt in 10% methanol in ether afforded 3.2 g of white crystals, mp 259°–260° C.

ANALYSIS: Calculated for C₁₇H₁₈Cl₂N₂S: 57.79% C; 5.14% H; 7.93% N; Found: 57.72% C; 5.19% H; 7.74% N.

EXAMPLE 48

6-Chloro-3-[(2-methylpropyl)(4-pyridinyl)amino]benzo[b]thiophene hydrochloride

A solution of the 6-chloro-3-(4-pyridinylamino)benzo[b]thiophene (2.75 g, 10.5 mmole) in 30 mL of dimethylformamide was added to a suspension of NaH (0.55 g of 60% in oil, 13.7 mmole) in DMF. To this was added 1-bromo-2-methylpropane (1.60 g, 11.6 mmole) and the reaction mixture was heated to 60° C. During the next 5 hours, an additional 200 mg of NaH and 1 g of the bromo compound were added three separate times. The reaction mixture was then quenched into water and extracted with ethyl acetate (3×). The combined organics were washed with water (3×), dried (MgSO₄), filtered and concentrated. Purification of the residue via flash chromatography (C₆H₅CH₃→3% Et₃N/C₆H₅CH₃) gave 2.9 g of an oil. This was dissolved in acetonitrile, treated with ethereal HCl and the salt was crystallized out with additional ether to give 2.47 g of a yellowish powder, mp: 264°–267° C.

ANALYSIS: Calculated for C₁₇H₁₇ClN₂S.HCl: 57.79% C; 5.14% H; 7.93% N; Found: 57.71% C; 4.87% H; 7.80% N.

EXAMPLE 49

6-Chloro-3-[(cyclopropylmethyl)(4-pyridyl)amino]benzo[b]thiophene hydrochloride

A solution of 6-chloro-3-[(4-pyridinyl)amino]benzo[b]thiophene (3.05 g, 11.7 mmole) in 25 mL of DMF was added to a suspension of NaH (0.56 g of 60% in oil, 14.0 mmole, washed with heptane). To this mixture was added bromomethylcyclopropane (1.16 g, 12.9 mmole) and the reaction mixture was heated at 75° C. for 2 hours. The reaction mixture was then quenched into water and extracted with ethyl acetate (3×). The organics were washed with water, dried (MgSO₄), filtered and concentrated. The residue was purified via flash chromatography (EtOAc→2% MeOH/EtOAc) to give an oil. This was dissolved in acetonitrile, treated with ethereal HCl and the salt was crystallized out of solution by the addition of ether. Filtration of the resulting solid gave 2.00 g of a tan powder, mp: 253°–255° C. (dec.).

ANALYSIS: Calculated for C₁₇H₁₅ClN₂S.HCl: 58.12% C; 4.59% H; 7.97% N; Found: 57.76% C; 4.66% H; 7.72% N.

EXAMPLE 50

6-Chloro-3-[(2,2-dimethylpropyl)(4-pyridinyl)amino]benzo[b]thiophene hydrochloride A solution of 6-chloro-3-[(4-pyridinyl)amino]benzo[b]thiophene (2.98 g, 11.4 mmole) in 20 mL of DMF was added to a suspension of NaH (0.55 g of 60% in oil, 13.7 mmole, washed with heptane). To this mixture was added 1-bromo-2,2-dimethylpropane (1.90 g, 12.6 mmole) and the reaction mixture was heated at 70° C. for 5 hours. Over the next 5 hours, 200 mg of NaH and 0.5 g of the bromo compound were added twice. The reaction was then quenched into water and extracted with ethyl acetate (3×). The organics were washed with water, dried (MgSO₄), filtered and concentrated. The residue was purified via flash chromatography (EtOAc→2% MeOH/EtOAc) to give 1.49 g of a fibrous solid. This was dissolved in acetonitrile, treated with ethereal HCl and the salt was crystallized out of solution by the addition of ether. Filtration of the resulting solid gave 1.05 g of a tan powder, mp: 270°–273° C. (dec.).

ANALYSIS: Calculated for C₁₈H₁₉ClN₂S.HCl: 58.86% C; 5.49% H; 7.63% N; Found: 58.68% C; 5.38% H; 7.49% N.

EXAMPLE 51

6-Chloro-3-[(3,3-dimethyl-2-propenyl)(4-pyridinyl)amino]benzo[b]thiophene hydrochloride A solution of 6-chloro-3-(4-pyridinylamino)benzo[b]thiophene (2.50 g, 9.59 mmole) in 20 mL of dimethylformamide was added to a suspension of NaH (0.46 g of 60% in oil, 11.5 mmole) in DMF. To this was added 4-bromo-2-methyl-2-butene (1.60 g, 10.5 mmole) and the reaction mixture was heated to 70° C. After 1 hour, the reaction mixture was poured into water and extracted with ethyl acetate (3×). The combined organics were washed with water (2×), dried (MgSO₄), filtered and concentrated. Purification of the residue via flash chromatography (EtOAc→1% MeOH/EtOAc) gave 1.7 g of an oil. This was dissolved in acetonitrile, treated with ethereal HCl and the salt was crystallized out with additional ether to give 1.25 g of a tan powder, mp: 217°–218° C. (dec.).

ANALYSIS: Calculated for C₁₈H₁₇ClN₂S.HCl: 59.18% C; 4.97% H; 7.67% N; Found: 59.11% C; 4.87% H; 7.61% N.

EXAMPLE 52

6-Chloro-3-[(cyclohexylmethyl)(4-pyridinyl)amino]benzo[b]thiophene hydrochloride A solution of 6-chloro-3-[(4-pyridinyl)amino]benzo[b]thiophene (2.49 g, 9.55 mmole) in 25 mL of DMF was added to a suspension of NaH (0.46 g of 60% in oil, 11.5 mmole, washed with heptane). To this mixture was added bromomethylcyclohexane (1.90 g, 10.5 mmole) and the reaction mixture was heated at 70° C. for 2.5 hours. The reaction mixture was then quenched into water and extracted with ethyl acetate (3×). The organics were washed with water, dried (MgSO₄), filtered and concentrated. Purification of the residue via flash chromatography (EtOAc) gave 2.81 g of an oil. This was dissolved in acetonitrile, treated with ethereal HCl and the salt was crystallized out of solution by the addition of ether. Filtration of the resulting solid gave 2.43 g of a tan powder, mp: 268°–271° C. (dec.).

ANALYSIS: Calculated for $C_{20}H_{21}ClN_2S \cdot HCl$: 61.07% C; 5.64% H; 7.12% N; Found: 61.18% C; 5.80% H; 6.84% N.

EXAMPLE 53

6-Chloro-3-[(benzyl)(4-pyridinyl)amino]benzo[b]thiophene hydrochloride

A solution of the 6-chloro-3-(4-pyridinylamino)benzo[b]thiophene (2.43 g, 9.32 mmole) in 20 mL of dimethylformamide was added to a suspension of NaH (0.45 g of 60% in oil, 11.2 mmole) in DMF. To this was added benzyl bromide (1.75 g, 10.3 mmole) and the reaction mixture was heated to 70° C. After 1.5 hours, the reaction was quenched into water and extracted with ethyl acetate (3×). The combined organics were washed with water (2×), dried (MgSO₄), filtered and concentrated. Purification of the residue via flash chromatography (EtOAc→1% MeOH/EtOAc) gave 2.25 g of an oil. This was dissolved in acetonitrile, treated with ethereal HCl and the salt was crystallized out with additional ether to give 1.65 g of a tan powder, mp: 267°–269° C. (dec.).

ANALYSIS: Calculated for $C_{20}H_{15}ClN_2S \cdot HCl$: 62.02% C; 4.16% H; 7.23% N; Found: 61.88% C; 4.22% H; 7.18% N.

EXAMPLE 54

6-Chloro-3-[(2-fluorobenzyl)(4-pyridinyl)amino]benzo[b]thiophene hydrochloride

A solution of 6-chloro-3-(4-pyridinylamino)benzo[b]thiophene (2.48 g, 9.50 mmole) in 20 mL of dimethylformamide was added to a suspension of NaH (0.46 g of 60% in oil, 11.4 mmole) in DMF. To this was added 2-fluorobenzyl bromide (1.98 g, 10.5 mmole) and the reaction mixture was heated to 70° C. After 1 hour, the reaction mixture was quenched into water and extracted with ethyl acetate (3×). The combined organics were washed with water (2×), dried (MgSO₄), filtered and concentrated. Purification of the residue via flash chromatography (EtOAc→1% MeOH/EtOAc) gave 2.20 g of an oil. This was dissolved in acetonitrile, treated with ethereal HCl and the salt was crystallized out with additional ether to give 1.67 g of a tan powder, mp: 265°–267° C. (dec.).

ANALYSIS: Calculated for $C_{20}H_{14}ClFN_2S \cdot HCl$: 59.27% C; 3.73% H; 6.91% N; Found: 59.32% C; 3.70% H; 6.95% N.

EXAMPLE 55

1-[4-[3-(6-Chlorobenzo[b]thien-3-yl-4-pyridinylamino)propoxy]-3-methoxyphenyl]ethanone 6-Chloro-3-(4-pyridinylamino)benzo[b]thiophene (4 g, 15 mmol) was added portionwise as a powder to a suspension of sodium hydride (60% oil dispersion, 0.7 g, 18 mmol, washed with heptane) in 50 mL of dimethylformamide. After the anion formation was completed, 1-[4-(3-chloropropoxy)-3-methoxyphenyl]ethanone (4 g, 16 mmol) was added. The reaction mixture was stirred two hours at 45° C., and then was poured into ice-water and extracted with ethyl acetate. The organic extract was washed with water and saturated sodium chloride solution, and then was dried (anhydrous magnesium sulfate), filtered and concentrated to 8 g of a dark oil. Elution through silica with 10% methanol in ethyl acetate via flash column chromatography afforded 4.1 g of a brown oil. Elution of this oil three times through silica with ethyl acetate via flash column chromatography afforded 3.0 g of a waxy solid. Recrystallization from acetonitrile afforded 2.1 g of white crystals, mp 148°–149° C.

ANALYSIS: Calculated for $C_{25}H_{23}ClN_2O_3S$: 64.30% C; 4.96% H; 6.00% N; Found: 64.12% C; 5.11% H; 6.05% N.

EXAMPLE 56

6-Chloro-3-[(4,4-{bis-[4-fluorophenyl]}butyl)(4-pyridinyl)amino]benzo[b]thiophene hydrochloride A solution of 6-chloro-3-[(4-pyridinyl)amino]benzo[b]thiophene (2.20 g, 8.44 mmole) in 25 mL of DMF was added to a suspension of NaH (0.405 g of 60% in oil, 10.1 mmole, washed with heptane) in 5 mL of DMF. To this mixture was added 4,4-bis-(4-fluorophenyl)butyl methanesulfonate (3.16 g, 9.28 mmole) and the reaction mixture was heated at 80° C. for 2 hours. The reaction mixture was then quenched into water and extracted with ethyl acetate (3×). The organics were washed with water, dried (MgSO₄), filtered and concentrated. Purification of the residue via flash chromatography (EtOAc) gave 2.5 g of an oil. This oil was dissolved in acetonitrile, treated with ethereal HCl and the salt was crystallized out of the solution by the addition of ether. The resulting solid was filtered to give 2.19 g of a white powder, mp: 232°–235° C. (dec.).

ANALYSIS Calculated for $C_{29}H_{23}ClF_2N_2S \cdot HCl$: 64.33% C; 4.47% H; 5.17% N; Found: 63.94% C; 4.51% H; 5.18% N.

EXAMPLE 57

6-Chloro-3-[(4-fluorobenzoylpropyl)(4-pyridinyl)amino]benzo[b]thiophene fumarate A solution of 6-chloro-3-[(4-pyridinyl)amino]benzo[b]thiophene (2.88 g, 11.0 mmole) in 30 mL of DMF was added to a suspension of NaH (0.53 g of 60% in oil, 13.3 mmole, washed with heptane) in 6 mL of DMF. To this mixture was added 2-(3-chloropropyl)-2-(4-fluorophenyl)dioxolane (3.2 g, 13.3 mmole) and the reaction mixture was heated at 70° C. for 0.5 hour. The reaction mixture was then quenched into water and extracted with ethyl acetate (3×). The organics were washed with water, dried (MgSO₄), filtered and concentrated. Purification of the residue through a column of florisil (EtOAc→2% MeOH/EtOAc) gave 4.24 g of a green oil. A mixture of the oil and 40 mL of concentrated HCl was heated on a steam bath for 45 minutes. The reaction was then quenched into iced water and basified with solid $K_2CO_3$. The aqueous phase was extracted with ethyl acetate and the combined organics were washed with water, dried (MgSO₄) and concentrated to give an oil. This oil was passed through a column of alumina (EtOAc) and then purified via flash chromatography (EtOAc) to give 1.8 g of a green oil. The free base was dissolved in methanol and treated with 1.1 eq. of fumaric acid. Removal of the solvent and crystallization of the residue with DCM gave 1.44 g of a white powder. This was recrystallized from methanol/water to give 0.856 g of a white powder, mp: 107°–110° C. (dec.).

ANALYSIS Calculated for $C_{23}H_{18}ClFN_2OS \cdot C_4H_4O_4$: 59.94% C; 4.10% H; 5.18% N; Found: 60.35% C; 4.09% H; 5.36% N.

EXAMPLE 58

6-Chloro-3-[(3-{6-fluoro-3-benzisoxazolyl}propyl)(4-pyridinyl)amino]benzo[b]thiophene hydrochloride A solution of 6-chloro-3-[(4-pyridinyl)amino]benzo[b]thiophene (2.63 g, 10.1 mmole) in 25 mL of DMF was added to a suspension of NaH (0.484 g of 60% in oil, 12.1 mmole, washed with heptane) in 5 mL of DMF. To this mixture was added 3-(3-chloropropyl)-6-fluorobenzisoxazole (2.50 g, 10.1 mmole) and the reaction mixture was heated at 70° C. for 1.5 hours. The reaction mixture was then quenched into water and extracted with ethyl acetate (3×). The organics were washed with water, dried (MgSO₄), filtered and concentrated. The residue was passed through a column of alumina (EtOAc) to give an oil. This was further purified via flash chromatography ($C_6H_5CH_3 \rightarrow 10\%$ MeOH/$C_6H_5CH_3$) to give 3.22 g of a blue oil. This was dissolved in methanol, treated with 1.1 eq. of fumaric acid, treated with charcoal, filtered and the salt was crystallized out of solution by the addition of water. Filtration of the resulting solid gave 2.87 g of a light green powder, mp: 137°–139° C.

ANALYSIS Calculated for $C_{23}H_{17}ClFN_3OS \cdot C_4H_4O_4$: 58.54% C; 3.82% H; 7.58% N; Found: 58.49% C; 3.74% H; 7.55% N.

EXAMPLE 59

7-Chloro-3-(4-pyridinyl)aminobenzo[b]thiophene hydrochloride

To a solution of 7-chloro-3-aminobenzo[b]thiophene (47.82 g, 325 mmole) in NMP (300 mL) was added 4-chloropyridine hydrochloride (50.78 g) and the reaction mixture was placed in a 130° C. oil bath. After stirring for 5 minutes, the reaction mixture was cooled, diluted with a saturated solution of NaHCO₃, and extracted with ethyl acetate. The biphasic mixture was thick with precipitates which were removed by filtration over Celite. The organic layer was separated, washed with water, dried (MgSO₄), and concentrated. Trituration of the resulting solid with diethyl ether/pentane yielded 28.95 g of product as a green solid. TLC revealed that the precipitates filtered in the initial extraction contained product. Flash chromatography (silica gel) and trituration of the resulting solid with diethyl ether/pentane yielded 11.32 g of an off-white solid. A 2.0 g portion of this material was dissolved in 40 mL of hot methanol allowed to stand for a half hour, filtered to remove orange precipitates. Ethereal hydrogen chloride was added to the filtrate. The hydrochloride salt was then filtered, washed with diethyl ether, and dried under high vacuum, P₂O₅, and refluxing xylenes to yield 1.89 g of a beige crystalline solid, mp 305° C. (dec.).

ANALYSIS Calculated for $C_{13}H_9N_2ClS \cdot HCl$: 52.54% C; 3.39% H; 9.43% N; Found: 52.84% C; 3.34% H; 9.34% N.

EXAMPLE 60

7-Chloro-3-[(propyl)(4-pyridinyl)amino]benzo[b]thiophene hydrochloride

To a suspension of NaH (452 mg, 11.29 mmole, washed with pentane) in dry DMF (15 mL) was added 1-bromopropane (1.03 mL, 11.29 mmole), and thereafter a solution of 7-chloro-3-[(4-pyridinyl)amino]benzo[b]thiophene (2.8 g, 10.75 mmole) in warm DMF (20 mL) was added so that the reaction mixture was warm to the touch. After the addition, the reaction mixture was stirred for two hours, distributed between water and ethyl acetate, and the organic phase was washed with water, dried (MgSO₄) and concentrated to afford 3.07 g of a dark brown oil. This was flash chromatographed twice (silica, 5% MeOH/EtOAc then 10% MeOH/EtOAc; alumina, Et₂O) to yield 2.36 g of product. The hydrochloride salt was formed in methanol with ethereal hydrogen chloride, the solution was concentrated to a solid and the solid was recrystallized from methanol and diethyl ether. The resulting pale yellow solid was dried for four hours under high vacuum over P₂O₅ and refluxing toluene to yield 1.77 g, mp 249° C. (dec.).

ANALYSIS Calculated for $C_{16}H_{15}ClN_2S \cdot HCl$: 56.64% C; 4.75% H; 8.26% N; Found: 56.62% C; 4.66% H; 8.15% N.

EXAMPLE 61

7-Chloro-3-[(2-methylpropyl)(4-pyridinyl)amino]benzo[b]thiophene hydrochloride

To a suspension of NaH (463 mg, 11.57 mmole, washed with pentane) in dry DMF (15 mL) was added 1-bromo-2-methylpropane (1.26 mL, 11.57 mmole), and thereafter a solution of 7-chloro-3-[(4-pyridinyl)amino]benzo[b]thiophene (2.87 g, 11.02 mmole) in warm DMF (20 mL) was added so that the reaction mixture was warm to the touch. After the addition, the reaction mixture was stirred for one hour and then heated to 60° C. An additional 232 mg of NaH and 0.63 mL of 1-bromo-2-methylpropane were added twice to drive the reaction to completion. The reaction mixture was then distributed between water and ethyl acetate, and the organic phase was washed with water, dried (MgSO₄) and concentrated to obtain 3.07 g of a dark brown oil. This was flash chromatographed twice (silica, 5% MeOH/EtOAc then 10% MeOH/EtOAc; alumina, Et₂O then EtOAc) to yield 2.02 g of product. The hydrochloride salt was formed in methanol with ethereal hydrogen chloride, concentrated to a solid and recrystallized from methanol and diethyl ether. The resulting white solid was dried for four hours under high vacuum over P₂O₅ and refluxing toluene to yield 1.61 g, mp 264° C. (dec.).

ANALYSIS Calculated for $C_{17}H_{17}ClN_2S \cdot HCl$: 57.79% C; 5.14% H; 7.93% N; Found: 57.97% C; 5.22% H; 7.83% N.

EXAMPLE 62

3-(4-Pyridinylamino)-6-trifluoromethylbenzo[b]thiophene hydrochloride

A solution of 3-amino-6-trifluoromethylbenzo[b]thiophene (7 g, 32 mmol) and 4-chloropyridine hydrochloride (6 g, 40 mmol) in 75 mL of 1-methyl-2-pyrrolidinone was stirred at 90° C. for one hour. After cooling, the reaction mixture was stirred with water, washed with ether and separated. The aqueous layer was basified with 30% aqueous ammonium hydroxide and extracted with ethyl acetate. The organic extract was washed with water and saturated sodium chloride solution, and then was dried (anhydrous magnesium sulfate), filtered and concentrated. Elution of the residue through silica with ethyl acetate via flash column chromatography afforded 7 g of a waxy solid. Conversion to the hydrochloride salt in 10% methanol in ether afforded 5 g of yellow crystals, mp 278°–279° C.

ANALYSIS Calculated for $C_{14}H_{10}ClF_3N_2S$: 50.84% C; 3.05% H; 8.47% N; Found: 50.77% C; 3.10% H; 8.30% N.

EXAMPLE 63

3-(Methyl-4-pyridinylamino)-6-trifluoromethylbenzo[b]thiophene hydrochloride

A solution of 3-(4-pyridinylamino)-6-trifluoromethylbenzo[b]thiophene (3.5 g, 12 mmol) in 20 mL of dimethylformamide was added to an ice-cooled suspension of sodium hydride (60% oil dispersion, 0.6 g, 15 mmol, washed with heptane) in 5 mL of dimethylformamide. After the anion formation was completed, a solution of dimethyl sulfate (1.5 g, 12 mmol) in 5 mL of dimethylformamide was added. After stirring one hour, the reaction mixture was poured into ice-water and extracted with ether. The organic extract was washed with water and saturated sodium chloride solution, and then was dried (anhydrous magnesium sulfate), filtered and concentrated. Elution of the residue through silica with 5% methanol in ethyl acetate via flash column chromatography afforded 2.3 g of a yellow oil. Conversion to the hydrochloride salt in 10% methanol in ether afforded 1.7 g of a yellow powder, mp 268°–270° C. (dec.).

ANALYSIS Calculated for $C_{15}H_{12}ClF_3N_2S$: 52.25% C; 3.51% H; 8.13% N; Found: 52.14% C; 3.40% H; 8.07% N.

EXAMPLE 64

3-(Ethyl-4-pyridinylamino)-6-trifluoromethylbenzo[b]thiophene hydrochloride

A solution of 3-(4-pyridinylamino)-6-trifluoromethylbenzo[b]thiophene (4 g, 14 mmol) in 20 mL of dimethylformamide was added to an ice-cooled suspension of sodium hydride (60% oil dispersion, 0.7 g, 18 mmol, washed with heptane) in 5 mL of dimethylformamide. After the anion formation was completed, a solution of diethyl sulfate (2.3 g, 15 mmol) in 5 mL of dimethylformamide was added. After stirring one hour, the reaction mixture was poured into ice-water and extracted with ether. The organic extract was washed with water and saturated sodium chloride solution, and then was dried (anhydrous magnesium sulfate), filtered and concentrated. Elution of the residue through silica with 10% methanol in ethyl acetate via flash column chromatography afforded 2.4 g of a yellow oil. Conversion to the hydrochloride salt in 10% methanol in ether afforded 2.3 g of a pale yellow powder, mp 266°–268° C. (dec.).

ANALYSIS: Calculated for $C_{16}H_{14}ClF_3N_2S$: 53.55% C; 3.93% H; 7.81% N; Found: 53.58% C; 3.69% H; 7.79% N.

EXAMPLE 65

3-(Propyl-4-pyridinylamino)-6-trifluoromethylbenzo[b]thiophene hydrochloride 3-(4-Pyridinylamino)-6-trifluoromethylbenzo[b]thiophene (3 g, 10 mmol) was added portionwise as a solid to an ice-cooled suspension of sodium hydride (60% oil dispersion, 0.5 g, 12 mmol, washed with heptane) in 25 mL of dimethylformamide. After the anion formation was completed, 1-bromopropane (1.5 g, 12 mmol) was added. After warming and stirring one hour at ambient temperature the reaction mixture was poured into ice-water and extracted with ether. The organic extract was washed with water and saturated sodium chloride solution, dried (anhydrous magnesium sulfate), filtered and concentrated to give 5 g of an oil. Elution through silica with ethyl acetate via flash column chromatography afforded 3.4 g of a solid, mp 120°–124° C. Conversion to the hydrochloride salt in 5% methanol in ether afforded 3 g of a hygroscopic solid. Recrystallization from 5% methanol in ether afforded 2.4 g of a white powder, mp 278°–280° C.

ANALYSIS: Calculated for $C_{17}H_{16}ClF_3N_2S$: 54.76% C; 4.33% H; 7.52% N; Found: 54.86% C; 4.38% H; 7.41% N.

EXAMPLE 66

3-[(2-Propenyl)(4-pyridinylamino)]-6-trifluoromethylbenzo[b]thiophene hydrochloride A solution of 3-(4-pyridinylamino)-6-trifluoromethylbenzo[b]thiophene (4 g, 14 mmol) in 20 mL of dimethylformamide was added to an ice-cooled suspension of sodium hydride (60% oil dispersion, 0.6 g, 15 mmol, washed with heptane) in 5 mL of dimethylformamide. After the anion formation was completed, 3-bromopropene (1.8 g, 15 mmol) was added. After stirring one hour, the reaction mixture was poured into ice-water and extracted with ether. The organic extract was washed with water and saturated sodium chloride solution, and then was dried (anhydrous magnesium sulfate), filtered and concentrated. Elution of the residue through silica with ethyl acetate via flash column chromatography afforded 3.4 g of a pale yellow oil. Conversion to the hydrochloride salt in 10% methanol in ether afforded 2.7 g of a white powder, mp 259°–260° C.

ANALYSIS: Calculated for $C_{17}H_{14}ClF_3N_2S$: 55.06% C; 3.81% H; 7.56% N; Found: 54.89% C; 3.68% H; 7.66% N.

EXAMPLE 67

3-(Butyl-4-pyridinylamino)-6-trifluoromethylbenzo[b]thiophene hydrochloride

A solution of 3-(4-pyridinylamino)-6-trifluoromethylbenzo[b]thiophene (4 g, 14 mmol) in 25 mL of dimethylformamide was added to an ice-cooled suspension of sodium hydride (60% oil dispersion, 0.7 g, 18 mmol, washed with heptane) in 5 mL of dimethylformamide. After the anion formation was completed, a solution of 1-bromobutane (2.1 g, 15 mmol) in 5 mL of dimethylformamide was added. After stirring one hour, the reaction mixture was poured into ice-water and extracted with ether. The organic extract was washed with water and saturated sodium chloride solution, and then was dried (anhydrous magnesium sulfate), filtered and concentrated. Elution of the residue through silica with 5% methanol in ethyl acetate via flash column chromatography afforded 4 g of a brown oil. Conversion to the hydrochloride salt in 10% methanol in ether afforded 3 g of a pale yellow powder, mp 288°–290° C. (dec.). Recrystallization from 10% methanol in ether afforded 2.5 g of white crystals, mp 298°–300° C. (dec.).

ANALYSIS: Calculated for $C_{18}H_{18}ClF_3N_2S$: 55.88% C; 4.69% H; 7.24% N; Found: 55.77% C; 4.69% H; 7.13% N.

EXAMPLE 68

3-[(2-Methylpropyl)(4-pyridinylamino)]-6-trifluoromethylbenzo[b]thiophene hydrochloride A solution of 3-(4-pyridinylamino)-6-trifluoromethylbenzo[b]thiophene (4 g, 14 mmol) in 25 mL of dimethylformamide was added to an ice-cooled suspension of sodium hydride (60% oil dispersion, 0.7 g, 18 mmol, washed with heptane) in 5 mL of dimethylformamide. After the anion formation was completed, a solution of 1-bromobutane (2.1 g, 15 mmol) in 5 mL of dimethylformamide was added. After stirring one hour the reaction mixture was poured into ice-water and extracted with ether. The organic extract was washed with water and saturated sodium chloride solution and thereafter dried (anhydrous magnesium sulfate), filtered and concentrated. Elution of the residue through silica with 5% methanol in ethyl acetate via flash column chromatography afforded 4 g of a brown oil. Conversion to the hydrochloride salt in 10% methanol in ether afforded 3.3 g of a white powder, mp 278°–280° C. (dec.).

ANALYSIS: Calculated for $C_{18}H_{18}ClF_3N_2S$: 55.88% C; 4.69% H; 7.24% N; Found: 55.68% C; 4.70% H; 7.18% N.

EXAMPLE 69

6-Methoxy-3-(4-pyridinylamino)benzo[b]thiophene hydrochloride

A solution of 3-amino-6-methoxybenzo[b]thiophene (8 g, 45 mmol) and 4-chloropyridine hydrochloride (6 g, 40 mmol) in 60 mL of 1-methyl-2-pyrrolidinone was stirred at 80°–85° C. for one hour. After cooling, the reaction mixture was stirred with water, washed with ether and separated. The aqueous layer was basified with 30% aqueous ammonium hydroxide and extracted with ethyl acetate. The organic extract was washed with water and saturated sodium chloride solution and then was dried (anhydrous magnesium sulfate), filtered and concentrated. Elution of the residue through silica with ethyl acetate via flash column chromatography afforded 4 g of an oil. Trituration with heptane afforded 3 g of a viscous oil. Conversion to the hydrochloride salt in 10% methanol in ether afforded 1.7 g of yellow crystals, mp 239°–240° C.

ANALYSIS: Calculated for $C_{14}H_{13}ClN_2OS$: 57.43% C; 4.48% H; 9.57% N; Found: 57.78% C; 4.46% H; 9.34% N.

EXAMPLE 70

7-Chloro-3-[(4-pyridinyl)(2,2-dimethylpropyl)amino]-benzo[b]thiophene hydrochloride To a mixture of sodium hydride (461 mg, 11.52 mmole) in DMF (10 mL) was added dropwise a warm filtered solution of 7-chloro-3-(4-pyridinyl)aminobenzo[b]thiophene (2.5 g, 9.60 mmole) in DMF (20 mL), followed by 1-bromo-2,2-dimethylpropane (1.45 mL, 11.52 mmole). This mixture was heated to 70° C. and stirred for two hours, after which additional sodium hydride (461 mg) and 1-bromo-2,2-dimethylpropane (1.5 mL) were added twice over two days, and thereafter another 200 mg and 0.75 mL of the respective reagants were added. After heating overnight, the reaction mixture was poured into ice water, extracted with ethyl acetate, the organics were washed twice with water, dried (MgSO4), and concentrated to obtain a dark oil. This was flash chromatographed (silica gel) (EtOAc, then 5% MeOH/EtOAc) to obtain 1.47 g of an oily solid. The hydrochloride salt was formed in methanol and diethyl ether and dried under high vacuum, $P_2O_5$, and refluxing xylenes to yield 1.25 g of a white solid, mp 310° C. (dec.).

ANALYSIS: Calculated for $C_{18}H_{19}N_2ClS.HCl$: 58.86% C; 5.49% H; 7.63% N; Found: 59.16% C; 5.48% H; 7.53% N.

EXAMPLE 71

7-Chloro-3-[(3-(4-fluorobenzoyl)propyl)(4-pyridinyl)amino]benzo[b]thiophene hydrochloride To a mixture of sodium hydride (645 mg, 16.13 mmole) in DMF (10 mL) was added dropwise a solution of 7-chloro-3-(4-pyridinyl)aminobenzo[b]thiophene (3.5 g, 13.44 mmole) in DMF (35 mL) and then 4'-fluoro-4-chlorobutyrophenone ethylene ketal (3.95 g, 16.13 mmole) was added. This mixture was heated with stirring at 70° C. for three hours, poured into ice and extracted with ethyl acetate. The organics were washed twice with water, dried (MgSO4), and then concentrated. The residue was flash chromatographed (silica gel; EtOAc, then 5% MeOH/EtOAc) to obtain a dark oil, which was dissolved in methanol and treated with "Norite" to obtain 2.88 g of a white froth after concentration. Concentrated HCl (30 mL) was added and the mixture was heated on a steam bath for 45 minutes. The reaction mixture was cooled, made basic with 10% sodium hydroxide and extracted with diethyl ether. The organics were washed with water and brine, dried (MgSO4), and concentrated to obtain a froth. The froth was dissolved in methanol and ethereal hydrogen chloride, concentrated, and the frothy oil was triturated with diethyl ether. The organics were decanted and the resulting solid was recrystallized from methanol and diethyl ether to obtain 2.09 g of a white solid, mp 229° C. (dec.), after drying under high vacuum, $P_2O_5$, and refluxing xylenes.

ANALYSIS: Calculated for $C_{23}H_{18}N_2ClFOS.HCl$: 59.87% C; 4.15% H; 6.07% N; Found: 59.47% C; 3.98% H; 5.96% N.

EXAMPLE 72

7-Chloro-3-[(4,4-{bis-[4-fluorophenyl]}butyl)(4-pyridinyl)amino]benzo[b]thiophene hydrochloride To a mixture of sodium hydride (461 mg, 11.52 mmole) in DMF (15 mL) was added dropwise a warm solution of 7-chloro-3-(4-pyridinyl)aminobenzo[b]thiophene (2.5 g, 9.60 mmole) in DMF (25 mL), followed by 4,4-[bis[4-fluorophenyl]]butylmethanesulfonate (3.92 g, 11.52 mmole). This mixture was heated to 70° C. and stirred for 2.5 hours, after which the reaction mixture was cooled and distributed between water and ethyl acetate. The organics were washed with brine, water, dried (MgSO4), and concentrated to obtain an oil. This was flash chromatographed on silica gel (EtOAc, then 10% MeOH/EtOAc) to obtain 2.92 g of an oil, containing DMF, which was taken up in diethyl ether and washed with water and brine. After drying over MgSO4, the organic solution was treated with "Darco"

to remove orange color. The hydrochloride salt was formed in methanol and diethyl ether, concentrated, and triturated with diethyl ether. After decanting the organics, the crude salt was recrystallized from methanol/diethyl ether and dried under high vacuum, $P_2O_5$, and refluxing n-butylacetate to yield 1.9 g of a white solid, mp 175°–176° C.

ANALYSIS: Calculated for $C_{29}H_{23}N_2ClF_2S.HCl$: 64.33% C; 4.47% H; 5.17% N; Found: 64.16% C; 4.82% H; 4.82% N.

EXAMPLE 73

7-Chloro-3-[(3-(4-acetyl-2-methoxyphenoxy)propyl)(4-pyridinyl)amino]benzo[b]thiophene hydrochloride hemihydrate To a mixture of sodium hydride (461 mg, 11.52 mmole) in DMF (10 mL) was added dropwise a filtered solution of 7-chloro-3-(4-pyridinyl)aminobenzo[b]thiophene (2.5 g, 9.60 mmole) in DMF (25 mL) and then 3-(4-acetyl-2-methoxyphenoxy)propylchloride (2.79 g, 11.52 mmole) was added. This mixture was heated with stirring at 70° C. for two hours. The reaction mixture was cooled, diluted with water, and extracted with ethyl acetate. The organics were washed twice with water, dried (MgSO$_4$), and then concentrated. The residue was flash chromatographed on silica gel (EtOAc, then 2.5% Et$_3$N/EtOAc, then 5% Et$_3$N/EtOAc) to obtain 3.36 g of a dark froth. The froth was tank up in methanol and treated with "Darco" to remove color and then the hydrochloride salt was formed in methanol and ethereal hydrogen chloride. Concentration followed by trituration with diethyl ether, and then recrystallization from methanol and diethyl ether yielded 1.88 g of a white solid, mp 189.5°–191° C., after drying under high vacuum, $P_2O_5$, and refluxing xylenes.

ANALYSIS: Calculated for $C_{25}H_{23}N_2ClO_3S.HCl.0.5H_2O$: 58.59% C; 4.92% H; 5.47% N; Found: 58.63% C; 4.59% H; 5.48% N.

EXAMPLE 74

7-Chloro-3-[(3-{6-fluoro-3-benzisoxazolyl}propyl)(4-pyridinyl)amino]benzo[b]thiophene hydrochloride To a mixture of sodium hydride (422 mg, 10.56 mmole) and 3-(3-chloropropyl)-6-fluoro-1,2-benzisoxazole (2.25 g, 10.56 mmole) in DMF (20 mL) was added dropwise a warm solution of 7-chloro-3-(4-pyridinyl)aminobenzo[b]thiophene (2.5 g, 9.60 mmole) in DMF (25 mL). The reaction mixture was stirred at 70° C. for one hour, after which 42.4 mg of sodium hydride and 225 mg of the benzisoxazole was added. The reaction mixture was stirred at room temperature overnight and then distributed between a saturated NaHCO$_3$ solution and ethyl acetate. The organics were washed with brine and water, dried (MgSO$_4$) and concentrated to obtain an oil. This was flash chromatographed on silica gel (EtOAc, then 5%Et$_3$N/EtOAc) to obtain 2.55 g of a froth and the hydrochloride salt was formed in methanol and diethyl ether to yield 2.34 g of a white solid, mp 246° C., after drying under high vacuum, P$_2$O$_5$, and refluxing xylenes.

ANALYSIS: Calculated for $C_{23}H_{17}N_3OClFS.HCl$: 58.23% C; 3.82% H; 8.86% N; Found: 58.12% C; 3.76% H; 8.77% N.

EXAMPLE 75

N-(5-Trifluoromethylbenzo[b]thien-3-yl)-4-pyridinamine hydrochloride

A solution of 3-amino-5-trifluoromethylbenzo[b]thiophene (27 g, 124 mmol) and 4-chloropyridine hydrochloride (20.5 g, 137 mmol) in 250 mL of 1-methyl-2-pyrrolidinone was stirred at 70°–80° C. for 1.5 hours. After cooling, the reaction mixture was stirred with water, washed with ether and separated. The aqueous layer was basified with a saturated sodium carbonate solution and the product which precipitated was collected. The reaction was repeated as above with an additional sample of 3-amino-5-trifluoromethylbenzo[b]thiophene (25.6 g, 118 mmol) and 4-chloropyridine hydrochloride (22 g, 148 mmol) in 225 mL of 1-methyl-2-pyrrolidinone. After a similar work-up, the two products were combined and dissolved in 10% methanol in ethyl acetate. The solution was dried (anhydrous magnesium sulfate), filtered and concentrated, yielding a yellow solid. This solid product was washed with ether and filtered to afford 39.1 g of a golden solid. Elution of a portion (3.5 g) of the residue through silica with ethyl acetate via flash column chromatography afforded 3.2 g of a white solid. Conversion of 2.4 g to the hydrochloride salt in 10% methanol in ether afforded 2.6 g of white crystals, mp 318°–319° C.

ANALYSIS: Calculated for $C_{14}H_9F_3N_2S.HCl$: 50.84% C; 3.05% H; 8.47% N; Found: 50.94% C; 2.95% H; 8.24% N.

EXAMPLE 76

N-Methyl-N-(5-trifluoromethylbenzo[b]thien-3-yl)-4-pyridinamine hydrochloride

A solution of N-(5-trifluoromethylbenzo[b]thien-3-yl)-4-pyridinamine (4g, 14 mmol) in 25 mL of dimethylformamide was added to an ice-cooled suspension of sodium hydride (60% oil dispersion, 0.7 g, 18 mmol, washed with heptane), in 5 mL of dimethylformamide. After the anion formation was completed, a solution of dimethyl sulfate (2.1 g, 17 mmol) in 5 mL of dimethylformamide was added. After stirring one hour, the reaction mixture was poured into ice-water and extracted with ether. The organic extract was washed with water and then was dried (anhydrous magnesium sulfate), filtered and concentrated. Elution of the residue through silica with 5% methanol in ethyl acetate via flash column chromatography afforded 3.0 g of an amber oil which solidified upon cooling. Conversion to the hydrochloride salt in 10% methanol in ether afforded 2.7 g of a white powder, mp 304°–307° C. (dec.).

EXAMPLE 77

N-Propyl-N-(5-trifluoromethylbenzo[b]thien-3-yl)-4-pyridinamine hydrochloride

A solution of N-(5-trifluoromethylbenzo[b]thien-3-yl)-4-pyridinamine (5.0 g, 17 mmol) in 20 mL of dimethylformamide was added dropwise to an ice-cooled suspension of sodium hydride (60% oil dispersion, 0.8 g, 20 mmol, washed with heptane), in 10 mL of dimethylformamide. After the anion formation was completed, 1-bromopropane (2.3 g, 1.7 mL, 17 mmol) was added dropwise. The mixture was stirred for one hour at 5°–10° C. At this time, the addition of 0.5 mL of 1-bromopropane (0.7 g, 5 mmol) was necessary. After one hour, the alkylation appeared complete by thin layer chromotography. The reaction mixture was poured into ice water and extracted several times with ethyl acetate. The organic extract was washed with water, dried (anhydrous magnesium sulfate), filtered and concentrated to afford 5.65 g of a light brown solid. Elution through silica with ethyl acetate via flash column chromatography afforded 4.4 g of a beige solid. conversion to the hydrochloride salt in 10% methanol in ether afforded 4.6 g of a white solid, mp 293°–294° c.

ANALYSIS: Calculated for $C_{17}H_{16}ClF_3N_2S$: 54.76% C; 4.33% H; 7.52% N; Found: 54.82% C; 4.09% H; 7.37% N.

EXAMPLE 78

N-(2-Methylpropyl)-N-(5-trifluoromethylbenzo[b]thien-3-yl)-4-pyridinamine hydrochloride A solution of N-(trifluoromethylbenzo[b]thien-3-yl)-4-pyridinamine (6.0 g, 20.4 mmol) in 25 mL of dimethylformamide was added dropwise to an ice-cooled suspension of sodium hydride (60% oil dispersion, 0.9 g, 22.4 mmol, washed with heptane), in 10 mL of dimethylformamide. After the anion formation was completed, 1-bromo-2-methylpropane (3.4 g, 24.6 mmol) was added dropwise. The mixture was stirred for two hours at 40°–50° C. At this time, the addition of sodium hydride (0.5 g, 11.2 mmol) and 1-bromo-2-methylpropane (1.7 g, 12.3 mmol) was necessary. After 1.5 hours, additional amounts of sodium hydride (0.5 g, 11.2 mmol) and 1-bromo-2-methylpropane (1.7 g, 12.3 mmol) were added to ensure complete alkylation. After stirring one additional hour, the reaction mixture was cooled, poured into ice water and extracted with ether. The organic extract was washed with water, dried (anhydrous magnesium sulfate), filtered and concentrated to afford 8.2 g of a brown solid. Elution through silica with ethyl acetate via flash column chromatography afforded 6.1 g of a pale yellow solid. Conversion to the hydrochloride salt in 10% methanol in ether afforded 5.6 g of white solid, mp 319°–320° C.

ANALYSIS: Calculated for $C_{18}H_{18}ClF_3N_2S$: 55.88% C; 4.69% H; 7.24% N; Found: 55.84% C; 4.57% H; 7.06% N.

EXAMPLE 79

6-Methoxy-3-(propyl-4-pyridinylamino)benzo[b]thiophene hydrochloride

A solution of 6-methoxy-3-(4-pyridinylamino)benzo[b]thiophene (3.4 g, 13 mmol) in 20 mL of dimethylformamide was added dropwise to an ice-cooled suspension of sodium hydride (60% oil dispersion, 0.6 g, 15 mmol, washed with heptane) in 5 mL of dimethylformamide. After the anion formation was completed, 1-bromopropane (1.8 g, 15 mmol) was added. After stirring one hour the reaction mixture was poured into ice-water and extracted with ethyl acetate. The organic extract was washed with water and saturated sodium chloride solution, and then was dried (anhydrous magnesium sulfate), filtered and concentrated to a dark oil. Gradient elution through silica with ethyl acetate followed by 10% methanol in ethyl acetate via flash column chromatography afforded 2 g of an oil. Conversion to the hydrochloride salt in 10% methanol in ether afforded 2 g of a light brown solid, mp 229°–230° C. (dec.). Recrystallization from 10% methanol in ether afforded 1.8 g of yellowish crystals, mp 229°–230° C. (dec.).

ANALYSIS: Calculated for $C_{17}H_{19}ClN_2OS$: 60.98% C; 5.72% H; 8.37% N; Found: 61.10% C; 5.40% H; 8.35% N.

EXAMPLE 80

6-Hydroxy-3-(propyl-4-pyridinylamino)benzo[b]thiophene hydrochloride

A solution of 6-methoxy-3-(propyl-4-pyridinylamino)benzo[b]thiophene (6 g, 20 mmol) in 50 mL of 48% hydrobromic acid was stirred at 120°–125° C. for one hour, and then cooled. The solution, after stirring with ice-water, was adjusted to pH 7 with sodium carbonate and the product was extracted with ethyl acetate. The organic extract was washed with water and saturated sodium chloride solution, and then was dried (anhydrous magnesium sulfate), filtered and concentrated to 2 g of a dark oil. Gradient elution through silica with ethyl acetate followed by 10% methanol in ethyl acetate via flash column chromatography afforded 1 g of a dark oil. Conversion to the hydrochloride salt in 10% methanol in ether afforded 0.9 g of a yellowish powder, mp 278°–280° C. (dec.).

ANALYSIS: Calculated for $C_{16}H_{17}ClN_2OS$: 59.89% C; 5.34% H; 8.73% N; Found: 59.65% C; 5.37% H; 8.44% N.

We claim:

1. A compound of the formula,

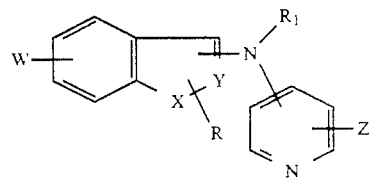

where

R is hydrogen, loweralkyl, carboxyl or loweralkoxycarbonyl;

$R_1$ is hydrogen, loweralkyl, loweralkenyl, loweralkynyl, arylloweralkyl, cycloalkylloweralkyl, loweralkoxyloweralkyl, hydroxyloweralkyl, aminoloweralkyl, mono- or di-loweralkylaminoloweralkyl, formyl, loweralkylcarbonyl, aminoloweralkylcarbonyl, loweralkoxycarbonyl, mono- or di-aryl-substituted loweralkyl, arylcarbonylloweralkyl, aryloxylloweralkyl,

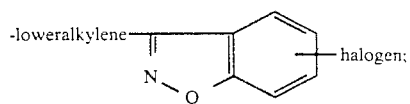

—X— is —N—,
           |
           $R_2$ $R_2$ being hydrogen, loweralkyl or loweralkylcarbonyl;

—Y— is —CH=, provided that the hydrogen atom of the group —CH= may be replaced by either the group R or the group

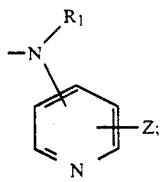

W is hydrogen, halogen, hydroxy, loweralkoxy, arylloweralkoxy, nitro, trifluoromethyl or

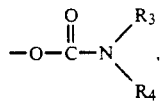

where $R_3$ is hydrogen, loweralkyl or arylloweralkyl; and $R_4$ is loweralkyl or arylloweralkyl; and Z is hydrogen, halogen, loweralkyl, nitro or amino; the term cycloalkyl signifying a cycloalkyl group of 3 to 8 carbon atoms, and the term aryl in each occurrence signifying a phenyl group substituted with 0, 1 or 2 substituents each of which being independently loweralkyl, loweralkoxy, loweralkylcarbonyl, halogen, or trifluoromethyl, or a pharmaceutically acceptable acid addition salt thereof.

2. The compound as defined in claim 1, wherein the group

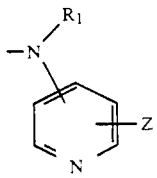

is present on the 2-position of the indole ring.

3. The compound as defined in claim 1, wherein the group

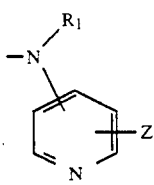

is present on the 3-position of the indole ring.

4. The compound as defined in claim 1, which is ethyl 3-(4-pyridinylamino)indole-2-carboxylate.

5. The compound as defined in claim 1, which is 6-chloro-3-(4-pyridinylamino)indole.

6. The compound as defined in claim 1, which is 3-(4-pyridinylamino)indole-2-carboxylic acid.

7. The compound as defined in claim 1, which is 6-fluoro-3-(4-pyridinylamino)indole.

8. The compound as defined in claim 1, which is 6-trifluoromethyl-3-(4-pyridinylamino)indole.

9. The compound as defined in claim 1, which is ethyl 1-methyl-3-(4-pyridinylamino)indole-2-carboxylate.

10. The compound as defined in claim 1, which is 1-acetyl-3-(4-pyridinylamino)indole.

11. A pharmaceutical composition which comprises a compound as defined in claim 1, in an amount effective for alleviating a memory dysfunction and a suitable carrier thereof.

* * * * *